United States Patent [19]

Angerbauer et al.

[11] Patent Number: 5,401,746
[45] Date of Patent: Mar. 28, 1995

[54] SUBSTITUTED PYRIDINES HEPTENOIC ACID DERIVATIVES, USEFUL FOR TREATING ARTERIOSCLEROS, LIPOPOTAEMIA AND THE LIKE

[75] Inventors: Rolf Angerbauer; Peter Fey; Walter Hübsch, all of Wuppertal; Thomas Philipps, Cologne; Hilmar Bischoff, Wuppertal; Dieter Petzinna, Duesseldorf; Delf Schmidt, Wuppertal, all of Germany; Günter Thomas, Arese, Italy

[73] Assignee: Bayer Aktiengesellschaft, Leverkusen, Germany

[21] Appl. No.: 916,928

[22] Filed: Jul. 20, 1992

Related U.S. Application Data

[60] Division of Ser. No. 627,086, Dec. 13, 1990, Pat. No. 5,169,857, which is a continuation-in-part of Ser. No. 298,549, Jan. 17, 1989, Pat. No. 5,006,530.

[30] Foreign Application Priority Data

Jul. 11, 1980 [IT] Italy ..................... 21317/88
Jan. 20, 1988 [DE] Germany ................. 33 01 406.8

[51] Int. Cl.$^6$ .............. C07D 213/55; A61K 31/44
[52] U.S. Cl. .................. 514/277; 546/342; 546/268
[58] Field of Search ............. 514/277; 546/342

[56] References Cited

U.S. PATENT DOCUMENTS 4,906,624  3/1990  Chucholowski et al. .......... 514/210

Primary Examiner—Alan L. Rotman
Attorney, Agent, or Firm—Sprung Horn Kramer & Woods

[57] ABSTRACT

Novel compounds for treating hyperproteinaemia, lipoproteinaemia or arteriosclerosis of the formula

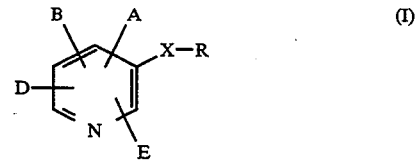

in which
A, B, D and E can have varied meanings,
X is $-CH_2-CH_2-$ or $-CH=CH-$, and
R is

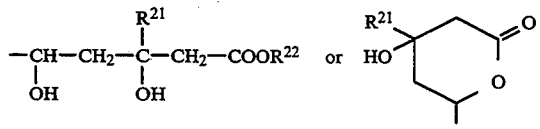

wherein
$R^{21}$—denotes hydrogen or alkyl and
$R^{22}$—denotes hydrogen,
   denotes alkyl, aryl or aralkyl, or
   denotes a cation,
and their oxidation products.

5 Claims, No Drawings

SUBSTITUTED PYRIDINES HEPTENOIC ACID DERIVATIVES, USEFUL FOR TREATING ARTERIOSCLEROS, LIPOPOTAEMIA AND THE LIKE

This is a division of application Ser. No. 07/627,086, filed Dec. 13, 1990, U.S. Pat. No. 5,169,857, which is a continuation-in-part of Ser. No. 07/298,549, filed Jan. 17, 1989, U.S. Pat. No. 5,006,530.

The invention relates to substituted pyridines, intermediates for their preparation, their preparation and their use in medicaments.

It is known that lactone derivatives isolated from fungal cultures are inhibitors of 3-hydroxy-3-methylglutaryl coenzyme A reductase (HMG-CoA reductase) [mevinolin, EP-A 22,478; U.S. Pat. No. 4,231,938]. Moreover, certain indole derivatives or pyrazole derivatives are also inhibitors of HMG-CoA reductase [EP-A 1,114,027; U.S. Pat. No. 4,613,610].

Substituted pyridines of the general formula (I)

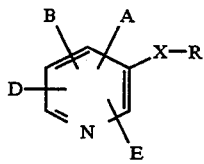

in which

A—stands for heteroaryl which can be monosubstituted, disubstituted or trisubstituted by identical or different halogen, alkyl, alkoxy, alkylthio, alkylsulphonyl, aryl, aryloxy, arylthio, arylsulphonyl, trifluoromethyl, trifluoromethoxy, trifluoromethylthio, alkoxycarbonyl or by a group of the formula —$NR^1R^2$, wherein $R^1$ and $R^2$—are identical or different and denote alkyl, aryl, aralkyl, acyl, alkylsulphonyl or arylsulphonyl, stands for aryl which can be mono substituted to pentasubstituted by identical or different alkyl which can be optionally substituted by hydroxyl or alkoxy, by alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl, dialkylcarbamoyl or by a group of the formula —$NR^1R^2$, wherein $R^1$ and $R^2$ have the abovementioned meaning and denote straight chain or branched alkyl, B—stands for cycloalkyl, or stands for alkyl which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl, acyl or by a group of the formula —$NR^1R^2$, wherein $R^1$ and $R^2$—are identical or different and denote alkyl, aryl, aralkyl, acyl, alkylsulphonyl or arylsulphonyl, or by carbamoyl, dialkyl carbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals of the last mentioned substituents can be mono substituted, disubstituted or trisubstituted by different halogen, cyano, trifluoromethyl, trifluoromethoxy, alkyl, alkoxy, alkylthio or alkylsulphonyl, D and E are identical or different and stand for hydrogen, or stand for CN or $NO_2$, or stand for cycloalkyl, or stand for straight-chain or branched alkyl which can be substituted by azido, halogen, hydroxy, cyano, alkoxy, alkylthio, alkylsulphonyl, trifluoromethyl, trifluoromethoxy, trifluoromethylthio, trifluoromethylsulphonyl, alkoxycarbonyl, acyl or by a group of the formula —$NR^1R^2$, wherein $R^1$ and $R^2$ have the abovementioned meaning, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals can be monosubstituted, disubstituted or trisubstituted by identical or different halogen, cyano, trifluoromethyl, trifluoromethoxy, alkyl, alkoxy, alkylthio or alkylsulphonyl, or stand for heteroaryl which can be monosubstituted, disubstituted or trisubstituted by identical or different halogen, alkyl, alkoxy, alkylthio, alkylsulphonyl, aryl, aryloxy, arylthio, arylsulphonyl, trifluoromethyl, trifluoromethoxy, trifluoromethylthio or alkoxycarbonyl, or by a group of the formula —$NR^1R^2$, wherein $R^1$ and $R^2$ have the abovementioned meaning, or stand for aryl which can be monosubstituted to pentasubstituted by identical or different alkyl which can be optionally substituted by hydroxyl or alkoxy, by alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl or dialkylcarbamoyl, or by a group of the formula —$NR^1R^2$, wherein $R^1$ and $R^2$ have the abovementioned meaning, or stand for a group of the formula —$NR^3R^4$, —$COR^5$ or —$CR^{11}R^{12}$—Y, wherein $R^3$ and $R^4$ are identical or different and denote hydrogen or denote alkyl, aryl or aralkyl, or denote a group of the formula —$COR^6$ or —$SO_2R^7$, or and $R^3$ and $R^4$ together form an alkylidene chain which can be interrupted by N, O, S and/or N-alkyl, N-aryl, N-aryl, N-carbamoyl or N-alkoxycarbonyl, $R^6$ stands for hydrogen, or stands for a group —$NHR^8$, or stands for alkoxy, or stands for alkyl, aryl, aryloxy, aralkyl, aralkoxy or heteroaryl, where the radicals mentioned can be monosubstituted, disubstituted or trisubstituted by identical or different alkyl, alkoxy, alkylthio, halogen, cyano, trifluoromethyl, trifluoromethoxy, trifluoromethylthio, amino, alkylamino or dialkylamino, $R^7$—stands for cycloalkyl, or
  stands for alkyl which can be substituted by cyano, halogen, trifluoromethyl, trifluoromethoxy or alkoxycarbonyl, or
  stands for aryl, aralkyl or heteroaryl, where the radicals mentioned can be monosubstituted, disubstituted or trisubstituted by identical or different alkyl, alkoxy, alkylthio, halogen, cyano, trifluoromethyl, trifluoromethoxy, trifluoromethylthio, amino, alkylamino or dialkylamino, and $R^8$—stands for hydrogen, or
  stands for cycloalkyl, or
  stands for alkyl which is optionally substituted by cyano, halogen, trifluoromethyl or trifluoromethoxy or
  stands for aryl, aralkyl or heteroaryl, where the radicals mentioned can be monosubstituted, disubstituted or trisubstituted by identical or different alkyl, alkoxy, alkylthio, halogen, cyano, trifluoromethyl, trifluoromethoxy, trifluoromethylthio, amino, alkylamino or dialkylamino, $R^5$—denotes hydrogen, cycloalkyl, hydroxyl, alkoxy, trimethylsilylalkoxy, aryloxy or aralkoxy, or
  stands for a group of the formula $-NR^9R^{10}$,
wherein
  $R^9$ and $R^{10}$ are identical or different and denote hydrogen, alkyl, aryl or aralkyl, or
  denote an optionally substituted heterocyclic radical, which is bonded via a nitrogen atom, from the series comprising pyrrolidine, piperidine, morpholine, thiomorpholine or piperazine, and $R^{11}$ and $R^{12}$ can be identical or different and
  stand for hydrogen, or
  stand for alkyl which can optionally be substituted by hydroxyl, halogen, alkoxy or alkoxycarbonyl, or
  stand for cycloalkyl, or
$R^{11}$ and $R^{12}$ together form a saturated or unsaturated carbocyclic or heterocyclic ring having up to 6 carbon atoms, and Y—denotes a group of the formula $-NR^{13}R^{14}$, $-COR^{15}$, $-S-R^{16}$, $-SO-R^{16}$, $-SO_2R^{16}$, $-OR^{17}$ or $-N_3$,
wherein
  $R^{13}$ and $R^{14}$ are identical or different and
    stand for hydrogen, alkyl, aryl or aralkyl, where the aryl radicals can be substituted by halogen, cyano, alkyl, alkoxy or trifluoromethyl, or
    stand for a group of the formula $-COR^{15}$ or $-SO_2R^{16}$,
  or $R^{13}$ and $R^{14}$ together form an alkylene chain which can be interrupted by N, O, S and/or N-alkyl, N-aryl, N-aralkyl, N-carbamoyl or N-alkoxycarbonyl, $R^{15}$—denotes hydrogen, or
  denotes a group $-NR^{18}R^{19}$, or
  denotes alkyl or alkoxy, or
  denotes aryl, aryloxy, aralkyl, aralkoxy or heteroaryl, where the radicals mentioned can be monosubstituted, disubstituted or trisubstituted by identical or different alkyl, alkoxy, alkylthio, halogen, cyano, trifluoromethyl, trifluoromethoxy, trifluoromethylthio, amino, alkylamino or dialkylamino, $R^{16}$—denotes cycloalkyl, or
  denotes straight-chain or branched alkyl which can be substituted by cyano, halogen, trifluoromethyl, trifluoromethoxy or alkoxycarbonyl, or
  denotes aryl, aralkyl or heteroaryl, where the radicals mentioned can be monosubstituted, disubstituted or trisubstituted by identical or different alkyl, alkoxy, alkylthio, halogen, cyano, trifluoromethyl, trifluoromethoxy, trifluoromethylthio, amino, alkylamino or dialkylamino, or
  denotes trimethylsilyl or dimethylethylsilyl, or
  denotes a group $-NR^9R^{10}$,
where
  $R^9$ and $R^{10}$ have the abovementioned meaning, $R^{17}$—stands for hydrogen, or
  stands for cycloalkyl, or
  stands for alkyl which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl or acyl, or by a group of the formula $-NR^1R^2$,
wherein
  $R^1$ and $R^2$ have the abovementioned meaning, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals can be monosubstituted, disubstituted or trisubstituted by identical or different halogen, cyano, trifluoromethyl, trifluoromethoxy, alkyl, alkoxy, alkylthio or alkylsulphonyl, or
  stands for heteroaryl which can be monosubstituted, disubstituted or trisubstituted by identical or different halogen, alkyl, alkoxy, alkylthio, alkylsulphonyl, aryl, aryloxy, arylthio, arylsulphonyl, trifluoromethyl, trifluoromethoxy, trifluoromethylthio or alkoxycarbonyl, or by a group of the formula $-NR^1R^2$,
wherein
  $R^1$ and $R^2$ have the abovementioned meaning, or
  stands for aryl which can be monosubstituted to pentasubstituted by identical or different alkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl or dialkylcarbamoyl, or by a group of the formula $-NR^1R^2$,
wherein
  $R^1$ and $R^2$ have the abovementioned meaning, or
  stands for 2,5-dioxo-tetrahydropyrryl,
  stands for tetrahydropyranyl, or
  stands for trialkylsilyl, or denotes a group $COR^{16}$,
where
  $R^{16}$ has the abovementioned meaning,
and
  $R^{18}$ and $R^{19}$ are identical or different and
    denote hydrogen, or
    denote cycloalkyl, or
    denote alkyl which is optionally substituted by cyano, halogen, trifluoromethyl or trifluoromethoxy, or
    denote aryl, aralkyl or heteroaryl, where the radicals mentioned can be monosubstituted, disubstituted or trisubstituted by identical or different alkyl, alkoxy, alkylthio, halogen, cyano, trifluoromethyl, trifluoromethoxy, trifluoromethylthio, amino, alkylamino or dialkylamino, or D and E together stand for a radical of the formula

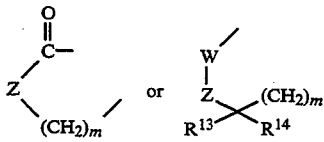

and form a ring, where
W—stands for a group of the formula

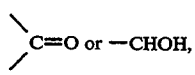

m—stands for a number 1, 2 or 3,
Z—stands for O, S, $CH_2$ or for N—$R^{20}$,
$R^{13}$ and $R^{14}$ have the abovementioned meaning, and
$R^{20}$—stands for hydrogen, alkyl aryl, aralkyl, carbamoyl or alkoxycarbonyl,
and where in this case D and E are adjacent,
X—stands for a group of the formula —$CH_2$—$CH_2$— or —CH=CH—, and
R—stands for a group of the formula

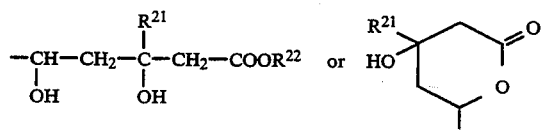

wherein
$R^{21}$—denotes hydrogen or alkyl and
$R^{22}$—denotes hydrogen,
denotes alkyl, aryl or aralkyl, or
denotes a cation,
and their oxidation products have now been found.

Among the oxidation products of the compounds of the general formula (I) according to the invention, there are understood the corresponding compounds of the pyridine N-oxide.

Surprisingly, the substituted pyridines according to the invention show a superior inhibitory action on HMG-CoA reductase (3-hydroxy-3-methyl-glutaryl coenzyme A reductase).

Cycloalkyl in general stands for a cyclic hydrocarbon radical having 3 to 8 carbon atoms. The cyclopropyl, cyclopentyl and cyclohexyl ring is preferred. Examples which may be mentioned are cyclopropyl, cyclopentyl, cyclohexyl, cycloheptyl and cyclooctyl.

Alkyl in general stands for a straight-chain or branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkoxy in general stands for a straight-chain or branched hydrocarbon radical having 1 to 12 carbon atoms which is bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexyloxy, heptoxy, isoheptoxy, octoxy and isooctoxy.

Alkylthio in general stands for a straight-chain or branched hydrocarbon radical having 1 to 12 carbon atoms which is bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio, and isooctylthio.

Alkylsulphonyl in general stands for a straight-chain or branched hydrocarbon radical having 1 to 12 carbon atoms which is bonded via an $SO_2$ group. Lower alkylsulphonyl having 1 to about 6 carbon atoms is preferred. Examples which may be mentioned are: methylsulphonyl, ethylsulphonyl, propylsulphonyl, isopropylsulphonyl, butylsulphonyl, isobutylsulphonyl, pentylsulphonyl, isopentylsulphonyl, hexylsulphonyl and isohexylsulphonyl.

Sulphamoyl (aminosulphonyl) stands for the group —$SO_2$—$NH_2$.

Aryl in general stands for an aromatic radical having 6 to about 12 carbon atoms. Preferred aryl radicals are phenyl, naphthyl and biphenyl.

Aryloxy in general stands for an aromatic radical having 6 to about 12 carbon atoms which is bonded via an oxygen atom. Preferred aryloxy radicals are phenoxy and naphthyloxy.

Arylthio in general stands for an aromatic radical having 6 to about 12 carbon atoms which is bonded via a sulphur atom. Preferred arylthio radicals are phenylthio and naphthylthio.

Arylsulphonyl in general stands for an aromatic radical having 6 to about 12 carbon atoms which is bonded via an $SO_2$ group. Examples which may be mentioned are phenylsulphonyl, naphthylsulphonyl and biphenylsulphonyl.

Aralkyl in general stands for an aryl radical having 7 to 14 carbon atoms which s bonded via an alkylene chain. Aralkyl radicals having 1 to 6 carbon atoms in the aliphatic moiety and 6 to 12 carbon atoms in the aromatic moiety are preferred. Examples which maybe mentioned are the following alkyl radicals: benzyl, naphthylmethyl, phenethyl and phenylpropyl.

Aralkoxy in general stands for an aralkyl radical having 7 to 14 carbon atoms, the alkylene chain being bonded via an oxygen atom. Aralkoxy radicals having 1 to 6 carbon atoms in the aliphatic moiety and 6 to 12 carbon atoms in the aromatic moiety are preferred. Examples which may be mentioned are the following aralkoxy radicals: benzyloxy, naphthylmethoxy, phenethoxy and phenylpropoxy.

Aralkylthio in general stands for an aralkyl radical having 7 to about 14 carbon atoms, the alkyl chain being bonded via a sulphur atom. Aralkylthio radicals having 1 to 6 carbon atoms in the aliphatic moiety and 6 to 12 carbon atoms in the aromatic moiety are preferred. Examples which may be mentioned are the following aralkylthio radicals: benzylthio, naphthylmethylthio, phenethylthio and phenylpropylthio.

Aralkylsulphonyl in general stands for an aralkyl radical having 7 to about 14 carbon atoms, the alkyl radical being bonded via an $SO_2$ link. Aralkylsulphonyl radicals having 1 to 6 carbon atoms in the aliphatic moiety and 6 to 12 carbon atoms in the aromatic moiety are preferred. Examples which may be mentioned are the following aralkylsulphonyl radicals: benzylsulphonyl, naphthylmethylsulphonyl, phenethylsulphonyl and phenylpropylsulphonyl.

Alkoxycarbonyl can be represented, for example, by the formula

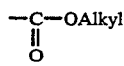

In this connection, alkyl stands for a straight-chain or branched hydrocarbon radical having 1 to 12 carbon atoms. Lower alkoxycarbonyl having 1 to about 6 carbon atoms in the alkyl moiety is preferred. An alkoxycarbonyl having 1 to 4 carbon atoms in the alkyl moiety is particularly preferred. Examples which may be mentioned are the following alkoxycarbonyl radicals: methoxycarbonyl, ethoxycarbonyl, propoxycarbonyl, isopropoxycarbonyl, butoxycarbonyl and isobutoxycarbonyl.

Acyl in general stands for phenyl or straight-chain or branched lower alkyl having 1 to about 6 carbon atoms which are bonded via a carbonyl group. Phenyl and alkyl radicals having up to 4 carbon atoms are preferred. Examples which may be mentioned are benzoyl, acetyl, ethylcarbonyl, propylcarbonyl, isopropylcarbonyl, butylcarbonyl and isobutylcarbonyl.

Halogen in general stands for fluorine, chlorine, bromine or iodine, preferably for fluorine, chlorine or bromine. Particularly preferably, halogen stands for fluorine or chlorine.

Heteroaryl in general stands for a 5- to 6-membered aromatic ring which can contain oxygen, sulphur and/or nitrogen as hetero atoms and onto which can be fused further aromatic rings. 5- and 6-membered aromatic rings which contain one oxygen, one sulphur and/or up to 2 nitrogen atoms and which are optionally fused to benzene are preferred. Heteroaryl radicals which may be mentioned as particularly preferred are thienyl, furyl, pyrolyl, pyrazolyl, pyridyl, pyrimidyl, pyrazinyl, pyridazinyl, quinolyl, isoquinolyl, quinazolyl, quinoxalyl, phthalazinyl, cinnolyl, thiazolyl, benzothiazolyl, isothiazolyl, oxazolyl, benzoxazolyl, isoxazolyl, imidazolyl, benzimidazolyl, pyrazolyl, indolyl and isoindolyl.

If $R^{22}$ stands for an ester radical, then a physiologically tolerable ester radical is preferably meant by this, which is easily hydrolyzed in vivo to a free carboxyl group and a corresponding physiologically tolerable alcohol. These include, for example, alkyl esters ($C_1$ to $C_4$) and aralkyl esters ($C_7$ to $C_{10}$), preferably lower alkyl esters and benzyl esters. Moreover, the following ester radicals may be mentioned: methyl esters, ethyl esters, propyl esters and benzyl esters.

If $R^{22}$ stands for a cation then a physiologically tolerable metal cation or ammonium cation is preferably meant. In this connection, alkali metal cations or alkaline earth metal cations such as, for example, sodium cations, potassium cations, magnesium cations or calcium cations, and also aluminum cations or ammonium cations, and also non-toxic substituted ammonium cations from amines such as dilower alkylamines, trilower alkylamines, procain, dibenzylamine, N,N'-dibenzylethylenediamine, N-benzyl-β-phenylethylamine, N-methylmorpholine or N-ethylmorpholine, 1-ephenamine, dihydroabietylamine, N,N'-bis-dihydroabietylethylenediamine, N-lower alkylpiperidine and other amines which can be used for the formation of salts are preferred.

In the context of the present invention, substituted pyridines (Ia) correspond to the general formula

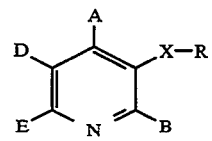

in which

A, B, D, E, X and R have the abovementioned meaning.

In the context of the present invention, substituted pyridines (Ib) correspond to the general formula

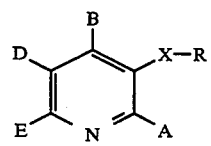

in which

A, B, D, E, X and R have the abovementioned meaning.

In the context of the general formula (I), compounds of the general formulae (Ia) and (Ib) are preferred.

Preferred compounds are those of the general formulae (Ia) and (Ib)

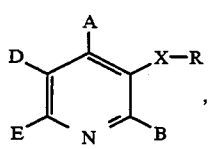

,

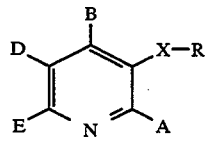

in which

A—stands for thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by identical or different fluorine, chlorine, bromine, lower alkyl, lower alkoxy, phenyl, phenoxy, trifluoromethyl, trifluoromethoxy or lower alkoxycarbonyl, or stands for phenyl or naphthyl, each of which can be monosubstituted to tetrasubstituted by identical or different lower alkyl which can optionally be substituted by hydroxyl or lower alkoxy, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine or cyano, $R^1$ and $R^2$ are identical or different and denote lower alkyl, phenyl, benzyl, acetyl, benzoyl, phenyl sulphonyl or lower alkylsulphonyl, stands for straight-chain or branched lower alkyl, B—stands for cyclopropyl, cyclopentyl or cyclohexyl, or stands for lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl, lower alkylcarbonyl, or by a group of the formula —$NR^1R^2$, wherein $R^1$ and $R^2$ have the abovementioned meaning, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, where the heteroaryl and aryl radicals mentioned can be monosubstituted or disubstituted by identical or different fluorine, chlorine, bromine, lower alkyl, lower alkoxy, trifluoromethyl or trifluoromethoxy, D and E—are identical or different and stand for hydrogen, or stand for CN or $NO_2$, or stand for cyclopropyl, cyclopentyl or cyclohexyl, or stand for straight-chain or branched lower alkyl which can be substituted by azido, fluorine, chlorine, bromine, cyano, hydroxyl, lower alkoxy, lower alkylthio, lower alkylsulphonyl, trifluoromethyl, trifluoromethoxy, trifluoromethylsulphonyl, lower alkoxycarbonyl, benzoyl lower alkylcarbonyl, or by a group of the formula —$NR^1R^2$ wherein $R^1$ and $R^2$ have the abovementioned meaning, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, where the heteroaryl and aryl radicals mentioned can be monosubstituted or disubstituted by identical or different fluorine, chlorine, bromine, lower alkyl, lower alkoxy, trifluoromethyl or trifluoromethoxy, stand for thienyl, furyl, thiazolyl, tetrazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by identical or different fluorine, chlorine, bromine, lower alkyl, lower alkoxy, phenyl, phenoxy, trifluoromethyl, trifluoromethoxy or lower alkoxycarbonyl, or stand for phenyl or naphthyl which can be monosubstituted to tetrasubstituted by identical or different lower alkyl which can be optionally substituted by hydroxyl or lower alkoxy, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio, lower alkoxycarbonyl or by a group of the formula —$NR^1R^2$, where $R^1$ and $R^2$ have the abovementioned meaning, or for a group of the formula —$NR^3R^4$, —$COR^5$ or —$CR^{11}R^{12}$—Y, wherein $R^3$ and $R^4$ are identical or different and denote hydrogen or denote lower alkyl, phenyl or benzyl, or denote a group of the formula —$COR^6$ or —$SO_2R^7$, where $R^6$—stands for hydrogen, or stands for a group —$NHR^8$, or stands for lower alkoxy, or stands for lower alkyl, phenyl, benzyl, benzyloxy, thienyl, furyl, pyridyl, pyrimidyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, $R^7$—stands for cyclopropyl, cyclopentyl or cyclohexyl, or stands for lower alkyl which is optionally substituted by cyano, fluorine, chlorine, bromine, trifluoromethyl or lower alkoxycarbonyl, or stands for phenyl, benzyl, thienyl, furyl, pyrimidyl, pyridyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, and $R^8$—stands for hydrogen, or stands for lower alkyl which is optionally substituted by cyano, fluorine, chlorine or bromine, or stands for phenyl, benzyl, thienyl, furyl, pyridyl, pyrimidyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, $R^5$—denotes hydrogen, cyclohexyl, hydroxyl, lower alkoxy, trimethylsilyl lower alkoxy or benzyloxy, or stands for a group of the formula —$NR^9R^{10}$, wherein $R^9$ and $R^{10}$ are identical or different and denote hydrogen, lower alkyl or phenyl, or denote a heterocyclic ring from the series comprising pyrrolidine, piperidine, piperazine, N-alkylpiperazine, N-arylpiperazine, N-benzylpiperazine, N-carbamoylpiperazine or N-alkoxycarbonylpiperazine, and $R^{11}$ and $R^{12}$ can be identical or different and stand for hydrogen, or stand for lower alkyl which can optionally be substituted by hydroxyl, fluorine, chlorine, lower alkoxy or lower alkoxycarbonyl, or stand for cyclopropyl, cyclopentyl or cyclohexyl, or $R^{11}$ and $R^{12}$ together form a saturated or unsaturated carbocyclic or heterocyclic ring having up to 6 carbon atoms, Y—denotes a group of the formula $-NR^{13}R^{14}$, $-COR^{15}$, $-S-R^{16}$, $SO-R^{16}$, $-OR^{17}$ or $N_3$ where $R^{13}$ and $R^{14}$ are identical or different and stand for hydrogen, lower alkyl, phenyl or benzyl, where the radicals mentioned can be substituted by fluorine, chlorine, bromine, lower alkyl, lower alkoxy or trifluoromethyl, or stand for a group of the formula $-COR^{15}$, $-SO_2R^{16}$, or $R^{13}$ and $R^{14}$ together form an alkylene chain which can be interrupted by O, N, S, N-lower alkyl, N-benzyl, N-phenyl, N-carbamoyl or N-lower alkoxycarbonyl, $R^{15}$—denotes a group $-NR^{18}R^{19}$, or denotes lower alkyl or lower alkoxy, or denotes phenyl, benzyl, benzyloxy, thienyl, furyl, pyridyl, pyrimidyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, $R^{16}$—denotes cyclopropyl, cyclopentyl, cyclohexyl, or denotes straight-chain or branched lower alkyl which is optionally substituted by cyano, fluorine, chlorine, bromine, trifluoromethyl or lower alkoxycarbonyl, or denotes phenyl, naphthyl, benzyl, thienyl, furyl, pyrimidyl, pyridyl, quinolyl, isoquinolyl, benzothiazolyl, benzoxazolyl, thiazolyl, oxazolyl, isoxazolyl or isothaazolyl which are optionally monosubstituted or polysubstituted by identical or different lower alkyl, lower alkoxy, fluorine, chlorine, bromine, trifluoromethyl, dimethylamino or diethylamino, or denotes, trimethylsilyl or dimethylethylsilyl, or denotes a group $-NR^9R^{10}$, where $R^9$ and $R^{10}$ have the abovementioned meaning, $R^{17}$—stands for hydrogen, or stands for cyclopropyl, cyclopentyl or cyclohexyl, or stands for lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl, lower alkylcarbonyl, or by a group of the formula $-NR^1R^2$, wherein $R^1$ and $R^2$ have the abovementioned meaning, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, where the heteroaryl and aryl radicals mentioned can be monosubstituted or disubstituted by identical or different fluorine, chlorine, bromine, lower alkyl, lower alkoxy, trifluoromethyl, or trifluoromethoxy, stands for thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by identical or different fluorine, chlorine, bromine, lower alkyl, lower alkoxy, phenyl, phenoxy, trifluoromethyl, trifluoromethoxy or lower alkoxycarbonyl, or stands for benzyl, phenyl or naphthyl, each of which can be monosubstituted to tetrasubstituted by identical or different lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenylethyl, phenylethoxy, phenylethylthio, phenylethylsulphonyl, fluorine, chlorine, bromine, cyano, trifluoromethyl, trifluoromethoxy, trifluoromethylthio, lower alkoxycarbonyl or by a group of the formula $-NR^1R^2$, where R and R have the abovementioned meaning, or stands for 2,5-dioxo-tetrahydropyrrol, or stands for tetrahydropyranyl, or for dimethyl-tert.butylsilyl, tripropylsilyl or tributylsilyl, or denotes a group of the formula $COR^{16}$, where $R^{16}$ has the abovementioned meaning, and $R^{18}$ and $R^{19}$ are identical or different and denote hydrogen, or denote lower alkyl which is optionally substituted by cyano, fluorine, chlorine or bromine, or denote phenyl, benzyl, thienyl, furyl, pyridyl, pyrimidyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, or D and E together form a ring of the formula

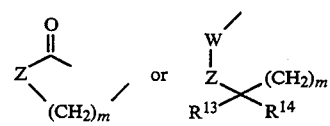

wherein

W—stands for a group of the formula C=O or stands for CH—OH, m—stands for a number 1 or 2, z—stands for O, $CH_2$ or $NHR^{20}$, $R^{13}$ and $R^{14}$ have the abovementioned meaning, and $R^{20}$—stands for hydrogen, lower alkyl, phenyl, benzyl, carbamoyl or lower alkoxycarbonyl, and where in this case D and E are adjacent, X—stands for a group of the formula $-CH=CH-$, R—stands for a group of the formula

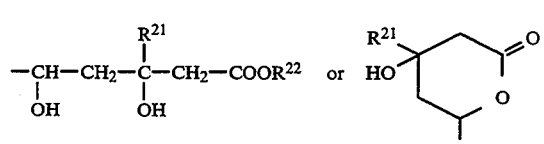

wherein $R^{21}$—denotes hydrogen or lower alkyl, and $R^{22}$—denotes lower alkyl, phenyl or benzyl, or denotes a cation,
and their oxidation products.

Particularly preferred compounds are those of the general formulae (Ia) and (Ib) in which A—stands for thienyl, furyl, pyridyl, pyrimidyl, quinolyl or isoquinolyl, each of which can be substituted by fluorine, chlorine, methyl, methoxy or trifluoromethyl, or stands for phenyl which can be monosubstituted, disubstituted or trisubstituted by identical or different methyl, hydroxymethyl, ethyl, propyl, isopropyl, hydroxy ethyl, hydroxypropyl, butyl, isobutyl, methoxymethyl, ethoxymethyl, propoxymethyl, tert.butyl, methoxy, ethoxy, propoxy, isopropoxy, butoxy, isobutoxy, tert.butoxy, methylthio, ethylthio, propylthio, isopropylthio, methylsulphonyl, ethylsulphonyl, propylsulphonyl, isopropylsulphonyl, phenyl, phenoxy, benzyl, benzyloxy, fluorine, chlorine, bromine, cyano, trifluoromethyl, trifluoromethoxy, methoxycarbonyl, ethoxycarbonyl, propoxycarbonyl, isopropoxycarbonyl, butoxycarbonyl, isobutoxycarbonyl or tert.butoxycarbonyl, stands for methyl, ethyl, propyl, isopropyl, butyl or tert.butyl, B—stands for cyclopropyl, cyclopentyl or cyclohexyl, or stands for methyl, ethyl, propyl, isopropyl, butyl, sec.butyl or tert.butyl, each of which can be substituted by azido, fluorine, chlorine, bromine, cyano, methoxy, ethoxy, propoxy, isopropoxy, butoxy, sec.butoxy, tert.butoxy, methylthio, ethylthio, propylthio, isopropylthio, methylsulphonyl, ethylsulphonyl, propylsulphonyl, isopropylsulphonyl, trifluoromethyl, trifluoromethoxy, methoxycarbonyl, ethoxycarbonyl, butoxycarbonyl, isobutoxycarbonyl, tert.-butoxycarbonyl, benzoyl, acetyl, pyridyl, pyrimidyl, thienyl, furyl, phenyl, phenoxy, phenylthio, phenylsulphonyl, benzyloxy, benzylthio or benzylsulphonyl, D and E—are identical or different and stand for CN, NO$_2$, or stand for hydrogen, cyclopropyl, cyclopentyl or cyclohexyl, or stand for methyl, ethyl, propyl, isopropyl, butyl, isobutyl, tert.butyl, pentyl, isopentyl, hexyl or isohexyl, each of which can be substituted by fluorine, chlorine, bromine, iodine, cyano, hydroxyl, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, trifluoromethyl, trifluoromethoxy, methoxycarbonyl, ethoxycarbonyl, propoxycarbonyl, isopropoxycarbonyl, butoxycarbonyl, isobutoxycarbonyl, tert.butoxycarbonyl, benzoyl, acetyl, ethylcarbonyl, or by a group —NR$^1$R$^2$, where R$^1$ and R$^2$ are identical or different and denote methyl, ethyl, propyl, isopropyl, butyl, isobutyl, tert.butyl, phenyl, benzyl, acetyl, methylsulphonyl, ethylsulphonyl, propylsulphonyl, isopropylsulphonyl or phenylsulphonyl, or by pyridyl, pyrimidyl, pyrazinyl, pyridazinyl, quinoline, isoquinolyl, thienyl, furyl, phenyl, phenoxy, phenylthio, phenylsulphonyl, benzyloxy, benzylthio or benzylsulphonyl, where the heteroaryl and aryl radicals mentioned can be substituted by fluorine, chlorine, methyl, ethyl, propyl, isopropyl, isobutyl, tert.butyl, methoxy, ethoxy, propoxy, isopropoxy, butoxy, isobutoxy, tert.butoxy, trifluoromethyl or trifluoromethoxy, or stand for thienyl, furyl, pyridyl, pyrimidyl, pyrazinyl, tetrazolyl, pyridazinyl, oxazolyl, isooxazolyl, imidazolyl, pyrazolyl, thiazolyl, isothiazolyl, quinolyl, isoquinolyl, benzoxazolyl, benzimidazolyl or benzthiazolyl, where the radicals mentioned can be substituted by fluorine, chlorine, methyl, ethyl, propyl, isopropyl, butyl, isobutyl, tert.butyl, methoxy, ethoxy, propoxy, isopropoxy, butoxy, isobutoxy, tert.-butoxy, phenyl, phenoxy, trifluoromethyl, trifluoromethoxy, methoxycarbonyl, ethoxycarbonyl, isopropoxycarbonyl, propoxycarbonyl, butoxycarbonyl, isobutoxycarbonyl or tert.butoxycarbonyl, or stand for phenyl which can be monosubstituted, disubstituted or trisubstituted by identical or different methyl, ethyl, propyl, isopropyl, butyl, isobutyl, tert.butyl, pentyl, isopentyl, hexyl, methylhydroxy, ethylhydroxy, propylhydroxy, isohexyl, methoxy, ethoxy, propoxy, isopropoxy, butoxy, isobutoxy, methoxymethyl, ethoxymethyl, propoxymethyl, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, phenyl, phenoxy, phenylthio, phenylsulphonyl, benzyl, benzyloxy, benzylthio, benzylsulphonyl, fluorine, chlorine, bromine, cyano, trifluoromethyl, trifluoromethoxy, trifluoromethylthio, methoxycarbonyl, ethoxycarbonyl, propoxycarbonyl, isopropoxycarbonyl, butoxycarbonyl, isobutoxycarbonyl, tert.butoxycarbonyl or by a group —NR$^1$R$^2$, where R$^1$ and R$^2$ have the abovementioned meaning, or for a group of the formula —NR$^3$R$^4$, —COR$^5$ or —CR$^{11}$R$^{12}$—Y wherein R$^3$ and R$^4$ are identical or different and denote hydrogen or denote methyl, ethyl, propyl, isopropyl, tert.butyl, pentyl, isopentyl, hexyl, isohexyl, phenyl, benzyl, or denote a group of the formula —COR$^6$ or —SO$_2$R$^7$, wherein R$^6$—stands for hydrogen, or stands for a group —NHR$^8$, or stands for methoxy, ethoxy, propoxy or isopropoxy, or stands for methyl, ethyl, propyl, isopropyl or butyl, or stands for phenyl, benzyl, benzyloxy, thienyl, furyl, pyridyl, pyrimidyl, quinolyl or isoquinolyl which are optionally substituted by methyl, methoxy, fluorine or chlorine, R$^7$—stands for ethyl, propyl, isopropyl, butyl or isobutyl which are optionally substituted by fluorine, chlorine, methoxycarbonyl, ethoxycarbonyl, propoxycarbonyl, isopropoxycarbonyl, butoxycarbonyl or isobutoxycarbonyl, or stands for phenyl, thienyl, furyl, pyridyl, pyrimidyl, quinolyl or isoquinolyl which are optionally substituted by methyl, ethyl, propyl, isopropyl, methoxy, ethoxy, propoxy or isopropoxy, fluorine or chlorine, and $R^8$—stands for hydrogen, or stands for methyl, ethyl, propyl, isopropyl, butyl, isobutyl, pentyl, isopentyl, hexyl or isohexyl which are optionally substituted by fluorine or chlorine, or stands for phenyl which can be substituted by fluorine, chlorine, methyl or methoxy, $R^5$—denotes hydrogen, cyclohexyl, hydroxyl, methoxy, ethoxy, propoxy, butoxy, isopropoxy, isobutoxy or trimethylsilylethoxy, or stands for $NR^9R^{10}$, wherein $R^9$ and $R^{10}$ are identical or different and denote hydrogen, methyl, ethyl, propyl, isopropyl, butyl, isobutyl or phenyl, or denote a heterocyclic ring of the series comprising piperidine, N-methylpiperazine, N-ethylpiperazine, N-benzylpiperazine or morpholine, and $R^{11}$ and $R^{12}$ are identical or different and stand for hydrogen, or stand for methyl, ethyl, propyl or isopropyl which can optionally be substituted by hydroxyl, fluorine, chlorine, methoxy, ethoxy, methoxycarbonyl or ethoxycarbonyl, or stand for cyclopropyl, cyclopentyl or cyclohexyl, or $R^{11}$ and $R^{12}$ together stand for cyclopropyl, cyclopentyl or cyclohexyl, and Y—denotes a group of the formula $-NR^{13}R^{14}$, $-COR^{15}$, $-SR^{16}$, $-SO-R^{16}$, $-SO_2R^{16}$, $-OR^{17}$ or $-N_3$, where $R^{13}$ and 14 are identical or different, and stand for hydrogen, methyl, ethyl, propyl, isopropyl, butyl, isobutyl, or stand for phenyl which is optionally substituted by fluorine, chlorine, methyl or methoxy, or stand for a group $-COR^{15}$ or $-SO_2R^{16}$, or $R^{13}$ and $R^{14}$ together with the nitrogen atom form a ring from the series comprising piperidine, piperazine, morpholine, morpholine-N-oxide, N-lower alkylpiperazine, benzylpiperazine or phenylpiperazine, $R^{15}$—denotes hydrogen, or denotes a group $-NR^{18}R^{19}$, or denotes methyl, ethyl, propyl, isopropyl, methoxy, ethoxy, propoxy, isopropoxy, or denotes phenyl, benzyl, benzyloxy, thienyl, furyl, pyridyl, pyrimidyl, quinolyl or isoquinolyl which are optionally substituted by methyl, methoxy, fluorine or chlorine, $R^{16}$—denotes methyl, ethyl, propyl, isopropyl, butyl, isobutyl or isopentyl which are optionally substituted by fluorine, chlorine, methoxycarbonyl, ethoxycarbonyl, propoxycarbonyl, isopropoxycarbonyl, butoxycarbonyl or isobutoxycarbonyl, or denotes benzyl, phenyl, naphthyl, thienyl, furyl, pyridyl, pyrimidyl, quinolyl or isoquinolyl which are optionally monosubstituted or polysubstituted by identical or different methyl, ethyl, propyl, isopropyl, methoxy, fluorine or chlorine, or denotes trimethylsilyl or dimethylethylsilyl, denotes a group $-NR^9R^{10}$, where $R^9$ and $R^{10}$ have the abovementioned meaning, $R^{17}$—stands for hydrogen, cyclopropyl, cyclopentyl or cyclohexyl, or stands for methyl, ethyl, propyl, isopropyl, butyl, isobutyl, tert.butyl, pentyl, isopentyl, hexyl or isohexyl, each of which can be substituted by fluorine, chlorine, bromine, cyano, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, trifluoromethyl, trifluoromethoxy, methoxycarbonyl, ethoxycarbonyl, propoxycarbonyl, isopropoxycarbonyl, butoxycarbonyl, isobutoxycarbonyl, tert.butoxycarbonyl, benzoyl, acetyl, ethylcarbonyl, or by a group $-NR^1R^2$, where $R^1$ and $R^2$ are identical or different and denote methyl, ethyl, propyl, isopropyl, butyl, isobutyl, tert.butyl, phenyl, benzyl, acetyl, methylsulphonyl, ethylsulphonyl, propylsulphonyl, isopropylsulphonyl or phenylsulphonyl, or by pyridyl, pyrimidyl, pyrazinyl, pyridazinyl, quinoline, isoquinolyl, thienyl, furyl, phenyl, phenoxy, phenylthio, phenylsulphonyl, benzyloxy, benzylthio or benzylsulphonyl, where the heteroaryl and aryl radicals mentioned can be substituted by fluorine, chlorine, methyl, ethyl, propyl, isopropyl, isobutyl, tert.butyl, methoxy, ethoxy, propoxy, isopropoxy, butoxy, isobutoxy, tert.butoxy, trifluoromethyl or trifluoromethoxy, or stands for thienyl, furyl, pyridyl, pyrimidyl, pyrazinyl, pyridazinyl, oxazolyl, isooxazolyl, imidazolyl, pyrazolyl, thiazolyl, isothiazolyl, quinolyl, isoquinolyl, benzoxazolyl, benzimidazolyl or benzthiazolyl, where the radicals mentioned can be substituted by fluorine, chlorine, methyl, ethyl, propyl, isopropyl, butyl, isobutyl, tert.butyl, methoxy, ethoxy, propoxy, isopropoxy, butoxy, isobutoxy, tert.butoxy, phenyl, phenoxy, trifluoromethyl, trifluoromethoxy, methoxycarbonyl, ethoxycarbonyl, isopropoxycarbonyl, propoxycarbonyl, butoxycarbonyl, isobutoxycarbonyl or tert.butoxycarbonyl, or stands for benzyl or phenyl, each of which can be monosubstituted, disubstituted or trisubstituted by identical or different methyl, ethyl, propyl, isopropyl, butyl, isobutyl, tert.butyl, pentyl, isopentyl, hexyl, isohexyl, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, phenyl, phenoxy, phenylthio, phenylsulphonyl, benzyl, benzyloxy, benzylthio, benzylsulphonyl, fluorine, chlorine, bromine, cyano, trifluoromethyl, trifluoromethoxy, trifluoromethylthio, methoxycarbonyl, ethoxycarbonyl, propoxycarbonyl, isopropoxycarbonyl, butoxycarbonyl, isobutoxycarbonyl, tert.-butoxycarbonyl or by a group $-NR^1R^2$, where $R^1$ and $R^2$ have the abovementioned meaning, or stands for 2,5-dioxo-tetrahydropyrryl, or stands for tetrahydropyranyl, or stands for dimethyl-tert.butylsilyl or trimethylsilyl, or denotes a group —COR$^{16}$, where R$^{16}$ has the abovementioned meaning, and
R$^{18}$ and R$^{19}$ are identical or different and
denote hydrogen, or
denote methyl, ethyl, propyl, isopropyl, butyl, isobutyl, pentyl, isopentyl, hexyl or isohexyl which are optionally substituted by fluorine or chlorine, or
denote phenyl which can optionally be substituted by fluorine, chlorine, methyl or methoxy, or D and E together form a ring of the formula

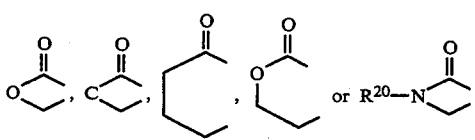

wherein

R$^{20}$—stands for hydrogen, methyl, ethyl, propyl, isopropyl, carbamoyl, methoxycarbonyl or ethoxycarbonyl, X—stands for a group of the formula —CH=CH—, R—stands for a group of the formula

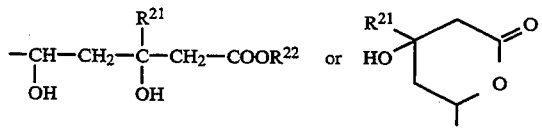

wherein

R$^{21}$—denotes hydrogen, methyl, ethyl, propyl, isopropyl, butyl, isobutyl or tert.butyl, and
R$^{22}$—denotes hydrogen, methyl, ethyl, propyl, isopropyl, butyl, isobutyl, tert.butyl or benzyl, or a sodium, potassium, calcium, magnesium or ammonium ion and their oxidation products.

Very particularly preferred compounds are those of the general formulae (Ia) and (Ib) in which A—stands for thienyl or furyl,
stands for phenyl which can be monosubstituted or disubstituted by identical or different methyl, hydroxymethyl, ethyl, propyl, isopropyl, butyl, isobutyl, tert.butyl, methoxy, ethoxy, propoxy, isopropoxy, phenoxy, benzyloxy, fluorine, chlorine or trifluoromethyl,
stands for methyl, ethyl, propyl or isopropyl, B—stands for cyclopropyl, methyl, ethyl, propyl, isopropyl, butyl, isobutyl or tert.butyl, each of which can be substituted by fluorine, chlorine, methoxy, phenyl or phenoxy, D and E are identical or different and
stand for hydrogen, CN, NO$_2$, cyclopropyl, cyclopentyl or cyclohexyl, or
stand for methyl, ethyl, propyl, isopropyl, butyl, isobutyl, tert.butyl, pentyl, isopentyl, hexyl or isohexyl, each of which can be substituted by azido, fluorine, chlorine, iodine, methoxy, ethoxy, propoxy, isopropoxy, methylthio, ethylthio, methylsulphonyl, ethylsulphonyl, ethoxycarbonyl, propoxycarbonyl, isopropoxycarbonyl or by a group of the formula NR$^1$R$^2$, where R$^1$ and R$^2$ are identical or different and
stand for hydrogen, methyl, ethyl, propyl, isopropyl, phenyl or benzyl,
or by pyridyl, pyrimidyl, quinolyl, thienyl, furyl, phenyl, phenoxy, phenylsulphonyl or benzyloxy which are optionally substituted by fluorine, chlorine, methyl, methoxy, trifluoromethyl or trifluoromethoxy, or
for thienyl, furyl, pyridyl, pyrimidyl, quinolyl, isoquinolyl, benzoxazolyl, tetrazolyl, benzthiazolyl or benzimidazolyl which are optionally substituted by fluorine, chlorine, methyl, ethyl, propyl, isopropyl, methoxy, phenyl, methoxycarbonyl or ethoxycarbonyl, or
stand for phenyl which can be monosubstituted or disubstituted by identical or different methyl, ethyl, propyl, isopropyl, butyl, isobutyl, tert.butoxy, methoxy, ethoxy, propoxy, isopropoxy, methylthio, ethylthio, methylsulphonyl, ethylsulphonyl, phenyl, phenoxy, phenylsulphonyl, benzyloxy, fluorine, chlorine, bromine, cyano, trifluoromethyl, trifluoromethoxy, methoxycarbonyl, ethoxycarbonyl or a group of the formula —NR$^1$R$^2$, where R$^1$ and R$^2$ have the abovementioned meaning, or
stand for a group of the formula —NR$^3$R$^4$, —COR$^5$ or —CR$^{11}$R$^{12}$—Y wherein R$^3$—denotes hydrogen,
R$^4$—denotes hydrogen, methyl, ethyl or propyl, or
denotes a group of the formula —COR$^6$ or —SO$_2$R$^7$, wherein R$^6$—stands for hydrogen, or
stands for a group —NHR$^8$, or
stands for methoxy or ethoxy, or
stands for methyl, ethyl, propyl, or isopropyl,
R$^7$—stands for trifluoromethyl, phenyl, or tolyl,
R$^8$—stands for hydrogen, or
stands for methyl, ethyl, propyl, isopropyl or butyl, or
stands for phenyl,
R$^5$—denotes hydrogen, cyclohexyl, hydroxyl, amino, methylamino, dimethylamino, methoxy, ethoxy or trimethylsilylethoxy, or
stands, for the group NR$^9$R$^{10}$ wherein R$^9$ and R$^{10}$ are identical or different and
denote hydrogen, methyl, ethyl, propyl or phenyl, or
R$^9$ and R$^{10}$ together form a morpholine ring, and
R$^{11}$ and R$^{12}$ denote hydrogen, methyl or ethyl, and
Y—denotes a group of the formula —NR$^{13}$R$^{14}$, COR$^{15}$, —S—R$^{16}$, —SO—R$^{16}$, —SO$_2$R$^{16}$ or —OR$^{17}$, where R$^{13}$ and R$^{14}$ are identical or different, and
stand for hydrogen, methyl, ethyl, propyl, or
stand for a group —COR$^{15}$ or —SO$_2$R$^{16}$ or R$^{13}$ and R$^{14}$, together with the nitrogen atom, form a ring from the series comprising morpholine or morpholine N-oxide, and
R$^{15}$—denotes hydrogen or methyl, or
denotes a group —NR$^{18}$R$^{19}$, or
denotes methyl, ethyl, propyl, methoxy or ethoxy,
R$^{16}$—denotes trifluoromethyl, methyl, ethyl, propyl, isopropyl, butyl, isobutyl, isopentyl or benzyl, or denotes phenyl or naphthyl which is optionally substituted by one or more methyl or chlorine,
denotes trimethylsilyl or dimethylethylsilyl, or
denotes a group —NR⁹R¹⁰,
where
R⁹ and R¹⁰ have the abovementioned meaning,
R¹⁷—stands for hydrogen, cyclopropyl, cyclopentyl or cyclohexyl, or
stands for methyl, ethyl, propyl, isopropyl, butyl, isobutyl, tert.butyl, pentyl, isopentyl, hexyl or isohexyl, each of which can be substituted by fluorine, chlorine, methoxy, ethoxy, propoxy, isopropoxy, methylthio, ethylthio, methylsulphonyl, ethylsulphonyl, ethoxycarbonyl, propoxycarbonyl, isopropoxycarbonyl or by a group of the formula NR¹R²,
where
R¹ and R² are identical or different and
stand for hydrogen, methyl, ethyl, propyl, isopropyl, phenyl or benzyl, or by pyridyl, pyrimidyl, quinolyl, thienyl, furyl, phenyl, phenoxy, phenylsulphonyl or benzyloxy, which are optionally substituted by fluorine, chlorine, methyl, methoxy, trifluoromethyl or trifluoromethoxy, or
stand for thienyl, furyl, pyridyl, pyrimidyl, quinolyl, isoquinolyl, benzoxazolyl, benzthiazolyl or benzimidazolyl which are optionally substituted by fluorine, chlorine, methyl, ethyl, propyl, isopropyl, methoxy, phenyl, methoxycarbonyl or ethoxycarbonyl, or
stands for benzyl or phenyl, each of which can be monosubstituted or disubstituted by identical or different methyl, ethyl, propyl, isopropyl, butyl, isobutyl, tert.butoxy, methoxy, ethoxy, propoxy, isopropoxy, methylthio, ethylthio, methylsulphonyl, ethylsulphonyl, phenyl, phenoxy, phenylsulphonyl, benzyloxy, fluorine, chlorine, bromine, cyano, trifluoromethyl, trifluoromethoxy, methoxycarbonyl, ethoxycarbonyl or a group of the formula —NR¹R²,
where
R¹ and R² have the abovementioned meaning,
stands for 2,5-dioxo-tetrahydropyrryl, or
stands for tetrahydropyranyl, or
stands for dimethyl-tert.butylsilyl or trimethylsilyl, or
denotes a group —COR¹⁶,
where
R¹⁶ has the abovementioned meaning, and
R¹⁸ and R¹⁹ are identical or different and
denote hydrogen, or
denotes methyl, ethyl, propyl, isopropyl, butyl or isobutyl, or
denotes phenyl, or
D and E together form a ring of the formula

X—stands for a group of the formula

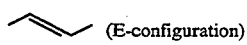
(E-configuration)

and
R—stands for a group of the formula

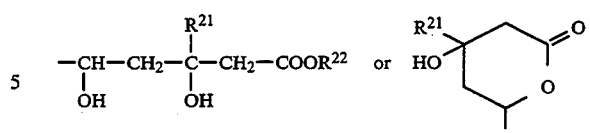

wherein
R²¹—denotes hydrogen and
R²²—denotes hydrogen, methyl or ethyl, or a sodium or potassium ion,
and their oxidation products.

The substituted pyridines of the general formula (I) according to the invention have several asymmetric carbon atoms and can therefore exist in various stereochemical forms. The invention relates both to the individual isomers and to their mixtures.

Depending on the meaning of the group X or the radical R, different stereoisomers result, which are more closely illustrated in the following:

a) If the group —X— stands for a group of the formula —CH=CH—, then the compounds according to the invention can exist in two stereoisomeric forms which can have the E configuration (II) or the Z configuration (III) on the double bond:

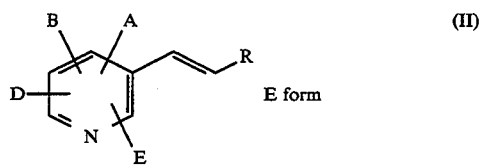
E form (II)

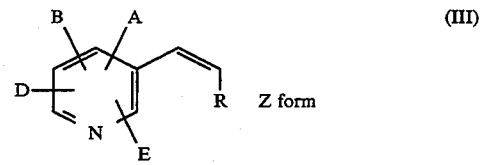
Z form (III)

(A, B, D, E and R have the abovementioned meaning).

Preferred compounds are those of the general formula (I) which have the E configuration (II).

b) If the radical —R— stands for a group of the formula

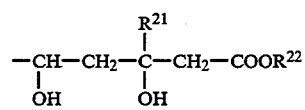

then the compounds of the general formula (I) possess at least two asymmetric carbon atoms, namely the two carbon atoms to which the hydroxyl groups are bonded. Depending on the relative position of these hydroxyl groups to one another, the compounds according to the invention can be present in the erythro configuration (IV) or in the threo configuration (V).

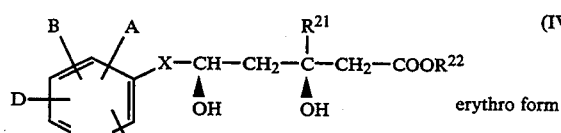

erythro form (IV)

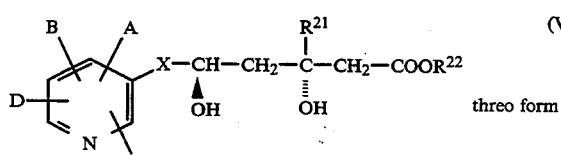

threo form (V)

Two enantiomers in each case again exist of the compounds in the erythro and the threo configuration, namely the 3R,5S-isomer or the 3S,5R-isomer (erythro form) and the 3R,5R-isomer and the 3S,5S-isomer (threo form).

In this case, the isomers having the erythro configuration are preferred, particularly preferably the 3R,5S-isomer and the 3R,5S-3S,5R-racemate.

c) If the radical —R— stands for a group of the formula

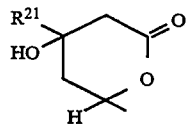

then the substituted pyrroles possess at least two asymmetric carbon atoms, namely the carbon atom to which the hydroxyl group is bonded and the carbon atom to which the radical of the formula

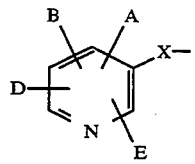

is bonded. Depending on the position of the hydroxyl group to the free valency on the lactone ring, the substituted pyrroles can be present as the cis-lactone (VI) or as the trans-lactone (VII).

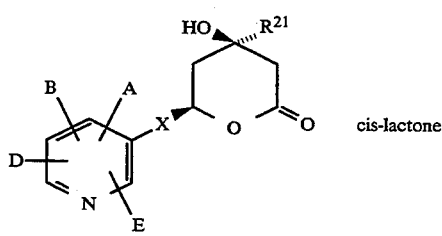

cis-lactone (VI)

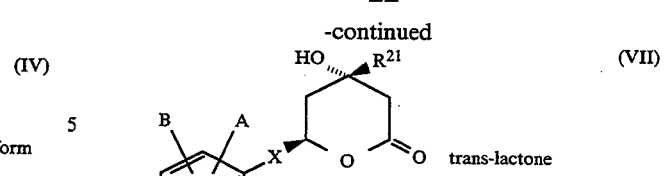

trans-lactone (VII)

Two isomers in each case again exist of the cis-lactone and the trans-lactone, namely the 4R,6R-isomer or the 4S,6S-isomer (cis-lactone), and the 4R,6S-isomer or the 4S,6R-isomer (trans-lactone). Preferred isomers are the trans-lactones. Particularly preferred in this connection is the 4R,6S-isomer (trans) and the 4R,6S-4S,6R-racemate.

For example, the following isomeric forms of the substituted pyrroles may be mentioned:

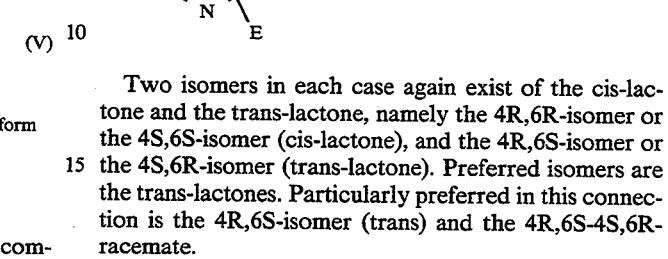

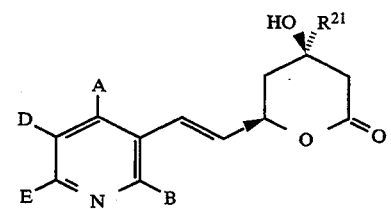

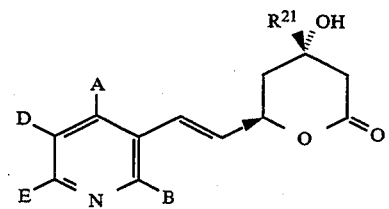

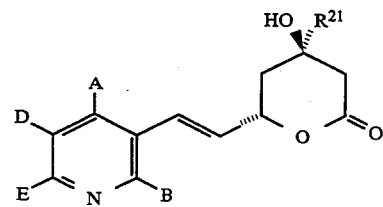

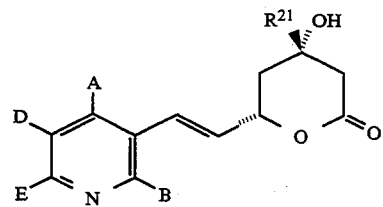

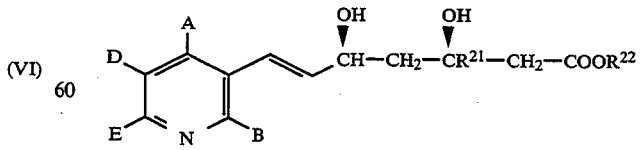

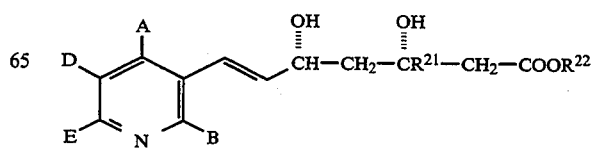

-continued

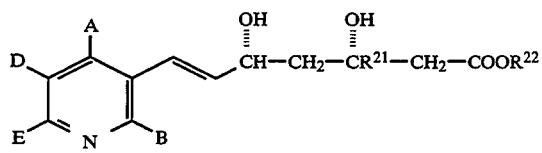

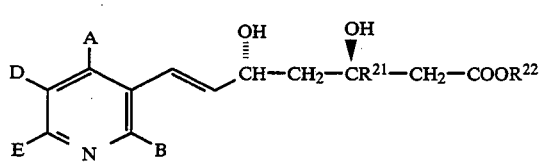

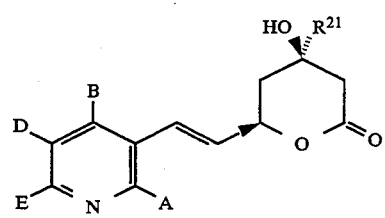

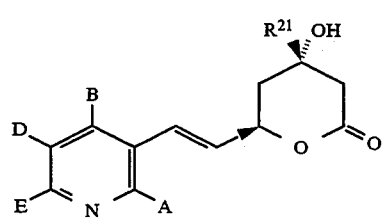

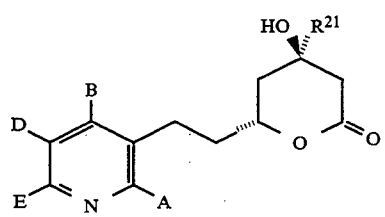

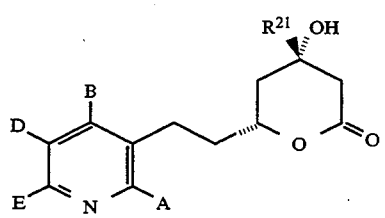

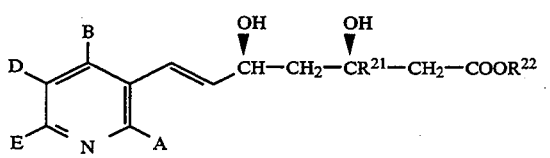

-continued

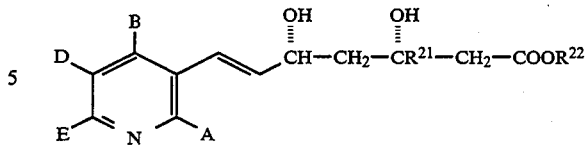

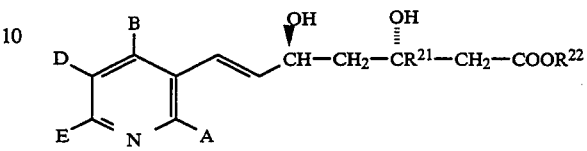

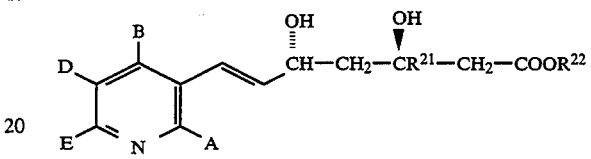

In addition, a process for the preparation of the substituted pyridines of the general formula (I)

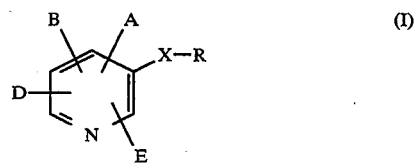         (I)

in which

A, B, D, E, X and R have the abovementioned meaning, has been found, characterized in that ketones of the general formula (VIII)

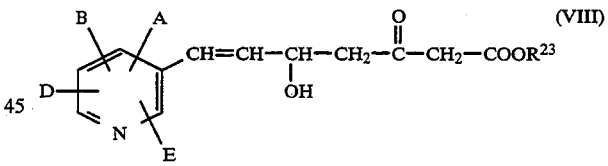         (VIII)

in which

A, B, D and E have the abovementioned meaning, and $R^{23}$—stands for alkyl, are reduced, in the case of the preparation of the acids the esters are hydrolyzed, in the case of the preparation of the lactones, the carboxylic acids are cyclized, in the case of the preparation of the salts either the esters or the lactones are hydrolyzed, in the case of the preparation of the ethylene compounds (X=—CH$_2$—CH$_2$—) the ethene compounds (X=—CH=CH—) are hydrogenated by customary methods, and, if appropriate, isomers are resolved.

The process according to the invention can be illustrated by the following reaction scheme:

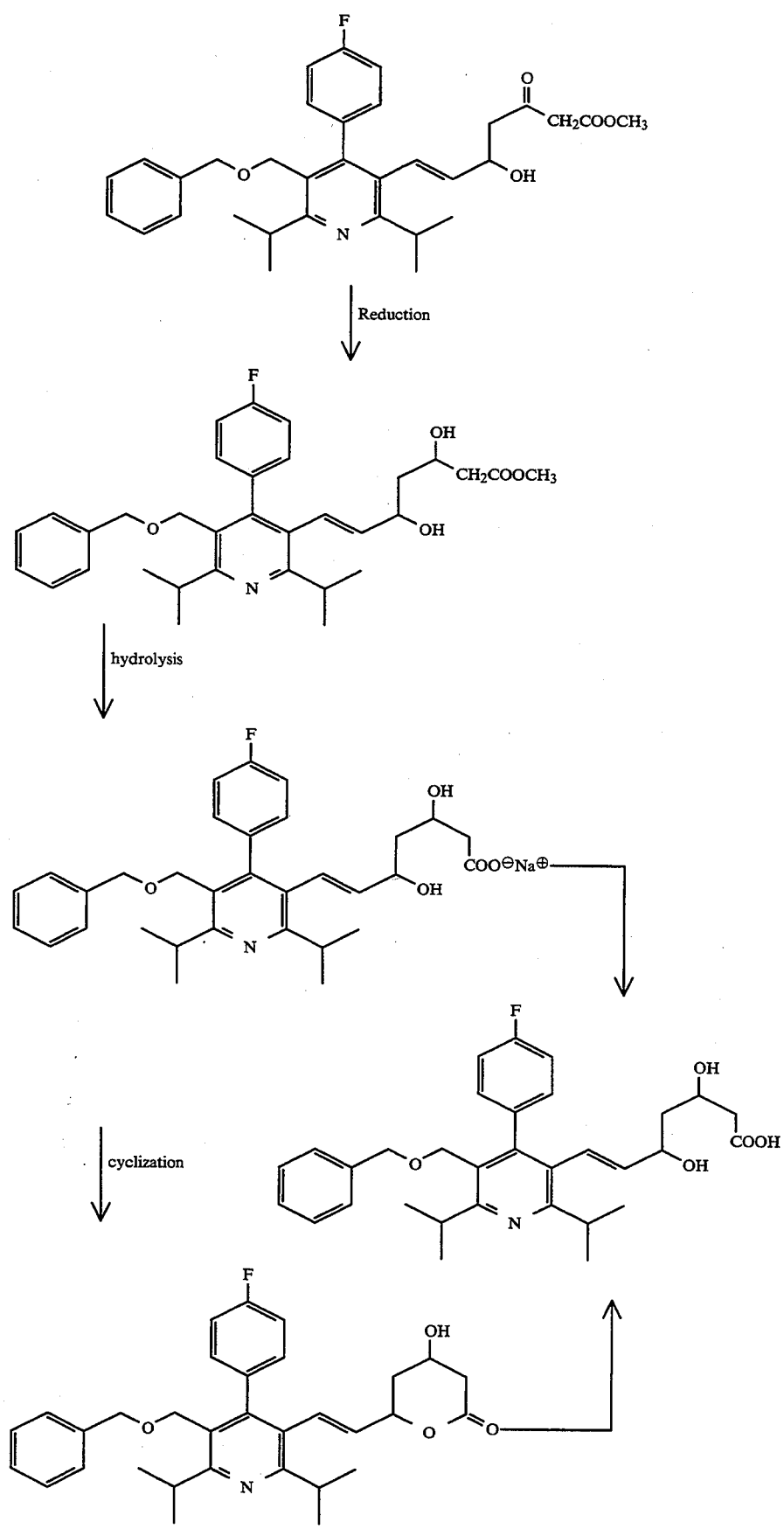

The reduction can be carried out using the customary reductants, preferably using those which are suitable for the reduction of ketones to hydroxyl compounds. Particularly suitable in this case is reduction using metal hydrides or complex metal hydrides in inert solvents, if appropriate in the presence of a trialkyl borane. The reduction is preferably carried out using complex metal hydrides such as, for example, lithium borohydride, sodium borohydride, potassium borohydride, zinc borohydride, lithium trialkyl borohydride, sodium trialkyl borohydrides, sodium cyanoborohydride or lithium aluminum hydride. The reduction is very particularly preferably carried out using sodium borohydride in the presence of triethylborane.

Suitable solvents in this connection are the customary organic solvents which do not change under the reaction conditions. These preferably include ethers such as, for example, diethyl ether, dioxane, tetrahydrofuran or dimethoxyethane, or halogenated hydrocarbons such as, for example, dichloromethane, trichloromethane, tetrachloromethane, 1,2-dichloroethane, or hydrocarbons such as, for example, benzene, toluene or xylene. Likewise, is possible to employ mixtures of the solvents mentioned.

The reduction of the ketone group to the hydroxyl group is particularly preferably carried out under conditions in which the remaining functional groups such as, for example, the alkoxycarbonyl group are not changed. The use of sodium borohydride as a reductant, in the presence of triethyl borane in inert solvents such as, preferably, ethers, is particularly suitable for this.

The reduction in general takes place in a temperature range from −80° C. to +30° C., preferably from −78° C. to 0° C.

The process according to the invention is in general carried out at normal pressure. However, it is also possible to carry out the process at underpressure or at overpressure (for example in a range from 0.5. to 5 bar).

In general, the reductant is employed in an amount from 1 to 2 moles, preferably from 1 to 1.5 moles, relative to 1 mole of the keto compound.

Under the abovementioned reaction conditions, the carbonyl group is in general reduced to the hydroxyl group, without reduction of the double bond to a single bond taking place.

To prepare compounds of the general formula (I), in which X stands for an ethylene grouping, the reduction of the ketones (III) can be carried out under those conditions under which both the carbonyl group and the double bond are reduced.

Moreover, it is also possible to carry out the reduction of the carbonyl group and the reduction of the double bond in two separate steps.

The carboxylic acids in the context of the general formula (I) correspond to the formula (Ic)

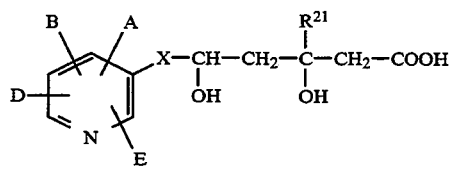

in which

A, B, D, E and $R^{20}$ have the abovementioned meaning.

The carboxylic acid esters in the context of the general formula (I) correspond to the formula (Id)

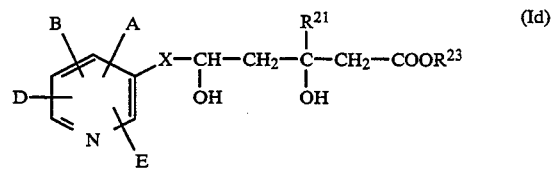

in which

A, B, D, E and $R^{21}$ have the abovementioned meaning, and $R^{23}$—stands for alkyl.

The salts of the compounds according to the invention in the context of the general formula (I) correspond to the formula (Ie)

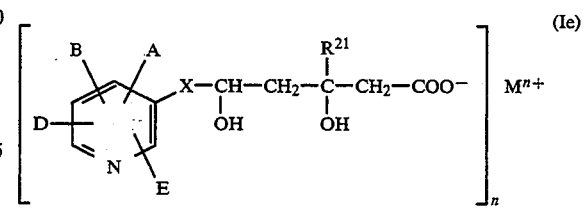

in which

A, B, D, E and R have the abovementioned meaning, and $M^{n+}$ stands for a cation, where n indicates the valency.

The lactones in the context of the general formula (I) correspond to the formula (If)

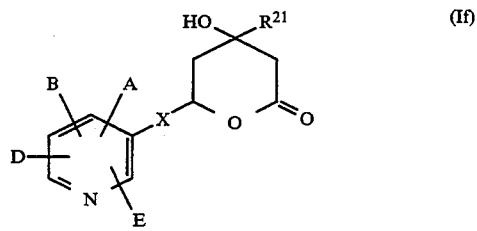

in which

A, B, D, E and R have the abovementioned meaning.

To prepare the carboxylic acids of the general formula (Ic) according to the invention, the carboxylic acid esters of the general formula (Id) or the lactones of the general formula (If) are in general hydrolyzed by customary methods. The hydrolysis in general takes place by treating the esters or the lactones in inert solvents with customary bases, by means of which in general the salts of the general formula (Ie) are first formed, which can subsequently then be converted in a second step into the free acids of the general formula (Ic) by treating with acid.

Bases suitable for the hydrolysis are the customary bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert.butoxide. Sodium hydroxide or potassium hydroxide are particularly preferred.

Suitable solvents for the hydrolysis are water or the organic solvents which are customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. Likewise, it is possible to employ mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at underpressure or at overpressure (for example from 0.5 to 5 bar).

When carrying out the hydrolysis, the base is in general employed in an amount from 1 to 3 moles, preferably from 1 to 1.5 moles, relative to 1 mole of the ester or the lactone. Molar amounts of the reactants are particularly preferably used.

When carrying out the reaction, the salts of the compounds according to the invention (Ie), are formed in the first step, as intermediates which can be isolated. The acids according to the invention (Ic) are obtained by treating the salts (Ie) with customary inorganic acids. These preferably include mineral acids such as, for example, hydrochloric acid, hydrobromic acid, sulphuric acid or phosphoric acid. In this connection, it has proved advantageous in the preparation of the carboxylic acids (Ic) to acidify the basic reaction mixture from the hydrolysis in a second step without isolation of the salts. The acids can then be isolated in a customary manner.

To prepare the lactones of the formula (If) according to the invention, the carboxylic acids according to the invention (Ic) are in general cyclized by customary methods for example by heating the corresponding acids in inert organic solvents, if appropriate in the presence of molecular sieve.

Suitable solvents in this connection are hydrocarbons such as benzene, toluene, xylene, mineral oil fractions, or tetralin or diglyme or triglyme. Benzene, toluene or xylene are preferably employed. Likewise, it is possible to employ mixtures of the solvents mentioned. Hydrocarbons, in particular toluene, are particularly preferably used in the presence of molecular sieves.

The cyclization is in general carried out in a temperature range from −40° C. to +200° C., preferably from −25° C. to +50° C.

The cyclization is in general carried out it normal pressure, but it is also possible to carry out the process at underpressure or at overpressure (for example in a range from 0.5 to 5 bar).

Moreover, the cyclization is also carried out in inert organic solvents, with the aid of cyclizing or water-eliminating agents. In this connection, carbodiimides are preferably used as water-eliminating agents. N,N'-Dicyclohexylcarbodiimide paratoluenesulphonate, N-cyclohexyl-N'-[2-(N''-methylmorpholinium)ethyl]carbodiimide or N-(3-dimethylaminopropyl)-N'-ethylcarbodiimide hydrochloride are preferably employed as carbodiimides.

Suitable solvents in this connection are the customary organic solvents. These preferably include ethers such as diethyl ether, tetrahydrofuran or dioxane, or chlorinated hydrocarbons such as methylene chloride, chloroform or carbon tetrachloride, or hydrocarbons such as benzene, toluene, xylene or mineral oil fractions. Chlorinated hydrocarbons such as, for example, methylene chloride, chloroform or carbon tetrachloride, or hydrocarbons such as benzene, toluene, xylene or mineral oil fractions are particularly preferred. Chlorinated hydrocarbons such as, for example, methylene chloride, chloroform or carbon tetrachloride are particularly preferably employed.

The reaction is in general carried out in a temperature range from 0° C. to +80° C., preferably from +10° C. to +50° C.

When carrying out the cyclization, it has proved advantageous to employ the cyclization methods with the aid of carbodiimides as dehydrating agents.

The resolution of the isomers into the homogeneous stereoisomeric constituents in general takes place by customary methods such as, for example, is described by E. L. Eliel, Stereochemistry of Carbon Compounds, McGraw Hill, 1962. In this case, the resolution of the isomers from the racemic ester step is preferred. Particularly preferably in this connection, the racemic mixture of the trans-lactones (VII) is converted by customary methods by treating either with D-(+)- or L-(−)-α-methylbenzylamine into the diastereomeric dihydroxyamides (Ig)

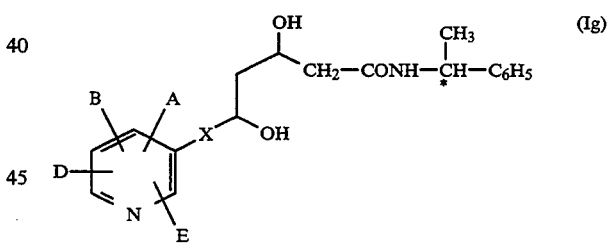

which can subsequently be resolved, as customary, into the individual diastereomers by chromatography or crystallization. Subsequent hydrolysis of the pure diastereomeric amides by customary methods, for example by treating the diastereomeric amides with inorganic bases such as sodium hydroxide or potassium hydroxide water and/or organic solvents such as alcohols, for example methanol, ethanol, propanol or isopropanol, yields the corresponding pure enantiomeric dihydroxy acids (Ic) which can be converted into the pure enantiomeric lactones by cyclization as described above. In general, for the preparation of the compounds of the general formula (I) according to the invention in pure enantiomeric form, the configuration of the final products according to the method described above is dependent on the configuration of the starting materials.

The resolution of isomers is illustrated, for example, in the following scheme:

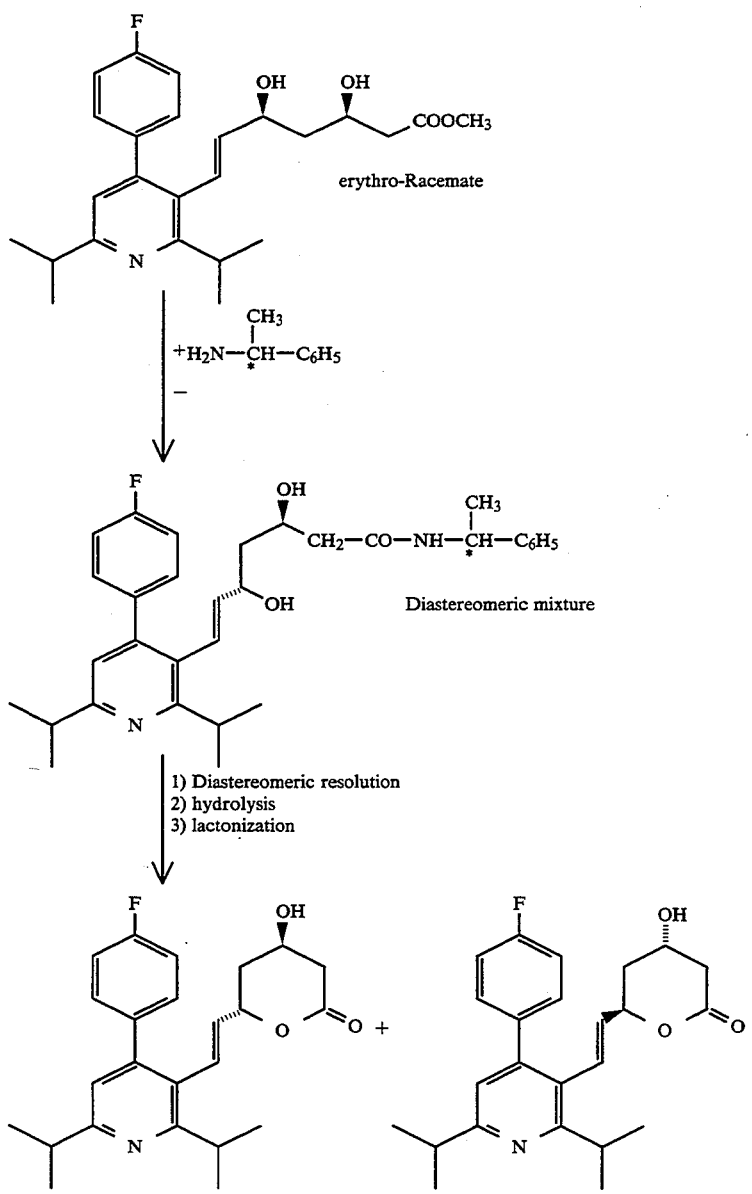

The ketones (VIII) employed as starting materials are new.

A process for the preparation of the ketones of the general formula (VIII) according to the invention

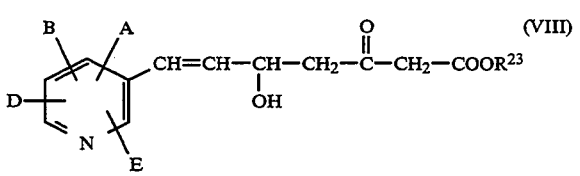

in which

A, B, D, E and $R^{23}$ have the abovementioned meaning, has been found, which is characterized in that aldehydes of the general formula (IX)

(IX)

in which

A, B, D and E have the abovementioned meaning, are reacted in inert solvents with acetoacetates of the general formula (X)

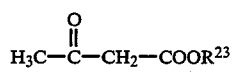

in which

R²³ has the abovementioned meaning, in the presence of bases.

The process according to the invention can, for example, be illustrated by the following reaction scheme:

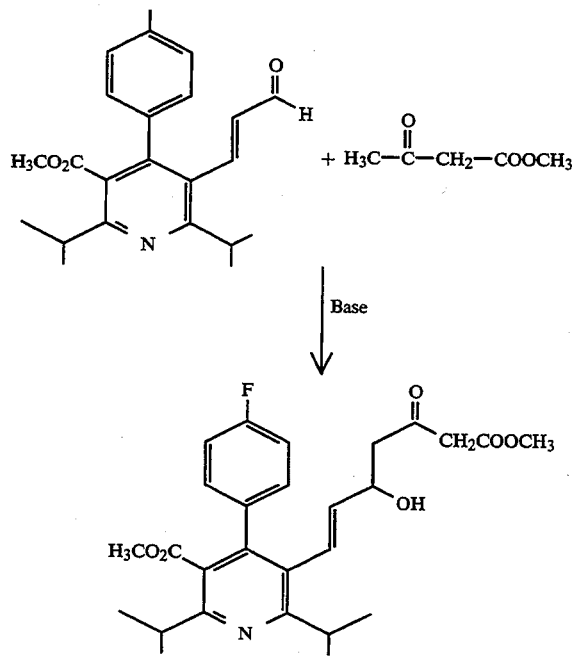

Suitable bases in this connection are the customary strong basic compounds, These preferably include organolithium compounds such as, for example, N-butyllithium, sec.butyllithium, tert.butyllithium or phenyllithium, or amides such as, for example, lithium diisopropylamide, sodium amide or potassium amide, or lithium hexamethyldisilylamide, or alkali metal hydrides such as sodium hydride or potassium hydride. Likewise, it is possible to employ mixtures of the bases mentioned, N-Butyllithium or sodium hydride or a mixture thereof are particularly preferably employed.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. Likewise, it is possible to employ mixtures of the solvents mentioned. Ethers such as diethyl ether or tetrahydrofuran are particularly preferably used.

The reaction is in general carried out in a temperature range from −80° C. to +50° C., preferably from −20° C. to room temperature.

The process is in general carried out at normal pressure, but it is also possible to carry out the process at underpressure or at overpressure, for example in a range from 0.5 to 5 bar.

When carrying out the process, the acetoacetate is in general employed in an amount of 1 to 2, preferably of 1 to 1.5 moles, relative to 1 mole of the aldehyde.

The acetoacetates of the formula (X) employed as starting materials are known or can be prepared by known methods [Beilstein's Handbuch der organischen Chemie (Beilstein's Handbook of Organic Chemistry) III, 632; 438].

Acetoacetates which may be mentioned for the process according to the invention, are, for example: methyl acetoacetate, ethyl acetoacetate, propyl acetoacetate, isopropyl acetoacetate, and the like.

The preparation of the aldehydes of the general formula (IX) employed as starting materials is illustrated by way of example for the compounds of the type (Ia)

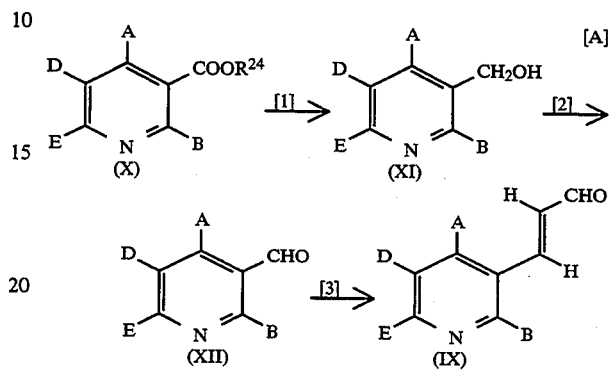

In this connection, according to scheme A, pyridines of the formula (X) in which R²⁴ stands for an alkyl radical having up to 4 carbon atoms are reduced in the first step [1] to the hydroxymethyl compounds (XI) in inert solvents such as ethers, for example diethyl ether, tetrahydrofuran or dioxane, preferably tetrahydrofuran, using metal hydrides as reductants, for example lithium aluminum hydride, sodium cyanoborohydride, sodium aluminum hydride, diisobutylaluminum hydride or sodium bis-(2-methoxyethoxy)-dihydroaluminate, in temperature ranges from −70° C. to +100° C., preferably from −70° C. to room temperature, or from room temperature to 70° C., depending on the reductant used. Preferably, the reduction is carried out using lithium aluminum hydride in tetrahydrofuran in a temperature range from room temperature to 800° C. The hydroxymethyl compounds (XI) are oxidized in a second step [2] by customary methods to the aldehydes (VII). The oxidation can, for example, be carried out using pyridinium chlorochromate, if appropriate in the presence of aluminum, in inert solvents such as chlorinated hydrocarbons, preferably methylene chloride, in a temperature range from 0° C. to 60° C., preferably at room temperature, or else can be carried out using trifluoroacetic acid/dimethyl sulphoxide by the customary methods of Swern oxidation. The aldehydes (XII) are reacted in a third step [3] to give the aldehydes (IX) using diethyl 2-(cyclohexylamino)-vinylphosphonate in the presence of sodium hydride in inert solvents such as ethers, for example diethyl ether, tetrahydrofuran or dioxane, preferably in tetrahydrofuran, in a temperature range from −20° C. to +40° C., preferably from −5° C. to room temperature.

The pyridines of the formula (X) employed as starting materials in this connection are in this case in general obtained according to scheme B by oxidation of dihydropyridines (XIII) which again, depending on the meaning of the radical D, have been obtained by variation of the corresponding functional groups. The dihydropyridines employed as starting materials in this connection are known or can be prepared by known methods [EP-A 88,276, DE-A 2,847,236]. The oxidation of the dihydropyridines (XIII) to the pyridines (X) can be carried out, for example, using chromic oxide in glacial acetic acid in a temperature range from −20° C. to +150° C., preferably at reflux temperature, or using 2,3-dichloro-5,6-dicyano-p-benzoquinone as an oxidant in inert solvents such as chlorinated hydrocarbons, preferably methylene chloride, in a temperature range from 0° C. to +100° C., preferably at room temperature.

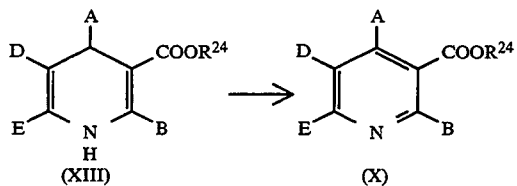

The variation of the radical D is illustrated by some examples in the following reaction equations:

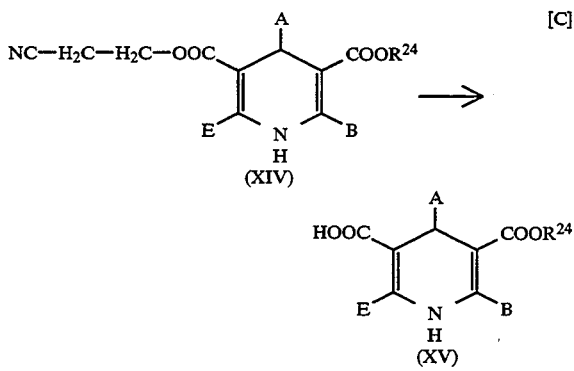

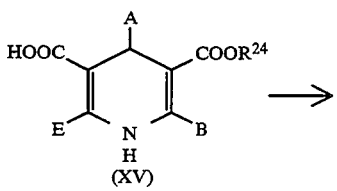

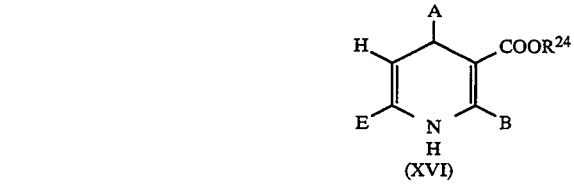

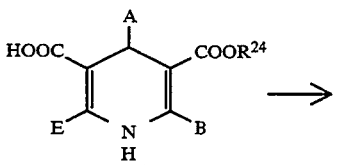

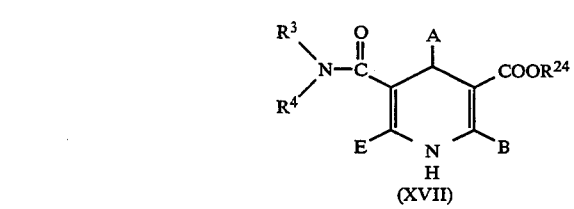

The dihydropyridines (XIV) can be hydrolyzed to the dihydropyridinecarboxylic acids (XV), for example by reaction with an alkali metal hydroxide in dimethoxyethane at room temperature. The dihydropyridinecarboxylic acids (XV) can be decarboxylated to the dihydropyridines (XVI), for example, by heating to 200° C. in diethylene glycol. In addition, the dihydropyridinecarboxylic acids (XV) can be reacted to give the dihydropyridinecarboxylic acid amides (XVII) by known methods, for example by reaction with dicyclohexylcarbodiimide.

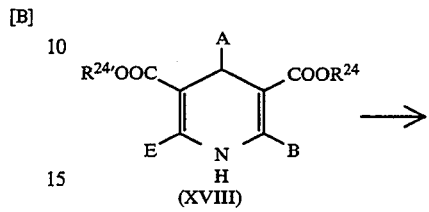

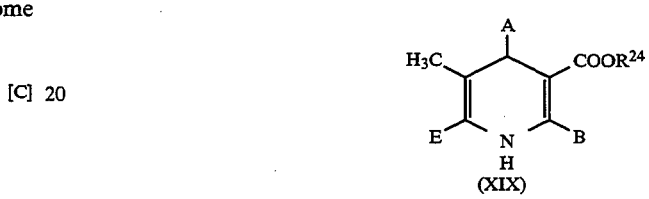

The dihydropyridines (XVIII) can be reduced to the dihydropyridines (XIX) using customary reductants, for example by reaction of lithium aluminum hydride in tetrahydrofuran, at room temperature or at boiling point.

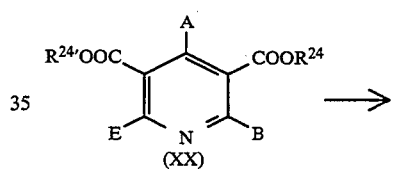

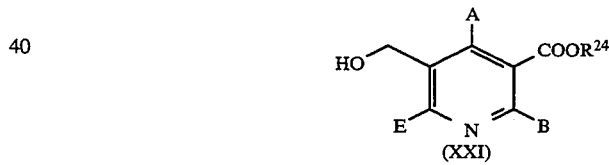

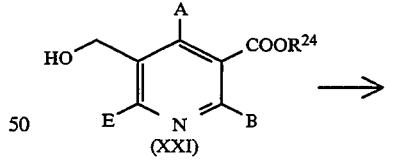

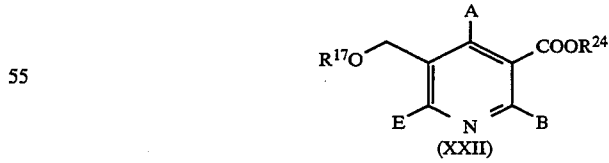

The pyridines (XX), which can be prepared from the dihydropyridines (XVIII) by oxidation as described above, can be reduced to the pyridines (XXI) by suitable reductants, such as, for example, lithium aluminum hydride, diisobutylaluminum hydride or sodium bis-(2-methoxyethoxy)-dihydroaluminate in inert solvents, such as, for example, tetrahydrofuran.

The pyridines (XXI) can be reacted to give the pyridines (XXII) by known methods, for example by reaction with an alkyl or benzyl halide in the presence of a base, such as, for example, sodium hydride or for example by reaction with a trialkylsilyl halide or an acid halide in the presence of a base such as imidazole, pyridine or triethylamine. The hydroxyl group of the pyridines (XXI) can be converted into a leaving group by known methods, for example by reaction with trifluoromethanesulphonic anhydride, thionyl chloride or methanesulphonyl chloride in the presence of a base. The leaving group can then be exchanged for a nucleophile by known methods.

The compounds of the general formula (I) according to the invention possess useful pharmacological properties and can be employed in medicaments. In particular, they are inhibitors of 3-hydroxy-3-methyl-glutaryl-coenzyme A (HGM-CoA) reductase and are consequently inhibitors of cholesterol biosynthesis. They can therefore be employed for the treatment of hyperlipoproteinaemia, lipoproteinaemia or atherosclerosis. The active compounds according to the invention additionally cause a lowering of the cholesterol content in the blood.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration from about 0.5 to 98% by weight, preferably 1 to 90% by weight, of the total mixture, i.e. in amounts which are sufficient to achieve the dosage range indicated.

The formulations are prepared, for example, by extending the active compounds using solvents and/or excipients, if appropriate using emulsifiers and/or dispersants, where, for example, in the case of the use of water as a diluent, if appropriate organic solvents can be used as auxiliary solvents.

Auxiliary solvents which may be mentioned as examples are: water, non-toxic organic solvents, such as paraffins (for example=mineral oil fractions), vegetable oils (for example groundnut/sesame oil), alcohols (for example: ethyl alcohol, glycerol), excipients, such as for example ground natural minerals (for example kaolins, argillaceous earths, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkyl sulphonates and aryl sulphonates), dispersants (for example lignin, sulphite waste liquors, methylcellulose, starch and polyvinylpyrrolidone) and lubricants (for example magnesium stearate, talc, stearic acid and sodium lauryl sulphate).

The administration takes place in a customary manner, preferably orally, parenterally, perlingually or intravenously. In the case of oral use, tablets can, of course, also contain additions, such as sodium citrate, calcium carbonate and dicalcium phosphate together with various additives, such as starch, preferably potato starch, gelatine and the like in addition to the excipients mentioned. Furthermore, lubricants, such as magnesium stearate, sodium lauryl sulphate and talc can additionally be used for tabletting. In the case of aqueous suspensions, various flavor improvers or colourants can be added to the active compounds in addition to the auxiliaries mentioned above.

In the case of parenteral use, solutions of the active compounds can be employed using suitable liquid excipients.

In general, has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this, it can be necessary to deviate from the amounts mentioned, depending on the body weight or the type of application route, on individual behavior. towards the medicament, the manner of its formulation and the point in time or interval at which administration takes place.

Thus, in some cases it may be sufficient to manage with less than the minimum amount previously mentioned, whereas in other cases the upper limit mentioned must be exceeded. In the case of the administration of larger amounts, it can be advisable to divide these into several individual doses over the day.

PREPARATION EXAMPLES

EXAMPLE 1

(E/Z)-4-Carboxyethyl-5-(4-fluorophenyl)-2-methyl-pent-4-en-3-one

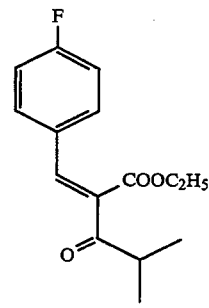

62 g (0.5 mol) of 4-fluorobenzaldehyde and 79 g (0.5 mol) of ethyl isobutyrylacetate are initially introduced into 300 ml of isopropanol and a mixture of 2.81 ml (28 mmol) of piperidine and 1.66 ml (29 mmol) of acetic acid in 40 ml of isopropanol is added. The mixture is allowed to stir for 48 hours at room temperature and is concentrated in vacuo, and the residue is distilled in a high vacuum.

B.p. 0.5 mm: 127° C. Yield: 108.7 g (82.3% theory)

EXAMPLE 2

Diethyl 1,4-dihydro-2,6-diisopropyl-4-(4-fluorophenyl)pyridine-3,5-dicarboxylate

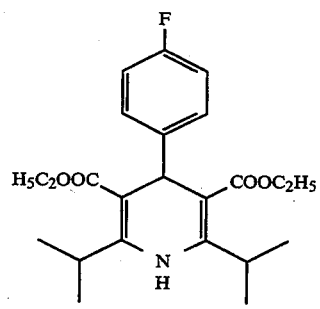

98 g (0.371 mol) of the compound from Example 1 are heated to reflux for 18 h with 58.3 g (0.371 mol) of ethyl 3-amino-4-methyl-pent-2-enoate in 300 ml of ethanol. The mixture is cooled to room temperature, the solvent is evaporated off in vacuo and the unreacted starting materials are distilled off in a high vacuum at 130° C. The remaining syrup is stirred with n-hexane and the deposited precipitate is filtered off with suction, washed, with n-hexane and dried in a desiccator.

Yield: 35 g (23.4% of theory) $^1$H-NMR (CDCl$_3$): $\delta$=1.1–1.3 (m, 18H); 4.05–4.25 (m, 6H); 5.0 (s, 1H); 6.13 (s, 1H); 6.88 (m, 2H); 7.2 (m, 2H) ppm.

EXAMPLE 3

Diethyl 2,6-diisopropyl-4-(4-fluorophenyl)-pyridine-3,5-dicarboxylate

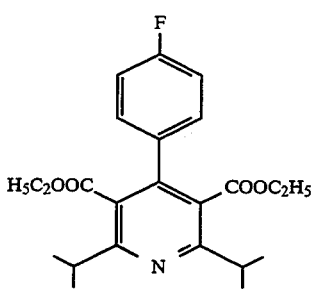

3.8 g (16.4 mmol) of 2,3-dichloro-5,6-dicyano-p-benzoquinone are added to a solution of 6.6 g (16.4 mmol) of the compound from Example 2 in 200 ml of methylene chloride p.a. and the mixture is stirred for 1 h at room temperature. It is then filtered with suction over kieselguhr, and the methylene chloride phase is extracted three times with 100 ml of water each time and dried over magnesium sulphate. After concentrating in vacuo, the residue is chromatographed on a column (100 g of silica gel 70–230 mesh, $\phi$3.5 cm, using ethyl acetate/petroleum ether 1:9).

Yield: 5.8 g (87.9% of theory) $^1$H-NMR (CDCl$_3$): $\delta$=0.98 (t, 6H); 1.41 (d, 12H); 3.1 (m, 2H); 4.11 (q, 4H); 7.04 (m, 2H); 7.25 (m, 2H) ppm.

EXAMPLE 4

Ethyl 2,6-diisopropyl-4-(4-fluorophenyl)-5-hydroxymethyl-pyridine-3-carboxylate

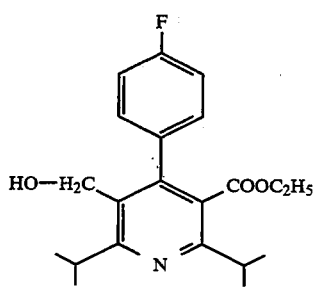

21 ml (80.5 mmol) of a 3.5 molar solution of sodium bis-(2-methoxyethoxy)-dihydroaluminate in toluene are added under nitrogen to a solution of 9.2 g (23 mmol) of the compound from Example 3 in 100 ml of dry tetrahydrofuran at −10° C. to −5° C. and the mixture is stirred for 5 h at room temperature. After cooling to 0° C., 100 ml of water are cautiously added dropwise and the mixture is extracted three times using 100 ml of ethyl acetate each time. The combined organic phases are washed with saturated sodium chloride solution, dried over magnesium sulphate and evaporated in vacuo. The residue is chromatographed on a column (200 g of silica gel 70–230 mesh, $\phi$4.5 cm, using ethyl acetate/petroleum ether 3:7).

Yield: 7.2 g (87.2% of theory) $^1$H-NMR (CDCl$_3$): $\delta$=0.95 (t, 3H); 1.31 (m, 12H); 3.05 (m, 1H); 3.48 (m, 1H), 3.95 (q, 2H); 4.93 (d, 2H); 7.05–7.31 (m, 4H) ppm.

EXAMPLE 5

Ethyl 5-(tert.butyldimethylsilyloxymethyl)-2,6-diisopropyl-4-(4-fluorophenyl)-pyridine-3-carboxylate

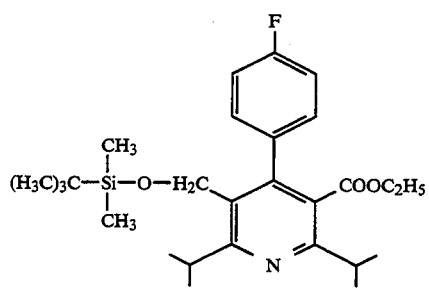

2.1 g (13.8 mmol) of tert.butyldimethylsilyl chloride, 1.8 g (27.5 mmol) of imidazole and 0.05 g of 4-dimethylaminopyridine are added at room temperature to a solution of 4.5 g (12.5 mmol) of the compound from Example 4 in 50 ml of dimethylformamide. The mixture is stirred overnight at room temperature, 200 ml of water are added and the mixture is adjusted to pH 3 using 1N hydrochloric acid. The mixture is extracted three times using 100 ml of ether each time, and the combined organic phases are washed once with saturated sodium chloride solution, dried over magnesium sulphate and concentrated in vacuo. The residue is chromatographed on a column (150 g of silica gel, 70–230 mesh, $\phi$4 cm, using ethyl acetate/petroleum ether 1:9).

Yield: 4.2 g (73.7% of theory) $^1$H-NMR (CDCl$_3$): $\delta$=0.0 (s, 6H); 0.9 (s, 9H); 1.02 (t, 3H); 1.35 (m, 12H); 3.1 (m, 1H); 3.47 (m, 1H); 4.03 (q, 2H); 4.4 (s, 2H); 7.05–7.40 (m, 4H) ppm.

EXAMPLE 6

3-(tert.Butyldimethylsilyloxymethyl)-2,6-diisopropyl-4-(4-fluorophenyl)-5-hydroxymethyl-pyridine

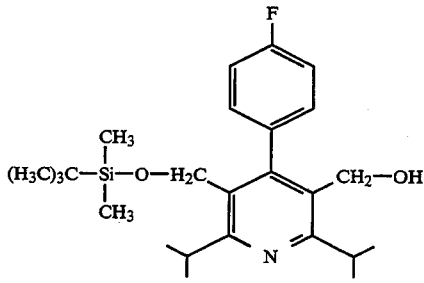

9.2 ml (32.2 mmol) of a 3.5 molar solution of sodium bis-(2-methoxyethoxy)-dihydroaluminate in toluene are added under nitrogen to a solution of 4.2 g (9.2 mmol) of the compound from Example 5 in 100 ml of dry tetrahydrofuran at 0° C. and the mixture is stirred overnight at room temperature. After cooling to 0° C., 100 ml of water are cautiously added dropwise and the mixture is extracted three times using 100 ml of ethyl acetate each time. The combined organic phases are washed once with saturated sodium chloride solution, dried over magnesium sulphate and concentrated in vacuo. The residue is chromatographed on a column (100 g of silica gel 70–230 mesh, φ3.5 cm, using ethyl acetate/petroleum ether 2:8).

Yield: 2.4 g (60% of theory) $^1$H-NMR (CDCl$_3$): δ=0.2 (s, 6H); 1.11 (s, 9H); 1.6 (m, 12H); 3.7 (m, 2H); 4.55 (s, 2H); 4.65 (d, 2H); 7.35–7.55 (m, 4H) ppm.

EXAMPLE 7

5-(tert.Butyldimethylsilyloxymethyl)-2,6-diisopropyl)-4-(4-fluorophenyl)-pyridine-3-carbaldehyde

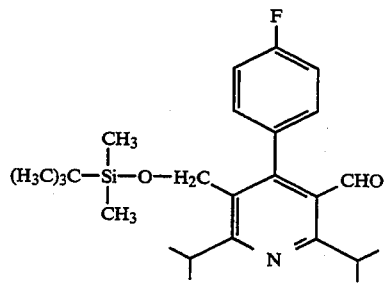

1.24 g (12.4 mmol) of neutral alumina and 2.7 g (12.4 mmol) of pyridinium chlorochromate are added to a solution of 2.7 g (6.2 mmol) of the compound from Example 6 in 50 ml of methylene chloride and the mixture is stirred for 1 h at room temperature. It is filtered over kieselguhr and washed with 200 ml of methylene chloride. The methylene chloride phase is concentrated in vacuo and the residue is chromatographed on a column (100 g of silica gel 70–230 mesh, φ3.5 cm, using ethyl acetate/petroleum ether 1:9).

Yield: 2 g (77% of theory) $^1$H-NMR (CDCl$_3$): δ=0.0 (s, 6H); 0.9 (s, 9H); 1.35 (m, 12H); 3.5 (m, 1H); 3.9 (m, 1H); 4.38 (s, 2H); 7.15–7.35 (m, 4H); 9.8 (s, 1H) ppm.

EXAMPLE 8

(E)-3-[5-tert.Butyldimethylsilyloxymethyl-2,6-diisopropyl-4-(4-fluorophenyl)-pyrid-3-yl]-prop-2-enal

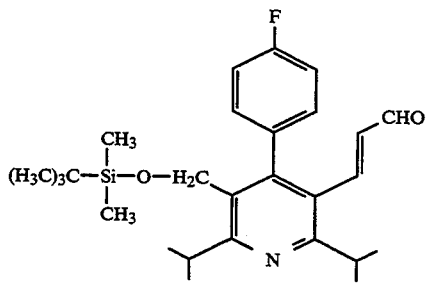

1.6g (6 mmol) of diethyl 2-(cyclohexylamino)vinylphosphonate dissolved in 30 ml of dry tetrahydrofuran are added dropwise under nitrogen to a suspension of 180 mg (6 mmol) of 80% strength sodium hydride in 15 ml of dry tetrahydrofuran at −5° C. After 30 minutes, 2 g (4.7 mmol) of the compound from Example 7 in 40 ml of dry tetrahydrofuran are added dropwise at the same temperature and the mixture is warmed to reflux for 30 minutes. After cooling to room temperature, the batch is added to 200 ml of ice-cold water and extracted three times using 100 ml of ethyl acetate each time. The combined organic phases are washed with saturated sodium chloride solution and dried over magnesium sulphate. After concentrating in vacuo, the residue taken up in 70 ml of toluene, a solution of 0.9 g (7 mol) of oxalic acid dihydrate in 30 ml of water is added and the mixture is heated to reflux for 30 minutes. After cooling to room temperature, the phases are separated, and the organic phase is washed with saturated sodium chloride solution, dried over magnesium sulphate and concentrated in vacuo. The residue is chromatographed on a column (100 g of silica gel 70–230 mesh φ3.5 cm, using ethyl acetate/petroleum ether 1:9).

Yield: 2 g (95% of theory) $^1$H-NMR (CDCl$_3$): δ=0.0 (s, 6H); 0.9 (s, 9H); 1.38 (m, 12H); 3.36 (m, 1H); 3.48 (m, 1H); 4.48 (s, 2H); 6.03 (dd, 1H); 7.12–7.35 (m, 5,H); 9.45 (d, 1H) ppm.

EXAMPLE 9

Methyl (E)-7-[5-tert.butyldimethylsilyloxymethyl-2,6-diisopropyl-4-(4-fluorophenyl)-pyrid-3-yl]-5-hydroxy-3-oxohept-6-enoate

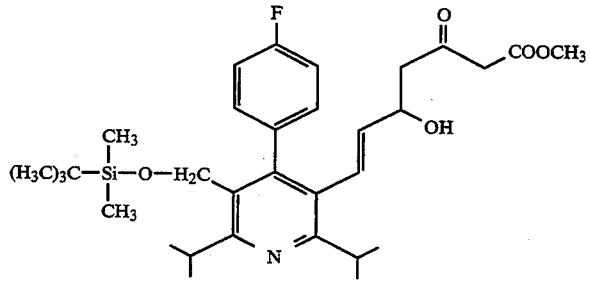

1.02 g (8.8 mmol) of methyl acetate in 5 ml of dry tetrahydrofuran are added dropwise under nitrogen to a suspension of 330 mg (11 mmol) of 80% strength sodium hydride in 30 ml of dry tetrahydrofuran at −5° C. After 15 min, 5.5 ml (8.8 mmol) of 15% strength butyllithium in n-hexane ere added dropwise at the same temperature and the mixture is stirred for 15 minutes. Subsequently, 2 g (4.4 mmol) of the compound from Example 8 dissolved in 20 ml of dry tetrahydrofuran are added dropwise and the mixture is stirred for 30 minutes at −5° C. 3 ml of 50% strength acetic acid are cautiously added to the reaction solution, and the mixture is diluted using 100 ml of water and extracted three times using 100 ml of ether each time. The combined organic phases are washed twice with saturated sodium hydrogen carbonate solution and once with saturated sodium chloride solution, dried over magnesium sulphate and concentrated in vacuo. The residue is chromatographed on a column (100 g of silica gel 70–230 mesh, φ3 cm, using ethyl acetate/petroleum ether 3:7).

Yield: 1.9 g (84.4% of theory) $^1$H-NMR (CDCl$_3$): δ=0.0 (s, 6H); 0.9 (s, 9H); 1.35 (m, 12H); 2.5 (m, 2H); 3.32 (m, 1H); 3.45 (m, 1H); 3.48 (s, 2H); 3.81 (s, 3H) ; 4.35 (s, 2H); 4.55 (m, 1H); 5.32 (dd, 1H); 6.42 (d, 1H); 7.15 (m, 4H) ppm.

EXAMPLE 10

Methyl erythro-(E)-7-[5-tert.butyldimethylsilyloxymethyl-2,6-diisopropyl-4-(4-fluorophenyl)-pyrid-3-yl]-3,5-dihydroxy-hept-6-enoate

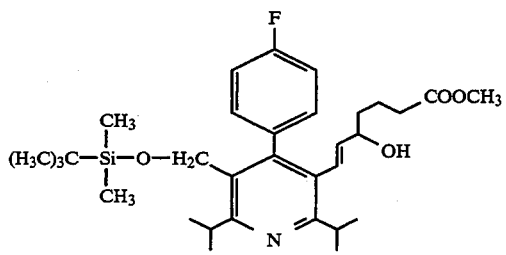

4.5 ml (4.5 mmol) of 1M triethylborane solution in tetrahydrofuran are added at room temperature to a solution of 1.9 g (3.7 mmol) of the compound from Example 9 in 40 ml of dry tetrahydrofuran, air is passed through the solution for 5 minutes and it is cooled to an internal temperature of −30° C. 160 mg (4.5 mmol) of sodium borohydride and, slowly, 3 ml of methanol are added, the mixture is stirred for 30 minutes at −30° C. and a mixture of 12 ml of 30% strength hydrogen peroxide and 25 ml of water is then added. The temperature is allowed to rise to 0° C. during the course of this and the mixture is stirred for 30 minutes more. The mixture is extracted three times using 70 ml of ethyl acetate each time, and the combined organic phases are washed once each with saturated sodium hydrogen carbonate solution and saturated sodium chloride solution, dried over magnesium sulphate and concentrated in vacuo. The residue is chromatographed on a column (80 g of silica gel 230–400 mesh, $\phi$2.5 cm, using ethyl acetate/petroleum ether 4:6).

Yield: 1.5 g (78.9% of theory) $^1$H-NMR (CDCl$_3$): $\delta$=0.0 (s, 6H); 0.9 (s, 9H); 1.35 (m, 12H); 1.5 (m, 2H); 2.5 (m, 2H); 3.35 (m, 1H); 3.45 (m, 1H); 3.8 (s, 3H); 4.15 (m, 1H); 4.45 (m, 3H); 5.32 (dd, 1H); 6.38 (d, 1H); 7.05–7.25 (m, 4H) ppm.

EXAMPLE 11

Methyl erythro-(E)-7-[2,6-diisopropyl-4-(4-fluorophenyl)-5-hydroxymethyl-pyrid-3-yl]-3,5-dihydroxy-hept-6-enoate

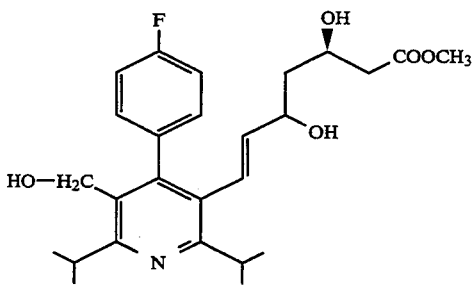

15 ml of 0.1N hydrochloric acid are added to 8.4 g (14.6 mmol) of the compound from Example 10 dissolved in 135 ml of methanol and the mixture is stirred for 4 days at room temperature. The mixture is concentrated in vacuo, and the residue is taken up in dichloromethane and dried several times with saturated sodium hydrogen carbonate solution. The organic phase is dried over magnesium sulphate and concentrated in vacuo, and the residue is chromatographed on a column (silica gel 70–230 mesh, using ethyl acetate/petroleum ether 4:6).

Yield: 3.5 g (52.5% of theory) $^1$H-NMR (CDCl$_3$): $\delta$=1.25 (m, 6H); 1.33 (d, 6H); 1.40 (m, 2H); 2.41 (m, 2H); 3.30 (m, 1H); 3.45 (m, 1H); 3.71 (s, 3H); 4.07 (m, 1H); 4.28 (m, 1H); 4.39 (d, 2H); 5.25 (dd, 1H); 6.30 (d, 1H); 7.08 (m, 4H) ppm.

EXAMPLE 12

Ethyl 5-benzyloxymethyl-2,6-diisopropyl-4-(4-fluorophenyl)-pyridine-3-carboxylate

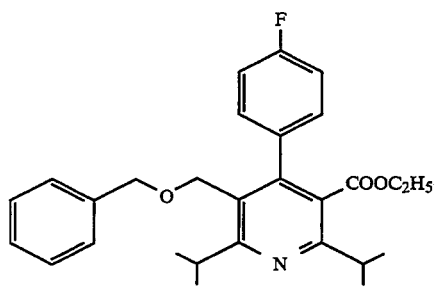

4.5 g (12.5 mmol) of the compound from Example 4 in 50 ml of dimethylformamide are added dropwise under nitrogen to a suspension of 414 mg (13.8 mmol) of 80% strength sodium hydride in 20 ml of dimethylformamide at 0° C. and the mixture is stirred for 30 minutes at the same temperature. Subsequently, 1.65 ml (13.8 mmol) of benzyl bromide in 20 ml of dimethylformamide are added dropwise and the mixture is stirred for a further 3 h at room temperature. The mixture is poured into 300 ml of water at 0° C. and extracted three times using 150 ml of ether each time. The combined organic phases are washed once with saturated sodium chloride solution, dried over magnesium sulphate and concentrated in vacuo. The residue is chromatographed on a column (100 g of silica gel 70–230 mesh, $\phi$3.5 cm, using ethyl acetate/petroleum ether 1:10).

Yield: 2.6 g (46.4% of theory) $^1$H-NMR (CDCl$_3$): $\delta$=0.95 (t, 3H); 1.3 (m, 12H); 3.05 (m, 1H); 3.38 (m, 1H); 3.97 (q, 2H); 4.2 (s, 2H); 4.38 (s, 2H); 7.02 (m, 2H); 7.25 (m, 7H) ppm.

EXAMPLE 13

3-Benzyloxymethyl-2,6-diisopropyl-4-(4-fluorophenyl)-5-hydroxymethyl-pyridine

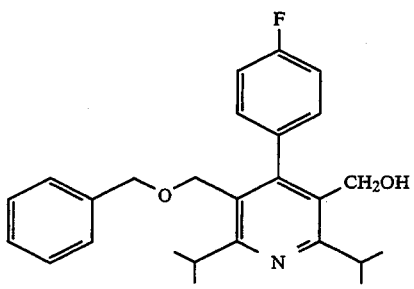

2.5 g (5.5 mmol) of the compound from Example 12 are reacted analogously to Example 6.

Yield: 1.5 g (68% of theory) $^1$H-NMR (CDCl$_3$): δ=1.3 (m, 12H); 3.35 (m, 1H); 3.45 (m, 1H); 4.13 (s, 2H); 4.35 (m, 4H); 7.08 (m, 2H); 7.25 (m, 7H) ppm.

EXAMPLE 14

5-Benzyloxymethyl-2,6-diisopropyl-4-(4-fluorophenyl)-pyridine-3-carbaldehyde

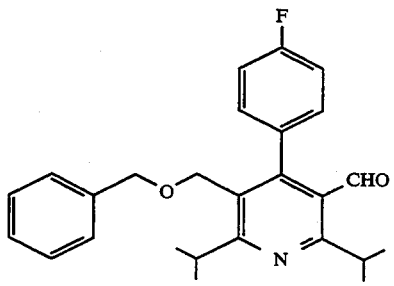

1.5 g (3.6 mmol) of the compound from Example 13 are reacted analogously to Example 7.

Yield: 1.1 g (75.9% of theory) $^1$H-NMR (CDCl$_3$): δ=1.3 (m, 12H); 3.4 (m, 1H); 3.85 (m, 1H); 4.18 (s, 2H); 4.38 (s, 2H); 7.05–7.35 (m, 9H); 9.75 (s, 1H) ppm.

EXAMPLE 15

(E)-3-[5-Benzyloxymethyl-2,6-diisopropyl-4-(4-fluorophenyl)-pyrid-3-yl]-prop-2-enal

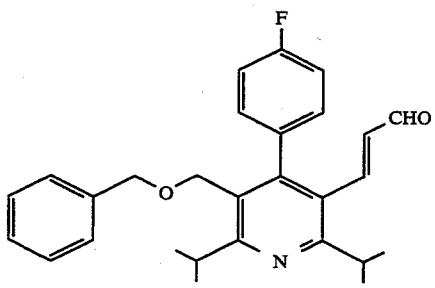

1.1 g (2.7 mmol) of the compound from Example 14 are reacted analogously to Example 8.

Yield: 450 mg (38.8% of theory) $^1$H-NMR (CDCl3): δ=1.35 (m, 12H); 3.35 (m, 1H); 3.42 (m, 1H); 4.21 (s, 2H); 4.41 (s, 2H); 6.0 (dd, 1H); 7.05–7.4 (m, 10H); 9.38 (d, 1H) ppm.

EXAMPLE 16

Methyl (E)-7-[5-benzyloxymethyl-2,6-diisopropyl-4-(4-fluorophenyl)-pyrid-3-yl]-5-hydroxy-3-oxo-hept-6-enoate

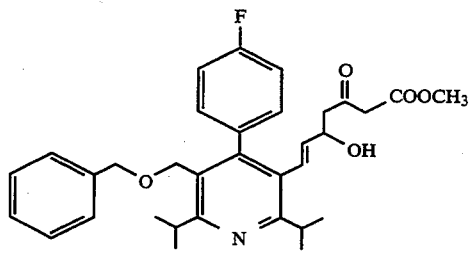

431 mg (1 mmol) of the compound from Example 15 are reacted analogously to Example 9.

Yield: 300 mg (54.8% of theory)

EXAMPLE 17

Methyl erythro-(E)-7-[3-benzyloxymethyl-2,6-diisopropyl-4-(4-fluorophenyl)-pyrid-5-yl]-3,5-dihydroxy-hept-6-enoate

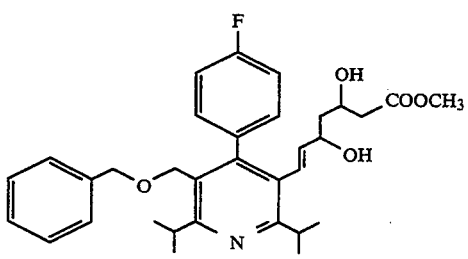

300 mg (0.55 mmol) of the compound from Example 16 are reacted analogously to Example 10.

Yield: 180 mg (59.6% of theory) $^1$H-NMR (CDCl$_3$): δ=1.2–1.35 (m, 12H); 1.4 (m, 2H); 2.41 (m, 2H); 3.3 (m, 2H); 3.73 (s, 3H); 4.05 (m, 1H); 4.15 (s, 2H); 4.28 (m, 1H); 4.35 (s, 2H); 5.25 (dd, 1H); 6.3 (d, 1H); 6.95–7.35 (m, 9H) ppm.

EXAMPLE 18

3-Ethyl 5-methyl 1,4-dihydro-4-(4-fluorophenyl)-2-isopropyl-6-methyl-pyridine-3,5-dicarboxylate

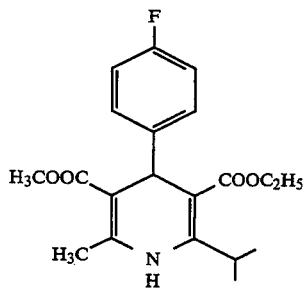

15 g (56.8 mmol) of the compound from Example 1 and 6.5 g (56.8 mol) of methyl 3-aminocrotonate are heated at reflux for 20 h in 150 ml of ethanol. The mixture is cooled, filtered and concentrated in vacuo. The residue is chromatographed on a column (250 g of silica gel 70–230 mesh, φ4.5 cm, using ethyl acetate/petroleum ether 3:7).

Yield: 13.6 g (66.3% of theory) $^1$H-NMR (CDCl$_3$): δ=1.2 (m, 9H); 3.65 (s, 3H); 4.12 (m, 3H); 4.98 (s, 1H); 5.75 (s, 1H); 6.88 (m, 2H); 7.25 (m, 2H) ppm.

EXAMPLE 19

3-Ethyl 5-methyl 4-(4-fluorophenyl)-2-isopropyl-6-methylpyridine-3,5-dicarboxylate

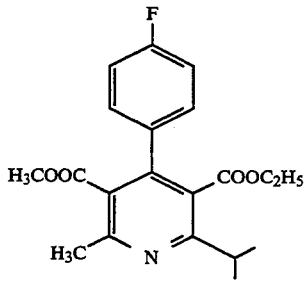

13.5 g (37.4 mmol): of the compound from Example reacted analogously to Example 3.

Yield: 9.5 g (70.9% of theory) $^1$H-NMR (CDCl$_3$): δ=0.98 (t, 3H); 1.31 (d, 6H); 2.6 (s, 3H); 3.11 (m, 1H); 3.56 (s, 3H); 4.03 (q, 2H); 7.07 (m, 2H); 7.25 (m, 2H) ppm.

EXAMPLE 20

Ethyl 4-(4-fluorophenyl)-5-hydroxymethyl-2-isopropyl-6-methylpyridine-3-carboxylate

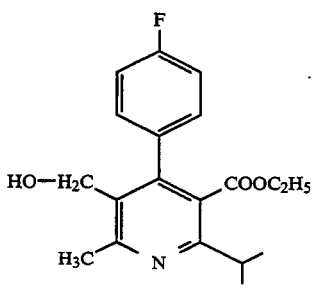

26.5 ml (92.75 mmol) of a 3.5 molar solution of sodium bis-(2-methoxyethoxy)-dihydroaluminate in toluene are added under nitrogen to a solution of 9.5 g (26.5 mmol) of the compound from Example 19 in 200 ml of absolute tetrahydrofuran at 0° C. and the mixture is stirred for 30 minutes at room temperature. After cooling again to 0° C., 200 ml of water are cautiously added dropwise and the mixture is extracted three times using 150 ml of ethyl acetate each time. The combined organic phases are washed once with saturated sodium chloride solution, dried over magnesium sulphate and concentrated in vacuo. The residue is chromatographed on a column (200 g of silica gel 70–230 mesh, φ4.5 cm, using ethyl acetate/petroleum ether 2:8).

Yield: 4.2 g (48.2% of theory) $^1$H-NMR (CDCl$_3$): δ=0.98 (t, 3H); 1.3 (d, 6H); 2.73 (s, 3H); 3.05 (m, 1H); 3.98 (q, 2H); 4.45 (d, 2H); 7.1 (m, 2H); 7.25 (m, 2H) ppm.

EXAMPLE 21

(E/Z)-4-Carboxyethyl-5-(4-fluoro-3-phenoxyphenyl)-2-methyl-pent-4-en-3-one

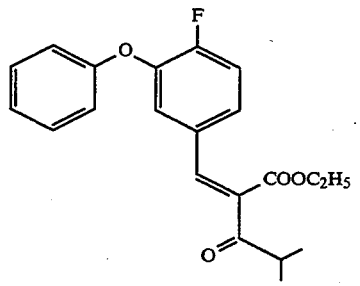

49 g (0.31 mol) of ethyl isobutyrylacetate and 67 g (0.31 mol) of 3-phenoxy-4-fluorobenzaldehyde are initially introduced in 300 ml of isopropanol and a mixture of 1.81 ml (18 mmol) of piperidine and 1.06 ml (18.6 mmol) of acetic acid in 30 ml of isopropanol is added. The mixture is stirred overnight at room temperature, then concentrated in vacuo and dried in a high vacuum.

Yield: 110 g (was employed without further purification in Example 22).

EXAMPLE 22

Diethyl 1,4-dihydro-2,6-diisopropyl-4-(4-fluoro-3-phenoxyphenyl)-pyridine-3,5-dicarboxylate

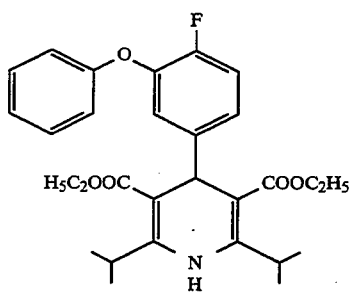

30 g (84.3 mmol) of the compound from Example 21 and 13.2 g (84.3 mmol) of ethyl 3-amino-4-methyl-pent-2-enoate are heated to reflux in 150 ml of ethanol overnight. The mixture is cooled to 0° C., and the deposited precipitate is filtered off, washed with petroleum ether and dried in a desiccator.

Yield: 18.4 g (44.2% of theory) $^1$H-NMR (CDCl$_3$): δ=1.05–1.25 (m, 18H); 4.05–4.2 (m, 6H); 4.95 (s, 1H); 6.03 (s, 1H); 6.85–7.1 (m, 6H); 7.3 (m, 2H) ppm.

EXAMPLE 23

Diethyl 2,6-diisopropyl-4-(4-fluoro-3-phenoxyphenyl)pyridine-3,5-dicarboxylate

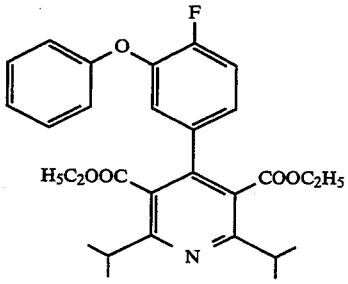

18.4 g (37.2 mmol) of the compound from Example 22 are reacted analogously to Example 3.

Yield: 17.6 g (96% of theory) $^1$H-NMR (CDCl$_3$): δ=1.05 (t, 6H); 1.29 (d, 12H); 3.08 (m, 2H); 4.05 (q, 4H); 6.95–7.35 (m, 8H) ppm.

EXAMPLE 24

Ethyl 2,6-diisopropyl-4-(4-fluoro-3-phenoxy-phenyl)-5-hydroxymethyl-pyridine-3-carboxylate

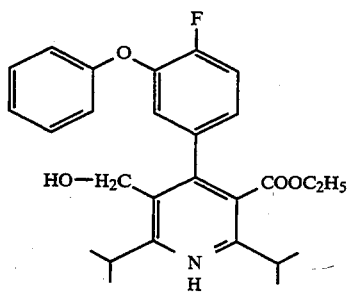

10 g (20.3 mmol) of the compound from Example 23 are reacted analogously to Example 4.

Yield: 4.9g (59.0% of theory) $^1$H-NMR (CDCl$_3$): δ=1.07 (t, 3H); 1.3 (m, 12H); 3.04 (m, 1H); 3.47 (m, 1H); 4.05 (m, 2H) 4.45 (s, 2H); 6.95–7.4 (m, 8H) ppm.

EXAMPLE 25

Methyl 2-cyanoethyl 1,4-dihydro-2,6-dimethyl-4-(4-fluorophenyl)-pyridine-3,5-dicarboxylate

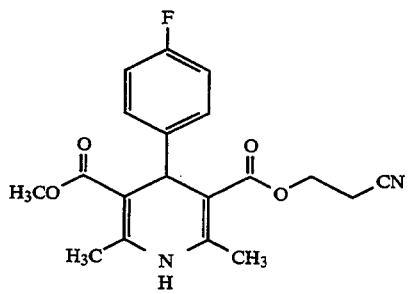

15.4 g (0.1 mol) of 2-cyanoethyl 3-aminocrotonate, 12.4 g (0.1 mol) of p-fluorobenzaldehyde and 11.6 g of methyl acetoacetate are heated overnight under reflux in 150 ml of ethanol. After removing the solvent on a rotary evaporator, the residue is taken up in ethyl acetate, washed with water, dried and 33.8 g of crude product are obtained after removing the solvent in vacuo.

Crude yield: 94.4% of theory $^1$H-NMR (DMSO): δ=1.15 (tr, 3H, CH$_3$); 2.3 (m, 6H, CH$_3$); 2.75 (m, 2H, CH$_2$CN); 3.55 (s, 3H, OCH$_3$); 4.15 (m, 2H, OCH$_2$); 4.9 (m, 1H, p-FC$_6$H$_4$—CH); 6.9–7.3 (m, 4H, aromatic —H); 8.8, 9.0 (2s, 1H, NH) ppm.

EXAMPLE 26

Methyl 1,4-dihydro-2,6-dimethyl-4-(4-fluorophenyl)-pyridine-3,5-dicarboxylate

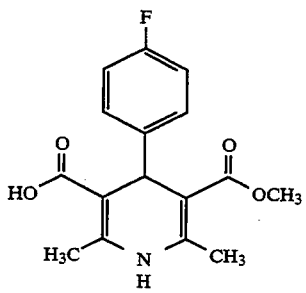

33.8 g of crude product from Example 25 are added to a solution of 12 g (0.3 mol) of sodium hydroxide in 300 ml of water/150 ml of 1,2-dimethoxyethane. The suspension warms and forms a clear solution. After stirring at 25° C. overnight, 100 ml of water are added, and the mixture is washed three times with dichloromethane, adjusted to pH 1 using dilute hydrochloric acid and the tacky deposited product is extracted using dichloromethane. After drying and concentrating the solvent in vacuo, 25.8 g of crude product are obtained.

Crude yield: 84.5% of theory $^1$H-NMR (DMSO): δ=2.25 (s, 6H, CH$_3$); 3.55 (s, 3H, OCH$_3$); 4.85 (broad s, 1H, FC$_6$H$_4$—CH); 6.9–7.3 (m, 4H, aromatic-H); 8.85 (broad s, 1H, NH); 1.7 (broad, 1H, COOH) ppm.

EXAMPLE 27

Methyl 1,4-dihydro-2,6-dimethyl-4-(4-fluorophenyl)-pyridine-3-carboxylate

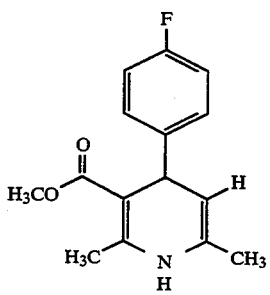

12.5 g (41 mmol) of crude product from Example 26 are suspended in 90 ml of bis-(2-hydroxyethyl)-ether(diglycol) and the mixture is heated to a bath temperature of 200° C., a vigorous evolution of gas taking place. After evolution of gas is complete, the now clear solution is quickly cooled and washed with 500 ml of water/500 ml of ether, the aqueous phase is washed twice with ether and the combined ether phases are washed with water, 1N sodium hydroxide solution and water and dried. After removing the solvent on a rotary evaporator, 8.7 g of crude product are obtained.

Crude yield: 81.2% of theory

EXAMPLE 28

Methyl 2,6-dimethyl-4-(4-fluorophenyl)-pyridine-3-carboxylate

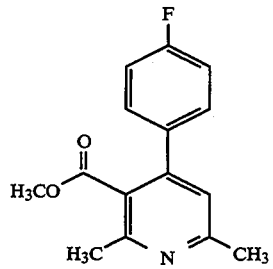

8.6g (33 mmol) of crude product from Example 27 and 3.3 g of chromium(VI) oxide are heated under reflux for 1 hour in 90 ml of glacial acetic acid. The solvent is then removed on the rotary evaporator, ethyl acetate/petroleum ether 1:1 is added to the residue and undissolved material is filtered off with suction. The mother liquor is concentrated in vacuo and chromatographed over 500 g of silica gel using ethyl acetate/petroleum ether 1:1.

Yield: 1.45 g (16.3% of theory) $^1$H-NMR (CDCl$_3$): $\delta$=2.6 (s, 6H, CH$_3$) 3.65 (s, 3H, OCH$_3$); 7.0 (s, 1H, pyridine-H); 7.1-7.4 (m, 4H, aromatic-H) ppm.

EXAMPLE 29

2,6-Dimethyl-4-(4-fluorophenyl)-3-hydroxymethyl-pyridine

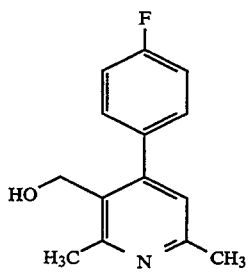

5.3 ml (5.3 mmol) of diisobutylaluminum hydride (1M in toluene) are added under nitrogen at −78° C. to 1.35 g (5.2 mmol) of the compound from Example 28 in 25 ml of absolute tetrahydrofuran and, after warming to 25° C., the mixture is hydrolyzed using 20% strength potassium hydroxide solution. The aqueous phase is washed with ethyl acetate and the combined organic phases are dried. After evaporating in vacuo, 1.12 g of crude product are obtained.

Yield: 93% of theory $^1$H-NMR (CD$_3$OD): $\delta$=2.5 (S, 3H, CH$_3$); 2.7 (s, 3H, CH$_3$); 4.5 (s, 2H, CH$_2$OH); 4.6 (s, OH); 7.0 (s, 1H, pyridine-H); 7.1-7.6 (m, 4H, aromatic-H) ppm.

EXAMPLE 30

2,6-Dimethyl-4-(4-fluorophenyl)-pyridine-3-carbaldehyde

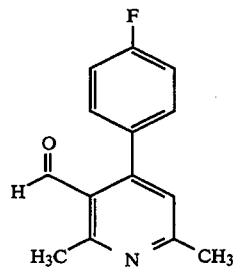

1.5 g (7 mmol) of pyridinium dichromate are added in portions to 1.0 g (4.3 mmol) of the compound from Example 29 in 20 ml of dichloromethane, the mixture is stirred for 2 h at 250° C., after concentrating chromatographed over 150 g of silica gel using dichloromethane/methanol 10:1 and 0.71 g of product are obtained.

Yield: 72% of theory $^1$H-NMR (DMSO): $\delta$=2.5 (s, 3H, CH$_3$); 2.7 (s, 3H, CH$_3$); 7.2 (s, 1H, pyridine-H); 7.3-7.6 (m, 4H, aromatic-H); 9.95 (s, 1H, CHO) ppm.

EXAMPLE 31

(E)-3-[2,6-Dimethyl-4-(4-fluorophenyl)-pyrid-3-yl]-prop-2-enal

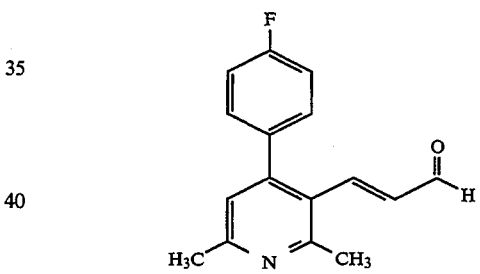

778 mg (3.2 mmol) of diethyl [2-(cyclohexylamino)-vinyl]-phosphate in 3 ml of tetrahydrofuran are added under a nitrogen atmosphere to 75.5 mg (3.2 mmol) of sodium hydride in 3 ml of absolute tetrahydrofuran during the course of 15 minutes at 0° C., the mixture is stirred for 15 minutes at 0° C. and a solution of 0.6 g (2.6 mmol) of the compound from Example 30 in 3 ml of acetonitrile/3 ml of dimethylformamide is added dropwise. After stirring for 1 h at 0° C. and 30 minutes at 25° C., the mixture is hydrolyzed using 50 ml of water, washed with ether (3×50 ml), and the organic phase is dried, concentrated in vacuo, taken up in 8 ml of toluene and stirred with 1.2 g (13.5 mmol) of oxalic acid/20 ml of water for 1.5 h at 60° C.-80° C. under a nitrogen atmosphere. After cooling, the mixture is adjusted to pH 10 using 2N sodium hydroxide solution and washed four times with ether, and the ether phase is dried, concentrated in vacuo and chromatographed over 100 g of silica gel using dichloromethane/methanol 30:1.

Yield: 0.3 g (45% of theory) $^1$H-NMR (CDCl$_3$): $\delta$=2.6 (s, 6H, CH$_3$); 6.2 (dd, 1H, CH-CHO); 6.9-7.4 (m, 5H, aromatic-H); 7.45 (d, 1H, CH=CH-CHO); 9.5 (d, 1H, CHO) ppm.

EXAMPLE 32

Methyl (E)-7-[2,6-dimethyl-4-(4-fluorophenyl)-pyrid-3-yl]-5-hydroxy-3-oxo-hept-6-enoate

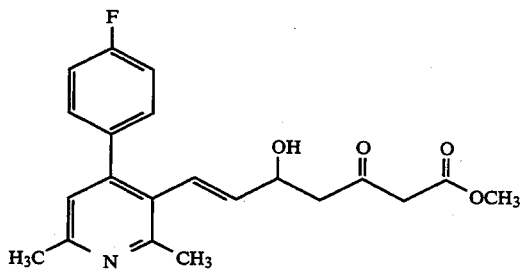

82.2 μl (0.76 mmol) of methyl acetoacetate are added dropwise at 0° C. under a nitrogen atmosphere to 18.5 mg (0.8 mmol) of sodium hydride in 1 ml of tetrahydrofuran. After 15 minutes, 0.55 ml (0.77 mmol) of n-butyllithium (1.5M in hexane) is added dropwise at 0° C., the mixture is stirred for 15 minutes at 0° C. and 180 mg (0.7 mmol) of the compound from Example 31 are added dropwise in 3 ml of tetrahydrofuran. After 1 h, the mixture is hydrolyzed using saturated ammonium chloride solution and washed three times using dichloromethane, and the organic phases are dried and 0.25 g of oil are obtained after removing the solvent in vacuo.

Crude yield: 95.5% of theory $^1$H-NMR (CDCl$_3$): δ=2.55, 2.58 (2s, 6H, CH$_3$); 2.6 (2H, CH$_2$); 3.45 (s, 2H, CH$_2$CO$_2$); 3.75 (s, 3H, OCH$_3$); 4.6 (m, 1H, CHOH); 5.45 (dd, 1H, CH-CHOH); 6.5 (d, 1H, CH=CH-CHOH); 6.9 (s, 1H, pyridine-H); 7.0–7.4 (m, 4H, aromatic-H) ppm.

EXAMPLE 33

Methyl erythro-(E)-7-[2,6-dimethyl-4-(4-fluorophenyl)pyridin-3-yl]-3,5-dihydroxy-hept-6-enoate

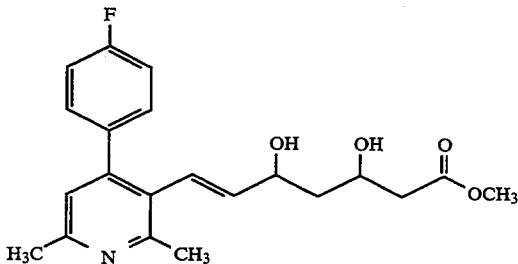

Air is blown through a solution of 0.25 g (0.67 mmol) of the compound from Example 32 and 0.81 ml (0.81 mmol) of triethylborane (1M in tetrahydrofuran) for 5 minutes, 30.6 (0.81 mol) of sodium borohydride and, slowly, 0.55 ml of methanol are added at −30° C., the mixture is stirred for 30 minutes at −30° C., a mixture of 4.7 ml of water and 2.16 ml of 30% strength hydrogen peroxide solution is added in such a way that the temperature does not exceed 0° C., the mixture is diluted after 30 minutes using water, washed three times with ethyl acetate, the organic phase is washed with sodium hydrogen carbonate solution and dried, the solvent is removed in vacuo, the residue is chromatographed over 75 g of silica gel using ethyl acetate and 0.11 g of product is obtained.

Yield: 43.7% of theory $^1$H-NMR (CDCl$_3$): δ=2.45 (m, 2H, CH$_2$CO$_2$); 2.5, 2.58 (2s, 6H, CH$_3$); 3.75 (s, 3H, OCH$_3$); 4.2, 4.4 (2m, 2H, CHOH); 5.45 (dd, 1H, CH-CHOH); 6.55 (d, 1H, CH=CH-OH); 6.4 (s, 1H; pyridine-H); 7.0–7.4 (m, 4H, aromatic-H) ppm.

EXAMPLE 34

5-(2-Cyanoethyl)-3-ethyl-1,4-dihydro-2-(4-fluorophenyl)-4-isopropyl-6-methyl-pyridine-3,5-dicarboxylate

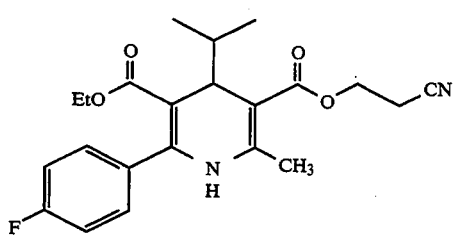

Analogously to Example 25, 32.6 g of crude product are obtained from 2.75 g (0.1 mol) of ethyl isopropylidene-4-fluoro-benzoylacetate and 15.4 g (0.1 mol) of 2-cyanoethyl 3-aminocrotonate.

Crude yield: 93.6% of theory $^1$H-NMR (CDCl$_3$): δ=0.7–1.3 (m, 9H, CH$_3$); 2.3, 2.35 (2s, 3H, CH$_3$); 2.75 (m, 2H, CH$_2$CN); 3.9–4.4 (m, 5H, CHCH$_3$, CH$_2$O); 5.6, 5.7, 6.1, 6.2 (4s, 1H, CH); 7.0–8.0 (m, 4H, aromatic-H) ppm.

EXAMPLE 35

3-Ethyl 1,4-dihydro-2-(4-fluorophenyl)-4-isopropyl-6-methyl-pyridine-3,5-dicarboxylate

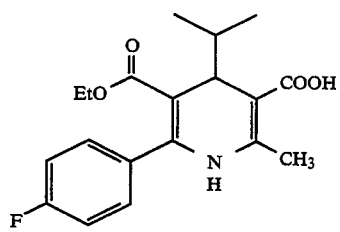

Analogously to Example 26, 7.17 g of crude product are obtained from 36 g (93.2 mmol) of the compound from Example 34.

Crude yield: 22.2% of theory $^1$H-NMR (DMSO): 67 =0.8 (m, 9H, CH$_3$); 1.6 (m, 1H, CHCH$_3$); 2.2, 2.25 (2s, 3H, CH$_3$); 3.8 (m, 3H, CH$_2$O, CH); 7.2–7.5 (m, 4H, aromatic-H) ppm.

EXAMPLE 36

Ethyl 1,4-dihydro-2-(4-fluorophenyl)-4-isopropyl-6-methyl-pyridine-3-carboxylate

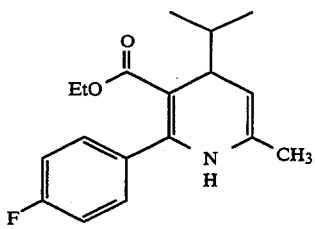

Analogously to Example 27, 7.15 g of crude product are obtained from 11.3 g (32.6 mmol) of Example 35.

Crude yield: 7.25% of theory $^1$H-NMR (CDCl$_3$): δ=0.8–1.3 (m, 9H, CH$_3$); 2.5, 2.6 (2s, 3H, CH$_3$); 3.1 (m, 1H, CHCH$_3$); 3.8–4.2 (m, 2H, CH$_2$O); 4.55, 5.2 (br, 1H, CH); 6.8 (s, 1H, CH); 6.9–8.0 (m, 4H, aromatic-H) ppm.

EXAMPLE 37

Ethyl 2-(4-fluorophenyl)-4-isopropyl-6-methyl-pyridine-3-carboxylate

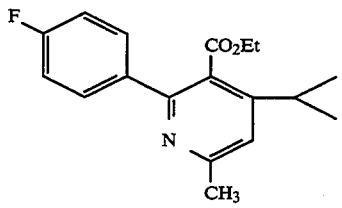

Analogously to Example 28, 2.82 g are obtained after chromatography (silica gel, toluene/ethanol 95:5) from 6.95 g (22.9 mmol) of the compound from Example 36.

Yield: 41% of theory $^1$H-NMR (CDCl$_3$): δ=1.0 (tr, 3H, CH$_3$); 1.3 (d, 6H, CH$_3$CH); 2.6 (S, 3H, CH$_3$); 3.1 (sept, 1H, CH); 4.1 (q, 2H, CH$_2$O); 7.0 (s, 1H, pyridine-H); 7.1–7.6 (m, 4H, aromatic-H) ppm.

EXAMPLE 38

2-(4-Fluorophenyl)-3-hydroxymethyl-4-isopropyl-6-methylpyridine

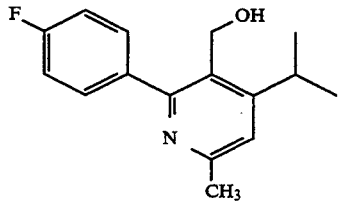

5.5 g (18.3 mmol) of the compound from Example 37 are reacted analogously to Example 29. After drying in a desiccator, 4.24 g of crude product are obtained.

Yield: 89% of theory $^1$H-NMR (CDCl$_3$): δ=1.3 (d, 6H); 2.55 (s, 3H); 3.36 (m, 1H); 4.49 (s, 2H); 7.09 (m, 3H); 7.53 (m, 2H) ppm.

EXAMPLE 39

2-(4-Fluorophenyl)-4-isopropyl-6-methyl-pyridine-3-carbaldehyde

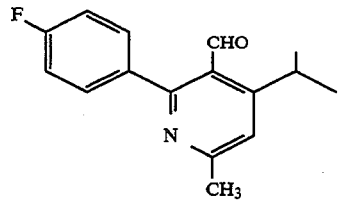

4.1 g (15.85 mmol) of the compound from Example 38 are reacted analogously to Example 30.

Yield: 2.23 g (54.7% of theory) $^1$H-NMR (CDCl$_3$): δ=1.3 (d, 6H); 2.65 (s, 3H); 3.91 (m, 1H); 7.10–7.28 (m, 3H); 7.5 (m, 2H); 9.91 (s, 1H) ppm.

EXAMPLE 40

(E)-3-[2-(4-Fluorophenyl),4-isopropyl-6-methyl-pyrid-3-yl]-prop-2-enal

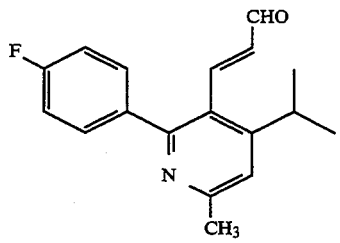

2.13 g (8.3 mmol) of the compound from Example 39 are reacted analogously to Example 8.

Yield: 1.34 g of crude product (57% of theory) $^1$H-NMR (CDCl$_3$): δ=12.8 (d, 6H); 2.6 (s, 3H); 3.27 (m, 1H); 6.11 (dd, 1H); 7.05–7.55 (m, 6H); 9.55 (d, 1H) ppm.

EXAMPLE 41

Methyl (E)-7-[2-(4-fluorophenyl)-4-isopropyl-6-methyl-pyrid-3-yl]-5-hydroxy-3-oxo-hept-6-enoate

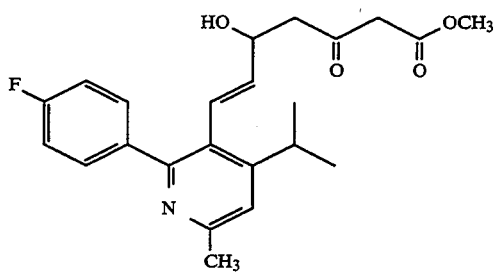

1.07 g (3.78 mmol) of the compound from Example 40 are reacted analogously to Example 32.

Yield: 0.34 g of crude product (22.5% of theory) $^1$H.NMR (CDCl$_3$): δ=1.25 (d, 6H); 2.5 (m, 2H); 2.57 (s, 3H); 3.2 (m, 1H) ; 3.42 (s, 2H); 3.75 (s, 3H); 4 .45 (m, 1H); 5.3 (dd, 1H); 6.6 (d, 1H); 7.05 (m, 3H); 7.43 (m, 2H) ppm.

EXAMPLE 42

Methyl erythro-(E)-7-[2-(4-fluorophenyl)-2-isopropyl-6-methyl-pyrid-3-yl]-3,5-dihydroxy-hept-6-enoate

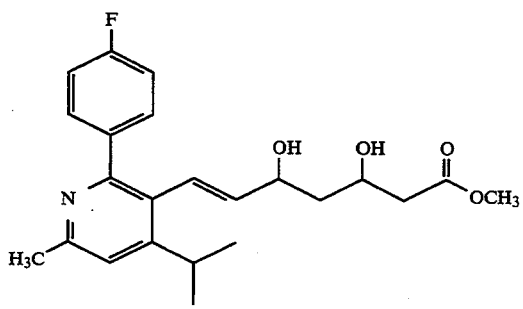

200 mg (0.5 mmol) of the compound from Example 41 are reacted analogously to Example 33.

Yield: 21.5 mg (10.7% of theory) $^1$H-NMR (CDCl$_3$): δ=1.23 (d, 6H); 1.5 (m, 2H); 2.45 (m, 2H); 2.58 (s, 3H); 3.21 (m, 1H); 3.72 (s, 3H); 4.11 (m, 1H); 4.38 (m, 1H); 5.31 (dd, 1H); 6.55 (d, 1H); 7.05 (m, 3H); 7.4 (m, 2H) ppm.

EXAMPLE 43

5-(2-Cyanoethyl)-3-ethyl-1,4-dihydro-4-(4-fluorophenyl)-2-isopropyl-6-methyl-pyrdine-3,5-dicarboxylate

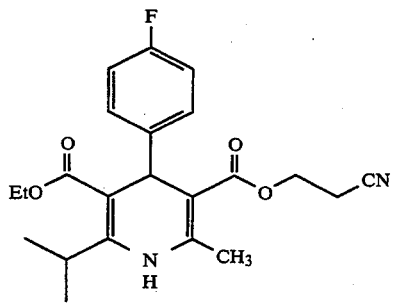

Analogously to Example 25, 44.6 g of crude product are obtained from 26.4 g (0.1 mol) of ethyl 4-fluorobenzylidene-2-butanoylacetate and 15.4 g (0.1 mol) of 2-cyanoethyl 3-aminocrotonate.

Crude yield: 100% of theory $^1$H-NMR (DMSO): δ=1.15 (m, 9H, CH$_3$—CH$_2$, CH$_3$—CH—CH$_3$); 2.3 (s, 3H , CH$_3$); 2.45 (m, 2H, CH$_2$-CN); 4.0 (q, 2H, CH$_2$O); 4.1 (m, 1H, CHCH$_3$) ; 4.15 (m, 2H, CH$_2$O); 4.4 (s, 1H, p-FC$_6$H$_4$CH); 6.9–7.3 (m, 4H, aromatic-H); 8.3 (s, 1H, NH) ppm.

EXAMPLE 44

3-Ethyl-1,4-dihydro-4-(4-fluorophenyl)-2-isopropyl-6-methyl-pyridine-3,5-dicarboxylate

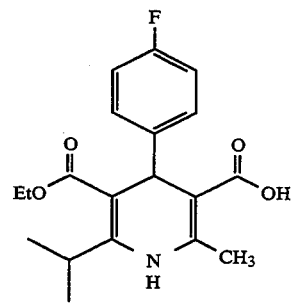

Analogously to Example 26, 8.5 g of crude product are obtained from 10.2 g (25.6 mmol) of the compound from Example 43.

Crude yield: 95% of theory $^1$H-NMR (DMSO): δ=1.15 (m, 9H, CH$_3$CH$_2$, CH$_3$CHCH$_3$); 2.25, 2.3 (2s, 3H, CH$_3$); 4.0 (m, 3H, CH$_2$O, CH$_3$CH); 4.85, 6.3 (2s, 1H, FC$_6$H$_4$-CH); 6.9–7.3 (m, 4H, aromatic-H); 8.1 (s, 1H, NH); 10.9 (s, 1H, COOH) ppm.

EXAMPLE 45

Ethyl 1,4-dihydro-4-(4-fluorophenyl)-2-isopropyl-6-methyl-pyridine-3-carboxylate

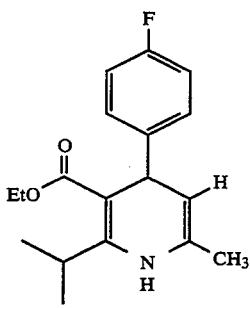

Analogously to Example 27, 5.6 g of crude product are obtained from 8.35 g (24 mmol) of the compound from Example 44.

Crude yield: 77.5% of theory $^1$H-NMR (CDCl$_3$): δ=1.2 (m, 9H, CH$_3$CH$_2$, CH$_3$CHCH$_3$); 2.6 (s, 3H, CH$_3$); 4.1 (m, CHCH$_3$, CH$_2$O); 4.5, 4.6 (2d, 1H, FC$_6$H$_4$CH); 5.3 (s, 1H, NH); 6.9–7.4 (m, >5H, aromatic-H) ppm.

EXAMPLE 46

Ethyl 4-(4-fluorophenyl)-2-isopropyl-6-methyl-pyridine-3-carboxylate

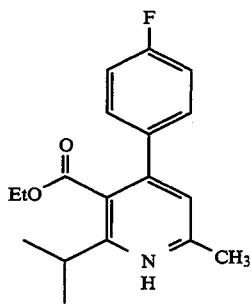

Analogously to Example 37, 2.9 g of red oil are obtained after chromatography over silica gel (dichloromethane) from 5.5 g (18.Z mmol) of the compound from Example 45.

Yield: 53% of theory $^1$H-NMR (CDCl$_3$); $\delta$=1.05 (tr, 3H, CH$_3$CH$_2$); 1.35 (d, 6H, CH$_3$CH); 2.6 (s, 3H, CH$_3$); 3.15 (sept., 1H, CH); 4.1 (q, 2H, CH$_2$); 6.95 (s, 1H, pyridine-H); 7.1–7.4 (m, 4H, aromatic-H) ppm.

EXAMPLE 47

4-(4-Fluorophenyl)-3-hydroxymethyl-2-isopropyl-6-methylpyridine

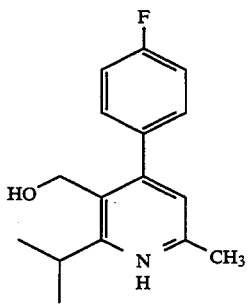

Analgously to Example 29, 2.19 g of product are obtained from 2.8 g (9.3 mmol) of the compound from Example 46.

Yield: 91% of theory $^1$H-NMR (CDCl$_3$): $\delta$=1.3 (d, 6H, CH$_3$CH); 1.5 (br, 1H, OH); 2.5 (s, 3H, CH$_3$); 3.5 (sept., 1H, CH); 4.6 (s, 2H, CH$_2$); 6.9 (s, 1H, pyridine-H); 7.1–7.5 (m, 4H, aromatic-H) ppm.

EXAMPLE 48

4-(4-Fluorophenyl)-2-isopropyl-6-methyl-pyridine-3-carbaldehyde

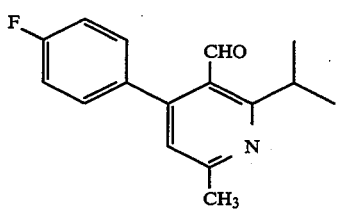

Analogously to Example 30, 0.56 g of product is obtained from 2.0 g (7.7 mmol) of the compound from Example 47.

Yield: 28.3% of theory $^1$H-NMR (CDCl$_3$): $\delta$=1.3 (d, 6H, CH$_3$CH); 2.6 (s, 3H, CH$_3$); 3.6 (sept, 1H, CH); /, 0 (s, 1H, pyridine-H); 7.1–7.4 (m, 4H, aromatic-H); 10.0 (s, 1H, CHO) ppm.

EXAMPLE 49

(E)-3-[4-(4-Fluorophenyl)-2-isopropyl-6-methyl-pyrid-3yl]-prop-2-enal

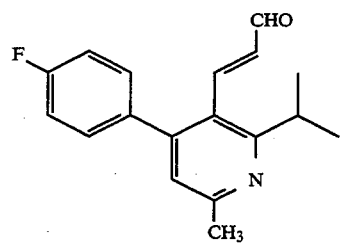

Analogously to Example 31, 0.48 g is obtained from 0.51 g (1.99 mmol) of the compound from Example 48.

Yield: 85.5% of theory $^1$H-NMR (CDCl$_3$): $\delta$=1.2 (d, 6H, CH$_3$CH); 2.5 (s, 3H, CH$_3$); 3.3 (sept, 1H, CH); 6.0 (dd, 1H, CHCHO); 6.9 (s, 1H, pyridine-H); 7.0–7.3 (m, 4H, aromatic-H); 7.5 (d, 1H,CH); 9.5 (d, 1H, CHO) ppm.

EXAMPLE 50

Methyl (E)-7-[4-(4-fluorophenyl)-2-isopropyl-6-methyl-pyrid-3-yl]-5-hydroxy-3-oxo-hept-6-enoate

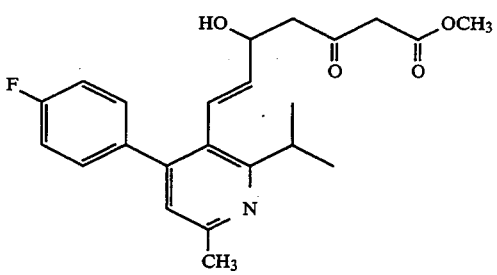

Analogously to Example 32, 0.22 g is obtained from 0.41 g (1.44 mmol) of the compound from Example 49.

Yield: 38.2% of theory $^1$H-NMR (CDCl$_3$): $\delta$=1.3 (d, 6H, CH$_3$CH); 2.5 (s, 3H, CH$_3$); 3.3 (sept, 1H, CH); 3.5 (s, 2H, CH$_2$); 3.25 (s, 3H, OCH$_3$); 4.6 (m, 1H; CHOH); 5.3 (dd, 1H, CH); 6.6 (d, 1H, CH); 6.9 (s, 1H, pyridine-H); 7.0–7.3 (m, 4H, aromatic-H) ppm.

EXAMPLE 51

Methyl erythro-(E)-7-[4-(4-fluorophenyl)-2-isopropyl-6-methyl-pyrid-3-yl]-3,5-dihydroxy-hept-6-enoate

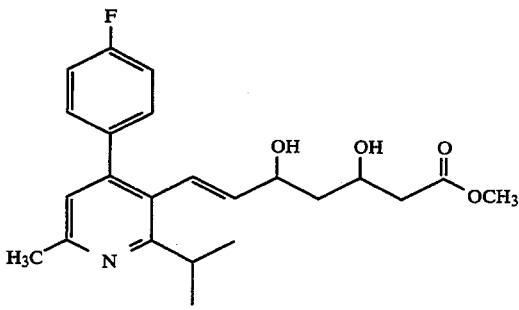

1.2 g (3.01.mmol) of the compound from Example 50 are reacted analogously to Example 33.

Yield: 320 mg (26.6% of theory) $^1$H-NMR (CDCl$_3$): $\delta = 1.28$ (d, 6H); 1.40 (m, 2H); 2.45 3(m, 2H); 2.55 (s, 3H); 3.35 (m, 1H); 3.72 (s, 3H); 4.15 (m, 1H); 4.39 (m, 1H); 5.30 (dd, 1H); 6.55 (d, 1H); 6.88 (s, 1H); 7.0-7.30 (m, 4H) ppm.

EXAMPLE 52

Methyl 1,4-dihydro-2,6-dimethyl-4-(4-fluorophenyl)-5-phenyl-pyridine-3-carboxylate

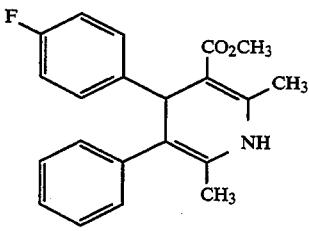

24.0 g (0.1 mol) of 1-(4-fluorophenyl)-2-phenylbuten-3-one, 23 g (0.2 mol) of methyl 3-amino-crotonate and 6 ml (0.1 mol) of glacial acetic acid are heated under reflux overnight in 1 50 m of ethanol, heated under reflux for 18 h after addition of 11.5 g (0.1 mol) of methyl 3-aminocrotonate and 3ml of glacial acetic acid and heated under reflux for 18 h once more after repeated addition of 11.5 g (0.1 mol) of methyl 3-aminocrotonate and 3 ml of glacial acetic acid. The solvent is removed in vacuo, 80 ml of methanol are added to the residue, undissolved material is filtered off with suction, the methanolic solution is concentrated in vacuo and excess aminocrotonate is distilled off from the residue at 73° C.-90° C./18 mbar and subsequently at 60° C.-70° C. 0.2 mbar. 37.5 g of crude product are obtained as a brittle fused mass.

Crude yield: >100% of theory $^1$H-NMR (CDCl$_3$): $\delta = 1.85$ (s, 3H, CH$_3$); 2.85 (s, 3H, CH$_3$); 3.6 (s, 3H, CH$_3$); 4.65, 5.4 (2br, s, 1H, CH); 6.7-7.4 (m, 9H, aromatic-H) ppm.

EXAMPLE 53

Methyl 2,6-dimethyl-4-(4-fluorophenyl)-5-phenyl-pyridine-3carboxylate

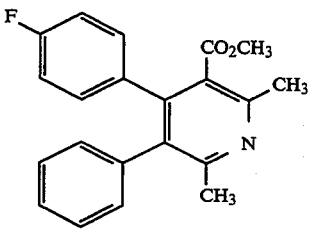

Analogously to Example 37, 20.4 g of solid are obtained from 37.3 g (0.1 mol, crude) of the compound from Example 52.

Yield: 49.4% of theory $^1$H-NMR (CDCl$_3$): $\delta = 2.45$ (s, 3H, CH$_3$); 2.6 (s, 3H, CH$_3$); 3.5 (s, 3H, CH$_3$); 6.7-7.4 (m, 9H, aromatic-H) ppm.

EXAMPLE 54

2,6-Dimethyl-4-(4-fluorophenyl)-3-hydroxymethyl-5-phenylpyridine

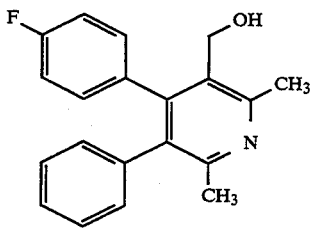

Analogously to Example 29, 12.4 g of crude product are obtained from 20.2 g (60 mmol) of the compound from Example 53.

Yield: 67% of theory $^1$H-NMR (CDCl$_3$): $\delta = 2.0$ (br, s, 1H, OH); 2.3 (s, 3H, CH$_3$); 2.75 (s, 3H, CH$_3$); 4.45 (s, 2H, CH$_2$); 6.8-7.3 (m, 9H, aromatic-H) ppm.

EXAMPLE 55

2,6-Dimethyl-4-(4-fluorophenyl)-5-phenyl-pyridine-3-carbaldehyde

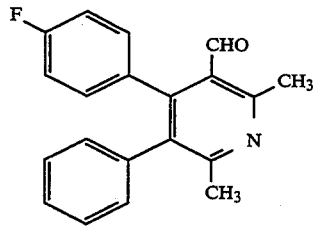

Analogously to Example 30, 3.8 g of solid are obtained after chromatography over silica gel (dichloromethane) from 6.0 g (19.5 mmol) of the compound from Example 54.

Yield: 64% of theory $^1$H-NMR (CDCl$_3$): $\delta = 2.4$ (s, 3H,CH$_3$); 2.9 (s, 3H, CH$_3$); 6.8-7.3 (m, 9H, aromatic-H) 9.8 (s, 1H, CHO) ppm.

EXAMPLE 56

(E)-3-[2,6-Dimethyl-4-(4-fluorophenyl)-5-phenyl-pyrid-3-yl]-prop-2-enal

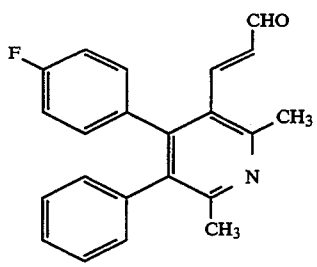

Analogously to Example 31, 2.0 g of crude product are obtained from 3.1 g (10 mmol) of the compound from Example 55.

Yield: 60% of theory $^1$H-NMR (CDCl$_3$): δ=2.4 (s, 3H, CH$_3$); 2.75 (s, 3H, CH$_3$); 6.15 (dd, 1H, CHCHO); 6.85 (d, 1H, CH); 6.9-7.3. (m, 9H, aromatic-H); 9.4 (d, 1H, CHO) ppm.

EXAMPLE 57

Methyl (E)-7-[2,6-dimethyl-4-(4-fluorophenyl)-5-phenyl-pyrid-3-yl ]-5-hydroxy-3-oxo-hept-6-enoate

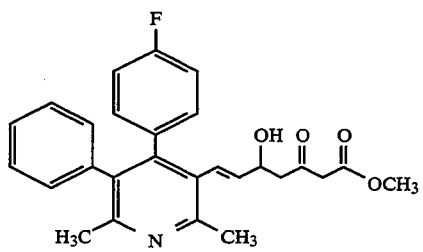

Analogously to Example 32, 2.4 g of crude product are obtained from 2.0 g (6 mmol) of the compound from Example 56.

Crude yield: 89% of theory $^1$H-NMR (CDCl$_3$): δ=2.3 (s, 3H, CH$_3$); 2.6. (s, 3H, CH$_3$); 2.7 (m, 2H, CH$_2$); 3.45 (d, 2H, CH$_2$); 3.75 (2s, 3H, OCH$_3$); 4.5 (m, 1H, CH); 5.4 (dd, 1H, CHCHO); 6.3 (2d, 1H, CH); 6.7-7.3 (m, 9H, aromatic-H) ppm.

EXAMPLE 58

Methyl erythro-(E)-7-[2,6-dimethyl-4-(4-fluorophenyl)-5-phenyl-pyrid-3-yl]-3,5-dihydroxy-hept-6-enoate

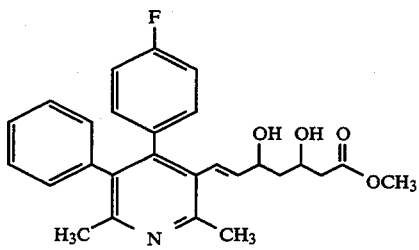

Analogously to Example 33, 550 mg of product are obtained after chromatography over silica gel (ethyl acetate) from 2.4 g (5.3 mmol) of the compound from Example 57.

Yield: 23.1% of theory $^1$H-NMR (CDCl$_3$): δ=1.7 (br, s, 2H, OH); 2.3 (s, 3H, CH$_3$); 2.4–2.6 (m, 2H, CH$_2$); 2.65 (s, 3H, CH$_3$); 3.7 (s, 3H, OCH$_3$); 4.1 (m, 1H, CHOH); 4.45 (m, 1H, CHOH); 5.4 (dd, 1H, CHCHOH); 6.3 (d, 1H, CH); 6.7-7.3 (m 9H, aromatic-H) ppm.

EXAMPLE 59

Ethyl 2,6-diisopropyl-4-(4-fluorophenyl)-5-methoxymethyl-pyridine-3-carboxylate

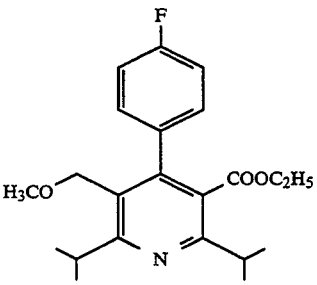

0.57 ml (9.2 mmol)of methyl iodide and, at −50° C., 327 mg (10.9 mmol) of 80% strength sodium hydride are added under a nitrogen atmosphere to 3 g (8.4 mmol) of the compound from Example 4 in 100 ml of dry tetrahydrofuran. The mixture is stirred for 2 hours and the temperature is allowed to rise to 25° C. in the course of this. Water is cautiously added to the mixture and it is extracted several times using ether, and the organic phase is dried over sodium sulphate and concentrated in vacuo.

Yield: 2.9 g (92.7% of theory) $^1$H-NHR (CDCl$_3$): δ=0.97 (t, 3H); 1.3 (m, 12H); 3.05 (m, 1H); 3.21 (s, 3H); 3.38 (m, 1H); 3.96 (q, 2H); 4.1 (s, 2H); 7.08 (m, 2H); 7.25 (m, 2H) ppm.

EXAMPLE 60

2,6-Diisopropyl-4-(4-fluorophenyl)-3-hydroxymethyl-5-methoxymethyl-pyridine

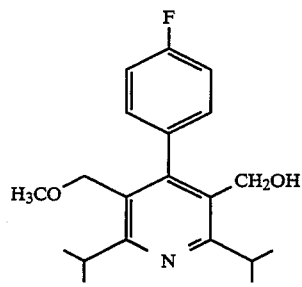

2.85 g (7.6 mmol) of the compound from Example 59 dissolved in 30 ml of absolute tetrahydrofuran are added dropwise under a nitrogen atmosphere to 0.5 g (13.2 mmol) of lithium aluminum hydride in 20 ml of absolute tetrahydrofuran at 60° C. The mixture is heated to reflux for 1 hour, subsequently cooled to 0° C. and 1.5 ml of water and 0.3 ml of 15% strength potassium hydroxide solution are cautiously added dropwise. The solution is filtered from the deposited precipitate with suction and the latter is boiled several times with ether. The combined phases are dried over magnesium sulphate and concentrated in vacuo. The residue is chromatographed on a column (silica gel 70–230 mesh, using ethyl acetate/petroleum ether 1:9).

Yield: 1.9 g (74.8% of theory) $^1$H-NMR (CDCl$_3$): δ=1.3 (m, 12H); 3.17 (s, 3H); 3.35 (m, 1H); 3.43 (m, 1H); 4.02 (s, 2H); 4.35 (d, 2H); 7.12 (m, 2H); 7.25 (m, 2H) ppm.

EXAMPLE 61

Methyl erythro-(E)-7-[2,6-diisopropyl-4-(4-fluorophenyl)-5-methoxymethyl-pyrid-3-yl]-3,5-dihydroxy-hept-6-enoate

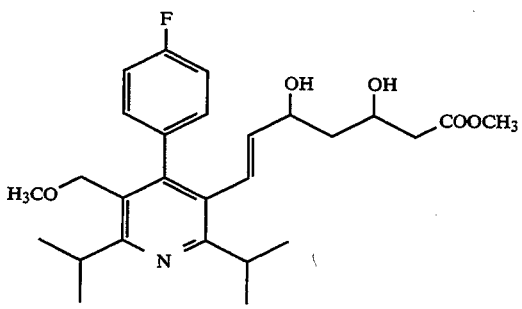

Example 61 was prepared from the compound from Example 60, in analogy to the reactions of Examples 7, 8, 9 and 10.

$^1$H-NMR (CDCl$_3$): δ=1.23 (m, 6H); 1.32 (d, 6H); 1.40 (m, 2H); 2.43 (m, 2H); 3.18 (s, 3H); 3.32 (m, 2H); 3.73 (s, 3H); 4.05 (s, 2H); 4.08 (m, 1H); 4.29 (m, 1H); 5.23 (dd, 1H); 6.31 (d, 1H); 7.0–7.20 (m, 4H) ppm.

EXAMPLE 62

Methyl erythro-(E)-7-[5-tert.butyldimethylsilyloxymethyl-4-fluorophenyl)-2-isopropyl-6-methyl-pyrid-3-yl]-3,5-dihydroxy-hept-6-enoate

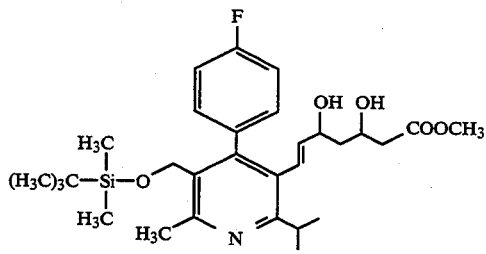

The following compound was synthesized from the compound from Example 20 in analogy to the reactions of Examples 5, 6, 7, 8, 9, 10, 11 and 12.

$^1$H-NMR (CDCl$_3$): δ=0.0 (s, 6H); 0.82 (s, 9H); 1.22 (d, 6H); 1.40 (m, 2H); 2.42 (m, 2H); 2.65 (s, 3H); 3.28 (m, 1H); 3.70 (s, 3H); 4.08 (m, 1H); 4.26 (m, 1H); 4.29 (s, 2H); 5.22 (dd, 1H); 6.30 (d, 1H); 7.0–7.20 (m, 4H) ppm.

EXAMPLE 63

Methyl erythro-(E)-7-[4-(4-fluorophenyl)-5-hydroxymethyl-2-isopropyl-6-methyl-pyrid-3-yl]-3,5-dihydroxy-hept-6-enoate

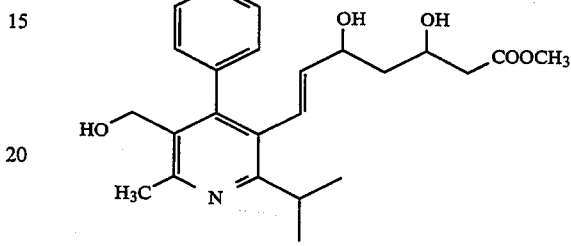

The following compound was synthesized from the compound from Example 20 in analogy to the reactions from Examples 5, 6, 7, 8, 9, 10, 11 and 12.

$^1$H-NMR (CDCl$_3$): δ=1.22 (d, 6H); 1.30–1.60 (m, 2H); 2.43 (m, 2H); 2.69 (s, 3H); 3.32 (m, 1H); 3.72 (s, 3H); 4.07 (m, 1H); 4.30 (m, 1H); 4.41 (s, 2H); 5.25 (dd, 1H); 6.31 (d, 1H); 7.11 (m, 4H) ppm.

EXAMPLE 64

Methyl erythro-(E)-7-[3-benzyloxymethyl-4-(4-fluorophenyl)-6-isopropyl-2-methyl-pyrid-5-yl]-3,5-dihydroxy-hept-6-enoate

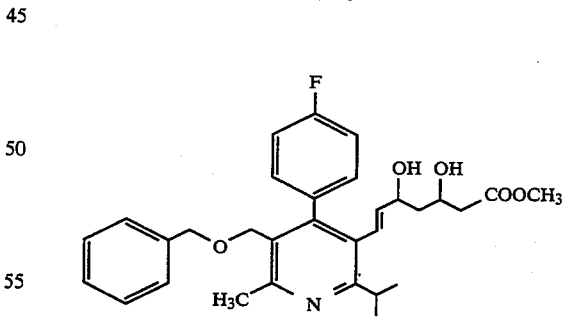

The following compound was synthesized from the compound from Example 20 in analogy to the reactions from Examples 5, 6, 7, 8, 9, 10, 11 and 12.

$^1$H-NMR (CDCl$_3$): δ=1.23 (d, 6H); 1.40 (m, 2H); 2.42 (m, 2H); 2.63 (s, 3H); 3.30 (m, 1H); 3.72 (s, 3H); 4.10 (m, 1H); 4.15 (s, 2H); 4.32 (m, 1H); 4.38 (S, 2H); 5.20 (dd, 1H); 6.31 (d, 1H); 7.0–7.40 (m, 9H) ppm.

EXAMPLE 65

3-(tert.Butyldimethylsilyloxymethyl)-2,6-diisopropyl-5-(2,2-dimethyl-butyryloxymethyl)-4-(4-fluorophenyl)-pyridine

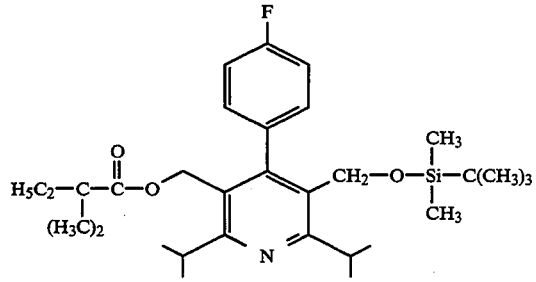

865 mg (3.3 mmol) of triphenylphosphine, 0.41 ml (3.3 mmol) of 2,2-dimethylbutyric acid and 0.52 ml (3.3 mmol) of diethyl azodicarboxylate are added successively at 0° C. to 1.29 g of the compound from Example 6 in 50 ml of absolute tetrahydrofuran and the mixture is stirred overnight at room temperature. The mixture is concentrated in vacuo and t he residue is chromatographed on a column (silica gel 70–230 mesh, using ethyl acetate/petroleum ether 1:9).

Yield; 1.32 g (87.4% of theory) $^1$H-NMR (CDCl$_3$): δ=0.01 (s, 6H); 0.86 (t, 3H); 0.91 (s, 9H); 1.2 (s, 6H); 1.39 (m, 12H); 1.6 (q, 2H); 3.24 (m, 1H); 3.48 (m, 1H); 4.38 (s, 2H); 4.79 (s, 2H); 7.05–7.35 (m, 4H) ppm.

EXAMPLE 66

2,6-Diisopropyl-3-(2,2-dimethyl-butyryloxymethyl)-4-(4-fluorophenyl)-5-hydroxymethyl-pyridine

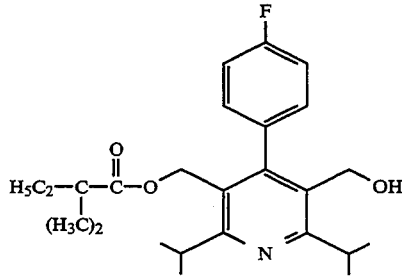

2.6 ml (2.6 mmol) of a 1 molar tetrabutylammonium fluoride solution in tetrahydrofuran are added to 1.3 g (2.6 mmol) of the compound from Example 65 dissolved in 20 ml of absolute tetrahydrofuran and the mixture is stirred for 1 hour at room temperature. Saturated sodium hydrogen carbonate solution is added to the mixture and it is extracted several times using dichloromethane. The organic phase is dried over magnesium sulphate and concentrated in vacuo, and the residue is chromatographed on a column (silica gel 70–230 mesh, using ethyl acetate/petroleum ether 1:9 as eluent).

Yield: 1 g (95.2% of theory) $^1$H-NMR (CDCl$_3$): δ=0.71 (t, 3H); 1.02 (s, 6H); 1.21 (d, 6H); 1.25 (d, 6H); 1.43 (q, 2H); 3.09 (m, 1H); 3.38 (m, 1H); 4.3 (d, 2H); 4.61 (s, 2H); 6.95–7.18 (m, 4H) ppm.

EXAMPLE 67

2,6-Diisopropyl-5-(2,2-dimethyl-butyryloxymethyl)-4-(4-fluorophenyl)-pyridine-3-carbaldehyde

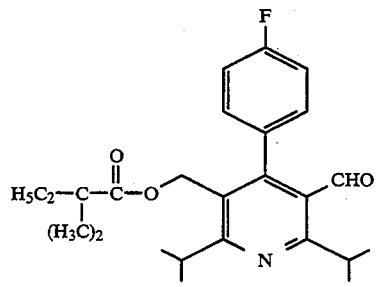

1 g (2.5 mmol) of the compound from Example 66 are reacted analogously to Example 7.

Yield: 890 mg (86.4% of theory) $^1$H-NMR (CDCl$_3$): δ=0.82 (t, 3H); 1.25 (s, 6H); 1.32. (m, 12H); 1.55 (q, 2H); 3.26 (m, 1H) 3.88 (m, 1H); 4.77 (s, 2H); 7.09–7.27 (m, 4H); 9.77 (s, 1H) ppm.

EXAMPLE 68

(E)-3-[2,6-Diisopropyl-5-(2,2-dimethyl-butyryloxymethyl)-4-(4-fluorophenyl)-pyrid-3-3-yl]-prop-2-enal

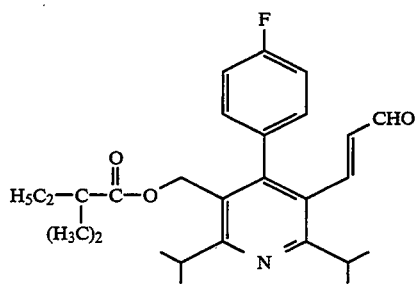

860 mg (2.1 mol) of the compound from Example 67 are reacted analogously to Example 8.

Yield: 420 mg (45.6% of theory) $^1$H-NMR (CDCl$_3$): δ=0.82 (t, 3H); 1.14 (s, 6H); 1.31 (m, 12H); 1.53 (q, 2H); 3.22(m, 1H); 3.33 (m, 1H); 4.75 (s, 2H); 5.99 (dd, 1H); 7.05–7.29 (m, 5H); 9.4 (d, 1H) ppm.

EXAMPLE 69

Methyl (E)-7-[2,6-diisopropyl-5-(2,2-dimethyl-butyryloxymethyl)-4-(4-fluorophenyl)pyrid-3-yl]-5-hydroxy-3-oxo-hept-6-enoate

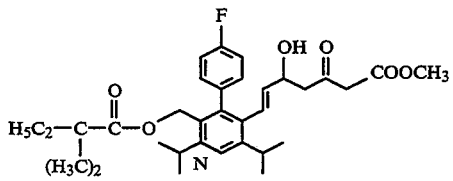

0.15 ml (1.4 mmol) of methyl acetoacetate in 2 ml of absolute tetrahydrofuran is added dropwise under nitrogen to a suspension of 54.6 mg (1.82 mmol) of 80% strength sodium hydride in 5 ml of absolute tetrahydrofuran at −5° C. After 15 minutes, 0.89 ml (1.4 mmol) of 15% strength butyllithium in n-hexane is added dropwise at the same temperature and after a further 15 minutes 408 mg (1.8 mmol) of dry zinc bromide in 5 ml of absolute tetrahydrofuran are added. The mixture is allowed to stir for a further 15 minutes at −5° C., 400 mg (0.91 mmol) of the compound from Example 68 dissolved in 10 ml of dry tetrahydrofuran are added and the mixture is stirred overnight. Saturated ammonium chloride solution is added to the mixture and it is extracted several times using ether. The organic phase is dried over magnesium sulphate and concentrated in vacuo, and the residue is chromatographed on a column (silica gel 70–230 mesh, using ethyl acetate/petroleum ether 3:7).

Yield: 200 mg (38.5% of theory) $^1$H-NMR (CDCl$_3$): δ=0.8 (t, 3H); 1.12 (s, 6H); 1.27 (d, 6H); 1.32 (d, 6H); 1.53 (q, 2H); 2.45 (m, 2H); 3.18 (m, 1H); 3.27 (m, 1H); 3.43 (s, 2H); 3.74 (s, 3H), 4.50 (m, 1H); 4.73 (s, 2H); 5.28 (dd, 1H); 6.38 (d, 1H); 7.0–7.10 (m, 4H) ppm.

EXAMPLE 70

Methyl erythro-(E)-7-[2,6-diisopropyl-5-(2,2-dimethyl-butyryloxymethyl)-4-(4-fluorophenyl)-pyrid-3-yl]-3,5-dihydroxy-hept-6-enoate

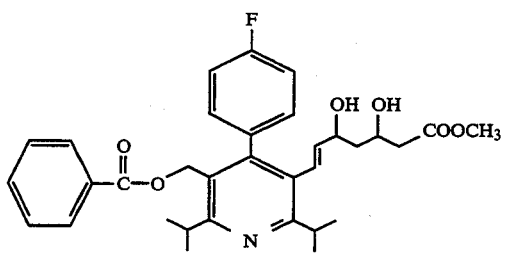

180 mg (0.32 mmol) of the compound from Example are reacted analogously to Example 10.

Yield: 138 mg (77.5% of theory) $^1$H-NMR (CDCl$_3$): δ=0.81 (t, 3H); 1.12 (s, 6H); 1.28 (m, 6H); 1.40 (m, 2H); 1.53 (q, 2H); 2.43 (m, 2H); 3.17 (m, 1H); 3.32 (m, 1H); 3.73 (s, 3H); 4.08 (m, 1H); 4.31 (m, 1H); 4.75 (s, 2.H); 5.28 (dd, 1H); 6.32 (d, 1H); 7.0–7.1 (m, 4H) ppm.

EXAMPLE 71

Methyl erythro(E)-7-[5-benzoloxymethyl-2,6-diisopropyl-4-(4-fluorophenyl)-pyrid-3-yl]-3,5-dihydroxy-hept-6-enoate

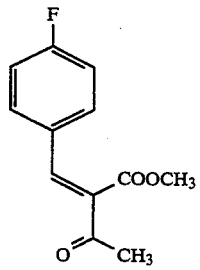

The following compound was synthesized from the compound from Example 6 in analogy to the reactions of Examples 65, 66, 67, 68, 69 and 70.

$^1$H-NMR (CDCl$_3$): δ=1.31 (m, 6H); 1.40 (m, 2H); 2.43 (m, 2H); 3.32 (m, 2H); 3.73 (s, 3H); 4.07 (m, 1H); 4.32 (m, 1H); 5.07 (s, 2H); 5.30 (dd, 1H); 6.32 (d, 1H); 6.90–7.20 (m, 4H); 7.42 (m, 2H); 7.55 (m, 1H); 8.02 (m, 2H) ppm.

EXAMPLE 72

Methyl erythro-(E)-7-[3-acetoxymethyl-2,6-diisopropyl-4-(4-fluorophenyl)-pyrid-5-yl]-3,5-dihydroxy-hept-6-enoate

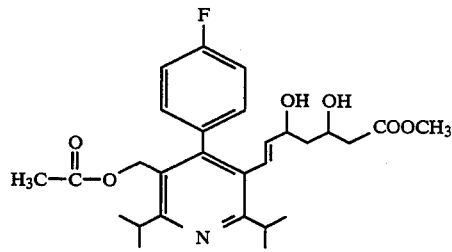

The following compound was synthesized from the compound from Example 6 in analogy to the reactions from Examples 65, 66, 67, 68, 69 and 70.

$^1$H-NMR (CDCl$_3$): δ=1.25 (m, 12H); 1.40 (m, 2H); 2.02 (s, 3H); 2.43 (m, 3H); 3.20 (m, 1H); 3.32 (m, 1H); 3.72 (s, 3H); 4.07 (m, 1H); 4.29 (m, 1H); 4.81 (S, 2H); 5.28 (dd, 1H); 6.30 (d, 1H); 7.0–7.1 (m, 4H) ppm.

EXAMPLE 73

(E/Z)-3-Carboxymethyl-4-(4-fluorophenyl)but-3-en-2-one 62 g (0.5 mol) of 4-fluorobenzaldehyde and 53.9 ml (0.5 mol) of methyl acetoacetate are initially introduced in 300 ml of isopropanol, a mixture of 2.81 ml (28 mmol) of piperidine and 1.66 ml (29 mmol) of acetic acid in 40 ml of isopropanol is added and the mixture is stirred for 48 h at room temperature. The mixture is concentrated in vacuo and the residue is distilled in a high vacuum.

B.p. 0.5 mm: 138° C. Yield: 50.5 g (45.5% of theory)

EXAMPLE 74

Dimethyl 1,4-dihydro-2,6-dimethyl-4-(4-fluorophenyl)-pyridine-3,5-dicarboxylate

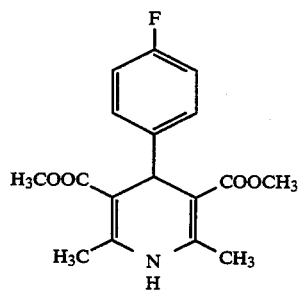

33.3 g (0.15 mol) of the compound from Example 73 are heated under reflux for 4 h with 17.3 g (0.15 mol) of methyl 3-aminocrotonate in 150 ml of ethanol. The mixture is cooled to 0° C. and the deposited precipitate is filtered off with suction, washed with a little petroleum ether and dried in a desiccator.

Yield: 32 g (66.8% of theory) $^1$H-NMR (CDCl$_3$): δ=2.33 (s, 6H); 3.65 (s, 6H); 4.99 (s, 1H); 5.77 (s, 1H); 6.89 (m, 2H); 7.22 (m, 2H) ppm.

EXAMPLE 75

Dimethyl 2,6-dimethyl-4-(4-fluorophenyl)-pyridine-3,5-dicarboxylate

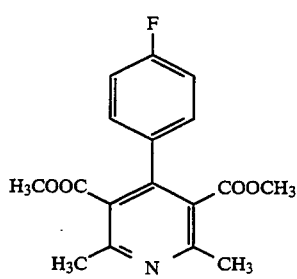

32 g (0.1 mol) of the compound from Example 74 are reacted analogously to Example 3.

Yield: 27.2 g (87% of theory) $^1$H-NMR (CDCl$_3$): δ=2.59 (s, 6H); 3.56 (s, 6H); 7.08 (m, 2H); 7.25 (m, 2H) ppm.

EXAMPLE 76

Methyl 2,6-dimethyl-4-(4-fluorophenyl)-5-hydroxy-methylpyridine-3-carboxylate

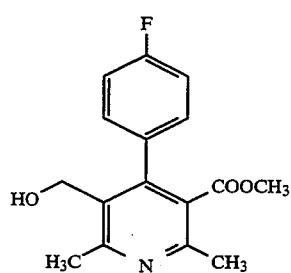

40.3 ml (141 mmol) of a 3.5 molar solution of sodium bis-(2-methoxyethoxy)-dihydroaluminate in toluene are added under nitrogen to a solution of 14.9 g (47 mmol) of the compound from Example 75 in 300 ml of dry tetrahydrofuran at −10° C. to −5° C. and the mixture is stirred for 30 minutes at room temperature. After cooling to 0° C., 150 ml of water are cautiously added dropwise and the mixture is extracted several times using ethyl acetate. The combined organic phases are washed with saturated sodium chloride solution, dried over magnesium sulphate and concentrated in vacuo. The residue crystallizes using ether/petroleum ether. After drying in a desiccator, 7.5 g of substance (55.2% of theory) are obtained $^1$H-NMR (CDCl$_3$): δ=2.52 (s., 3H); 2.7 (s, 3H); 3.52 (s, 3H); 4.45 (s, 2H); 7.05–7.3 (m, 4H) ppm.

EXAMPLE 77

Methyl erythro-(E)-7-[5-tert-butyldimethylsilyloxymethyl-2,6-dimethyl-4-(4-fluorophenyl)pyrid-3-yl]-3,5-dihydroxy-hept-6-enoate

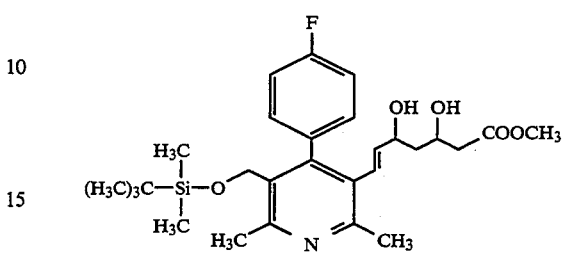

Example 77 was prepared from the compound of Example 76 in analogy to the reactions of Examples 5, 6, 7, 8, 9 and 10.

$^1$H-NMR (CDCl$_3$): δ=0.01 (s, 6H); 0.92 (s, 9H); 1.40 (m, 2H); 2.49 (m, 2H); 2.62 (s, 3H); 2.71 (s, 3H); 3.80 (s, 3H); 4.17 (m, 1H); 4.36 (s, 2H); 4.38 (m, 1H); 5.42 (dd, 1H); 6.31 (d, 1H); 7.10–7.20 (m, 4H) ppm.

EXAMPLE 78

Methyl erythro-(E)-7-[2,6-dimethyl-4-(4-fluorophenyl)-5-hydroxymethyl-pyrid-3-yl]-3,5-dihydroxy-hept-6-enoate

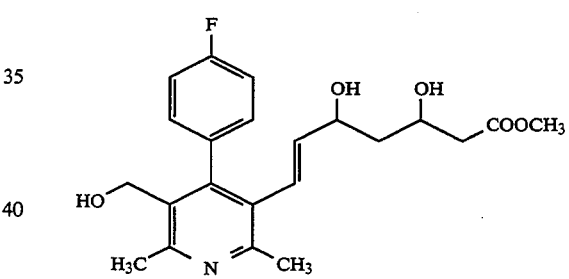

Example 78 was prepared analogously to Example 11 from the compound from Example 77.

EXAMPLE 79

(E/Z)-2-Carboxyethyl-1-cyclopropyl-3-(4-fluorophenyl)-2-prop-2-en1-one

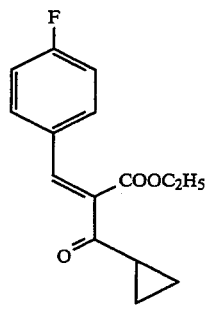

39 g.(0.25 mol) of ethyl cyclopropylcarbonylacetate and 31 g (0.25 mol) of 4-fluorobenzaldehyde are initially introduced in 150 ml of dry isopropanol and a mixture of 1.4 ml (14 mmol) of piperidine an 0.83 ml (14.5 mmol) of acetic acid in 20 ml of isopropanol is added. The mixture is stirred for 48 hours at room temperature and concentrated in and the residue is distilled in a high vacuum.

B.p. 0.5 mm: 140° C. Yield: 52.3 g (79.8% of theory)

EXAMPLE 80

Diethyl 1,4-dihydro-2-cyclopropyl-4-(4-fluorophenyl)-6-isopropyl-pyridine-3,5-dicarboxylate

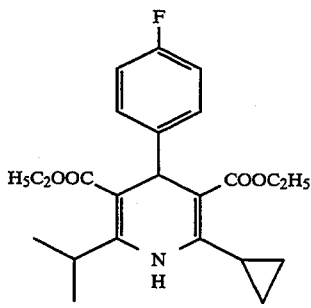

39.3 g (0.15 mol) of the compound from Example 79 and 23.6 g (0.15 mol) of ethyl 3-amino-4-methyl-pent-2-enoate are heated under reflux overnight in 150 ml of ethylene glycol. After cooling to room temperature, the mixture is extracted several times using ether and the combined ether phases are washed three times with 10% strength hydrochloric acid, once each with water and saturated sodium hydrogen carbonate solution, dried over magnesium sulphate and concentrated in vacuo. The residue is stirred with petroleum ether/ether, filtered off with suction and dried in a desiccator.

Yield: 22.8 g (37.8% of theory) $^1$H-NMR (CDCl$_3$): $\delta$=0.65 (m, 2H); 1.03 (m, 2H); 1.15 (m, 13H); 2.78 (m, 1H); 4.15 (m, 4H); 5.03 (s, 1H); 5.72 (s, 1H); 6.90 (m, 2H); 7.22 (m, 2H) ppm.

EXAMPLE 81

Diethyl 2-cyclopropyl-4-(4-fluorophenyl)-6-isopropylpyridine-3,5-dicarboxylate

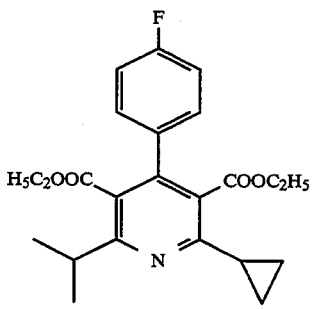

19.1 g (47 mmol) of the compound from Example 80 are reacted analogously to Example 3.

Yield: 9.8 g (52.5% of theory) $^1$H-NMR (CDCl$_3$): $\delta$=0.97 (m, 8H); 1.25 (m, 8H); 2.09 (m, 1H); 3.06 (m, 1h); 4.02 (m, 4H); 7.06 (m, 2H); 7.26 (m, 2H) ppm.

EXAMPLE 82

Ethyl 6-cyclopropyl-4-(4-fluorophenyl)-5-hydroxymethyl-2-isopropyl-pyridine-3-carboxylate

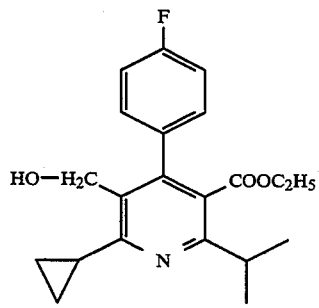

6 g (15 mmol) of the compound from Example 81 are reacted analogously to Example 4.

Yield: 3.1 g (57.9% of theory) $^1$H-NMR (CDCl$_3$): $\delta$=0.97 (t, 3H); 1.03 (m, 2H); 1.22 (m, 8H), 2.38 (m, 1H); 3.03 (m, 1H); 4.0 (q, 2H); 4.58 (s, 2H); 7.1 (m, 2H); 7.25 (m, 2H) ppm.

EXAMPLE 83

Ethyl 6-cyclopropyl-4-(4-fluorophenyl)-2-isopropyl-5methoxymethyl-pyridine-3-carboxylate

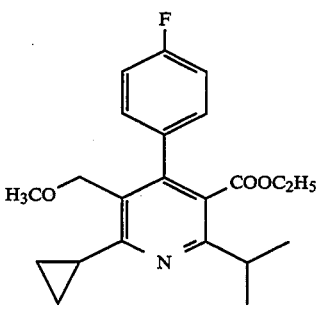

2.9 g (8 mmol) of the compound from Example 82 are reacted analogously to Example 59.

Yield: 2 g (67.4% of theory) $^1$H-NMR (CDCl$_3$): $\delta$=0.93 (t, 3H); 0.98 (m, 2H); 1.22 (d, 6H); 1.24 (m, 2H); 2.32 (m, 1H); 3.03 (m, 1H); 3.28 (s, 3H); 3.97 (q, 2H); 4.25 (s, 2H); 7.08 (m, 2H); 7.25 (m, 2H) ppm.

EXAMPLE 84

6-Cyclopropyl-4-(4-fluorophenyl)-3-hydroxy-methyl-2-isopropyl-5-methoxymethyl-pyridine

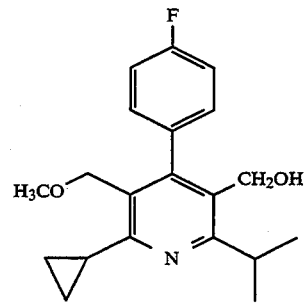

44.3 ml (15 mmol) of a 3.5 molar solution of sodium bis-(2-methoxyethoxy)-dihydroaluminate in toluene are added under nitrogen to a solution of 1.9 g (5 mmol) of the compound from Example 83 in 50 ml of dry tetrahydrofuran and the mixture is stirred for 2 hours at room temperature and 1 hour under reflux. After cooling to 0° C., 50 ml of water are cautiously added dropwise and the mixture is extracted several times with ethyl acetate. The ethyl acetate phases are combined, washed with saturated sodium chloride solution, dried over magnesium sulphate and concentrated in vacuo.

Yield: 1.6 g (97% of theory) $^1$H-NMR (CDCl$_3$): δ=0.89 (m, 2H), 1.17 (d, 6H); 1.19 (m, 2H); 2.20 (s, 1H); 3.13 (s, 3H); 3.32 (m, 1H); 4.07 (s, 2H); 4.26 (s, 2H); 7.05 (m, 2H); 7.16 (m, 2H) ppm.

EXAMPLE 85

Methyl erythro-(E)-7-[6-cyclopropyl-2-isopropyl-4-(4-fluorophenyl)-5-methoxymethyl-pyrid-3-yl]-3,5-dihydroxyhept-6-enoate

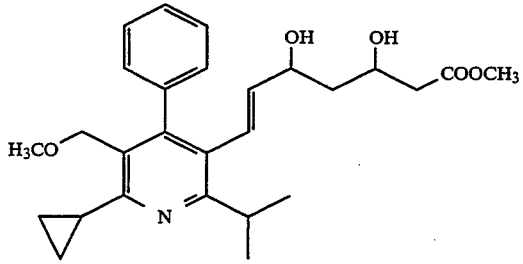

Example 85 was prepared from the compound from Example 84, in analogy to the reactions of Examples 7, 8, 9 and 10. $^1$H-NMR (CDCl$_3$): 0.95 (m, 2H); 1.17 (m, 6H); 1.22 (m, 2H); 1.40 (m, 2H); 2.25 (m, 1H); 2.44 (m, 2H); 3.22 (s, 3H); 3.23 (m, 1H); 3.73 (s, 3H); 4.07 (m, 1H); 4.18 (s, 2H); 4.28 (m, 1H); 5.22 (dd, 1H); 6.30 (d, 1H); 7.0–7.20 (m, 4H) ppm.

EXAMPLE 86

Ethyl 5-chloromethyl-2,6-diisopropyl-4-(4-fluorophenyl)pyridine-3-carboxylate

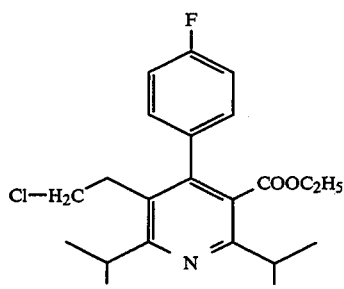

1.69 ml (20.9 mmol) of pyridine and 1.5 ml (20.9 mmol) of thionyl chloride are added successively at −5° C. to 5 g (13.9 mmol) of the compound from Example 4 dissolved in 100 m of dry tetrahydrofuran and the mixture is stirred for 15 minutes at the same temperature. The mixture is diluted using ethyl acetate and extracted several times using saturated sodium hydrogen carbonate solution, and the organic phases are dried over magnesium sulphate and concentrated in vacuo.

The residue is chromatographed on a column (silica gel 70–230 mesh, in petroleum ether/ethyl acetate 95:5).

Yield: 3.2 g (65.2% of theory) $^1$H-NMR (CDCl$_3$): δ=0.98 (t, 3 H); 1.30 (d, 6H); 1.35 (d, 6H); 3.05 (m, 1H); 3.45 (m, 1H); 3.98 (q, 2H); 4.38 (s, 2H); 7.13 (m, 2H); 7.31 (m, 2H) ppm.

EXAMPLE 87

Ethyl 2,6-diisopropyl-4-(4-fluorophenyl)-5-phenoxymethyl-pyridine-3-carboxylate

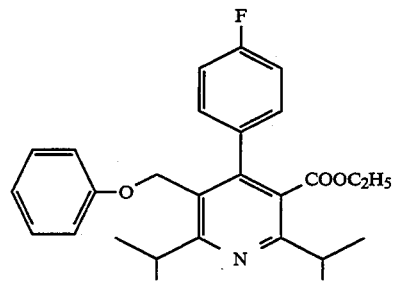

3.22 g (9.1 mmol) of the compound from Example 86 dissolved in 50 ml of absolute tetrahydrofuran are added dropwise at 0° C. to a solution of 2.11 g (18.2 mmol) of sodium phenoxide 50 ml of absolute tetrahydrofuran and the mixture is heated to reflux for 4 days. After cooling to room temperature, the mixture is diluted using 150 ml of water and extracted several times using ether. The combined organic phases are dried over magnesium sulphate and concentrated in vacuo, and the residue chromatographed on a column (silica gel 70–230 mesh, using petroleum ether/ethyl acetate 95.5).

Yield: 3.2 g (80.8% of theory) $^1$H-NMR (CDCl$_3$): δ=0.97 (t, 3H); 1.3 (d, 6H); 1.33 (d, 6H); 3.1 (m, 1H); 3.32 (m, 1H); 4.0 (q, 2H); 4.7 (s, 2H); 6.78–7.31 (m, 9H) ppm.

EXAMPLE 88

2,6-Diisopropyl-4-(4-fluorophenyl)-5-hydroxymethyl-3-phenoxymethyl-pyridine

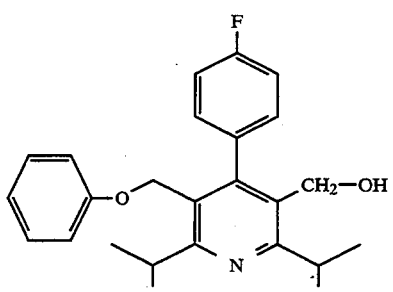

3.25 g (7.5 mmol) of the compound from Example 87 are reacted analogously to Example 60.

Yield: 2.75 g (93.2% of theory) $^1$H-NMR (CDCl$_3$): δ=1.35 (m, 12H); 3.30 (m, 1H); 3.48 (m, 1H); 4.42 (d, 2H); 4.62 (s, 2H); 6.75–7.30 (m, 9H) ppm.

ter, dried over magnesium sulphate and concentrated in vacuo.

Yield: 134 g (90% of theory) ¹H-NMR (CDCl₃): δ=0.21 (s, 9H); 1.15 (m, 2H); 1.30 (m, 6H); 2.48 (m, 1H); 4.31 (m, 2H); 4.71 (s, 1H) ppm.

EXAMPLE 94

5-Ethyl 3-(2-trimethylsilyl)-ethyl 1,4-dihydro-2,6-diisopropyl-4-(4-fluorophenyl)-pyridine-3,5-dicarboxylate

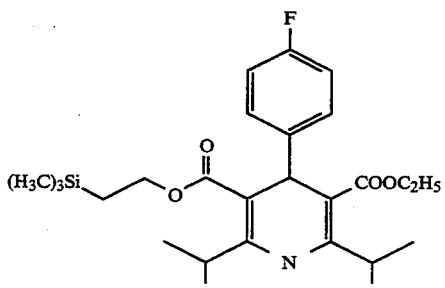

52.7 g (0.2 mol) of the compound from Example 1 are added to a solution of 45.8 g (0.2 mol) of the compound from Example 93 in 100 ml of ethylene glycol and the mixture is heated overnight to reflux. The mixture is cooled, 5 ml of concentrated hydrochloric acid is added and is again warmed to 100° C. for 30 minutes. After cooling to room temperature, it is concentrated in vacuo and the residue is taken up in ethyl acetate and extracted several times with dilute hydrochloric acid. The organic phase is subsequently washed once each with saturated sodium hydrogen carbonate solution and sodium chloride solution, dried over magnesium sulphate and concentrated in vacuo. The residue is chromatographed on a column (silica gel 70–230 mesh, using dichloromethane).

Yield: 39.2 g (41.3% of theory) ¹H-NMR (CDCl₃): δ=0.01 (s, 9H); 0.95 (m, 2H); 1.18 (m, 12H); 1.22 (t, 3H); 4.10 (m, 6H); 4.97 (s, 1H); 6.10 (s, 1H); 6.85 (m, 2H); 7.18 (m, 2H) ppm.

EXAMPLE 95

3-Ethyl 1,4-dihydro-2,6-diisopropyl-4-(4-fluorophenyl)pyridine-3,5-dicarboxylate

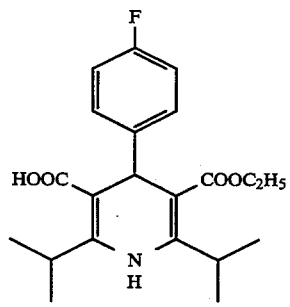

83.3 ml (83.3 mmol) of a 1 molar solution of tetrabutylammonium fluoride in tetrahydrofuran are added to a solution of 38.9 g (81.8 mmol) of the compound from Example 94 in 300 ml of dry tetrahydrofuran and the mixture is stirred for 48 hours at room temperature. After concentrating in vacuo, the residue is taken up in ether and washed three times each with dilute sodium hydroxide solution and dilute sulphuric acid, and the organic phase is dried over magnesium sulphate and concentrated again in vacuo.

Yield: 29 g (94.5% of theory) ¹H-NMR (CDCl₃): δ=1.09–1.3 (m, 15H); 4.02 (q, 2H); 4.08 (m 2H); 4.18 (m, 1H); 4.89 (s, 1H); 7.03 (m, 2H); 7.12 (m, 2H) ppm.

EXAMPLE 96

Methyl erythro-(E)-7-[2,6-diisopropyl-4-(4-fluorophenyl)-Pyrid-3-yl]-3,5-dihydroxy-hept-6-enoate

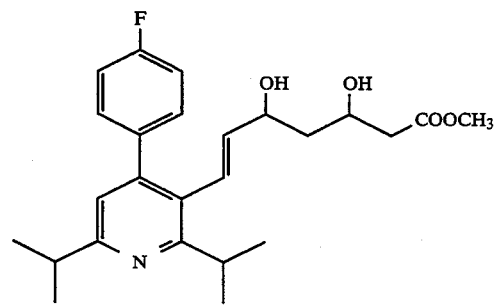

Example 96 was prepared from the compound from Example 95 in analogy to the reactions from Examples 27, 3, 29, 7, 8, 9 and 10.

¹H-NMR (CDCl₃): δ=1.28 (m, 12H); 1.50 (m, 2H); 2.47 (m, 2H); 3.05 (m, 1H); 3.35 (m, 1H); 3.72 (s, 3H); 4.13 (m, 1H); 4.38 (m, 1H); 5.31 (dd, 1H); 6.55 (d, 1H); 6.85 (s, 1H); 7.05 (m, 2H); 7.25 (m, 2H) ppm.

EXAMPLE 97

1-(4-Fluorophenyl)-4-methyl-2-phenyl-penten-3-one

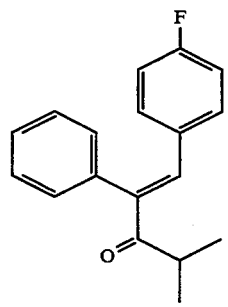

0.9 ml of piperidine is added to 24.8 g (0.2 mol) of 4-fluorobenzaldehyde and 32.4 g (0.2 mol) of benzyl isopropyl ketone in 150 ml of toluene and the mixture is heated to reflux overnight. After cooling to room temperature, the mixture is extracted several times using water and the organic phase is dried over magnesium sulphate and concentrated in vacuo. The residue is subjected to incipient distillation up to a bath temperature of 150° C. at 0.1 mbar in a high vacuum and 43.8 g of crude product are obtained in the distillation residue.

Yield: 81% of theory

EXAMPLE 89

Methyl erythro-(E)-7-[2,6-diisopropyl-4-(4-fluorophenyl)-5-phenoxymethyl-pyrid-3-yl]-3,5-dihydroxy-hept-6-enoate

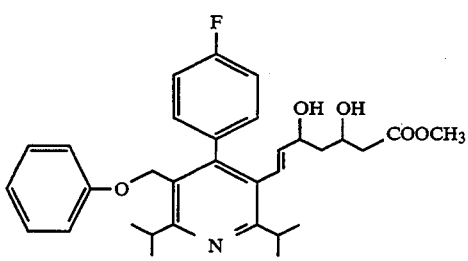

Example 89 was prepared from the compound of Example 88, in analogy to Examples 7, 8, 9 and 10.

$^1$H-NMR (CDCl$_3$): δ=1.28 (m, 6H); 1.31 (d, 6H); 1.43 (m, 2H); 2.41 (m, 2H); 3.30 (m, 2H); 3.71 (s, 3H); 4.08 (m, 1H); 4.30.(m, 1H); 4.65 (s, 2H); 5.28 (dd, 1H); 6.35 (d, 1H); 6.75–7.30 (m, 9H) ppm.

EXAMPLE 90

Ethyl 2,6-diisopropyl-4-(4-fluorophenyl)-5-(tetrahydropyran-2-yl-oxymethyl)-pyridine-3-carboxylate

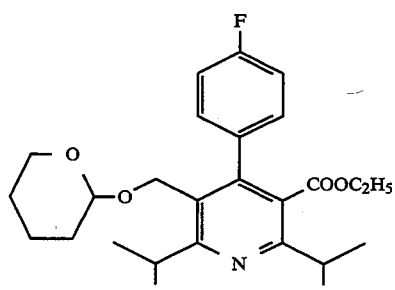

1.88 g (22.4 mmol) of dihydropyran and 0.525 g (1.49 mmol) of pyridinium p-toluene-sulphonate are added to a solution of 5.36 g (14.9 mmol) of the compound from Example 4 in 100 ml of dry dichloromethane and the mixture is heated to reflux for 48 hours. After cooling to room temperature, the mixture is diluted using dichloromethane and extracted several times using water. The organic phase is dried over magnesium sulphate and concentrated in vacuo, and the residue is chromatographed on a column (silica gel 70–230 mesh, using dichloromethane).

Yield: 4.4 g (66.7% of theory) $^1$H-NMR (CDCl$_3$): δ=0.98 (t, 3H); 1.31 (m, 12H); 1.40–1.80 (m, 6H); 3.05 (m, 1H); 3.43 (m, 2H); 3.61 (m, 1H); 3.98 (q, 2H); 4.05 (d, 1H); 4.45 (m, 1H); 4.55 (d, 1H); 7.05 (m, 2H); 7.25 (m, 2H) ppm.

EXAMPLE 91

2,6-Diisopropyl-4-(4-fluorophenyl)-3-hydroxymethyl-5-(tetrahydropyran-2-yl-oxymethyl)-pyridine

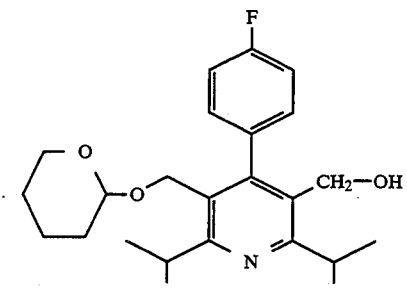

4.4 g (9.9 mmol) of the compound from Example 90 are reacted analogously to Example 60.

Yield: 2.5 g (63.5% of theory) $^1$H-NMR (CDCl$_3$): δ=1.32 (m, 12H); 1.40–1.80 (m, 6H); 3.40 (m, 3H); 3.57 (m, 1H); 3.95 (d, 1H); 4.35 (m, 3H); 4.5 (d, 1H); 7.11 (m, 2H); 7.25 (m, 2H) ppm.

EXAMPLE 92

Methyl erythro-(E)-7-[2,6-diisopropyl-4-(4-fluorophenyl)-5-(tetrahydropyran-2-yl-oxymethyl)-pyrid-3-y]-3,5-dihydroxy-hept-6-enoate

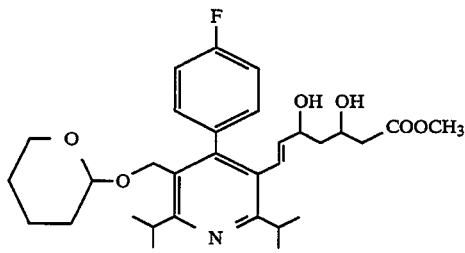

Example 92 was prepared from the compound from Example 91, in analogy to the reactions from Examples 7, 8, 9 and 10.

$^1$H-NMR (CDCl$_3$): δ=1.20–1.80 (m, 2OH); 2.43 (m, 2H); 3.32 (m, 1H); 3.41 (m, 2H); 3.58 (m, 1H); 3.72 (s, 3H); 3.98 (d, 1H); 4.08 (m, 1H); 4.29 (m, 1H); 4.43 (m, 1H); 4.54 (d, 1H); 5.28 (dd, 1H); 6.31 (d, 1H); 7.10 (m, 4H) ppm.

EXAMPLE 93

2-(Trimethylsilyl)-ethyl 3-amino-4-methyl-pent-2-enoate

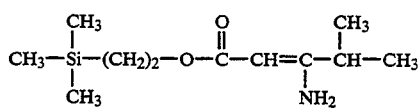

3 g of p-toluenesulphonic acid are added to 150 g (0.65 mol) of 2-(trimethylsilyl)ethyl-isobuturyl-acetate in 700 m l of toluene and the mixture is saturated using ammonia gas at room temperature. It is allowed to stand overnight and subsequently heated to reflux for 8 hours, ammonia gas being introduced continuously. After cooling to room temperature, the mixture is filtered and the toluene solution is extracted several times with wa-

EXAMPLE 98

Ethyl 1,4-dihydro-2,6-diisopropyl-4-(4-fluorophenyl)-5-phenyl-pyridine-3-carboxylate

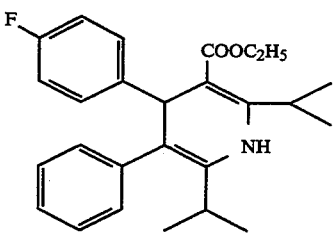

2.86 ml (50 mmol) of glacial acetic acid are added to 13.45 g (50 mmol) of the compound from Example 97 and 17.4 g (100 ml) of ethyl 3-amino-4-methyl-pent-2-enoate in 80 ml of ethylene glycol and the mixture is heated to reflux overnight. After cooling to room temperature, it is concentrated vacuo and the residue is dissolved in dichloromethane and extracted several times using water. The organic phase is dried over magnesium sulphate and concentrated in vacuo, and the residue is taken up in ethyl acetate. After extracting using 10% strength hydrochloric acid, water and saturated sodium hydrogen carbonate solution, the organic phase is dried again and concentrated, and the residue is chromatographed on a column (silica gel 70–230 mesh, using ethyl acetate/petroleum ether)).

Yield: 2.3 g (11.3% of theory) $^1$H-NMR (CDCl$_3$): δ=1.1 (m, 9H); 1.25 (m, 6H); 2.70 (m, 1H); 3.90–4.40 (m, 3H); 4.55 (s, 1H); 5.75 (s, 1H); 6.80–7.30 (m, 9H) ppm.

EXAMPLE 99

Methyl erythro-(E)-7-[2,6-diisopropyl-4-(4-fluorophenyl)-5-phenyl-pyrid-3-yl]-3,5-dihydroxy-hept-6-enoate

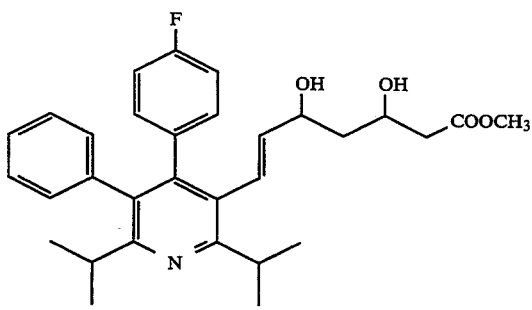

Example 99 was prepared from the compound from Example 98 in analogy to the reactions of Examples 3, 29, 7, 8, 9 and 10.

$^1$H-NMR (CDCl$_3$): δ=1.18 (d, 6H); 1.32 (m, 6H); 1.42 (m, 2H); 2.40 (m, 2H); 2.70 (d, 1H); 2.88 (m, 1H); 3.38 (m, 1H); 3.48 (d, 1H); 3.71 (s, 3H); 4.05 (m, 1H); 4.30 (m, 1H); 5.30 (dd, 1H); 6.39 (d, 1H); 6.70–7.20 (m, 9H) ppm.

EXAMPLE 100

Methyl erythro-(E)-7-[2,6-diisopropyl-4-(4-fluorophenyl)-5-carboxyethyl-pyrid-3-yl]-3,5-dihydroxy-hept-6-enoate

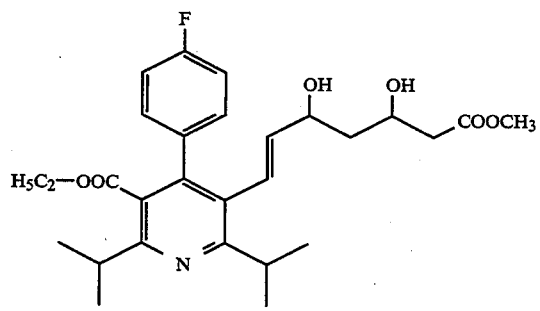

Example 100 was prepared from the compound from Example 4 in analogy to the reactions of Examples 7, 8, 69 and 10.

$^1$H-NMR (CDCl$_3$): δ=0.98 (t, 3H); 1.25 (m, 6H; 1.32 (d, 6H); 1.45 (m, 2H); 2.42 (m, 2H); 3.05 (m, 1H); 3.32 (m, 1H); 3.72 (s, 3H); 3.98 (q, 2H); 4.10 (m, 1H); 4.32 (m, 1H); 5.29 (dd, 1H); 6.38 (d, 1H); 7.02 (m, 2H); 7.12 (m, 2H) ppm.

EXAMPLE 101

Ethyl 1,4-dihydro-2,6-diisopropyl-4-(4-fluorophenyl)-5-morpholinocarbonyl-pyridine-3-carboxylate

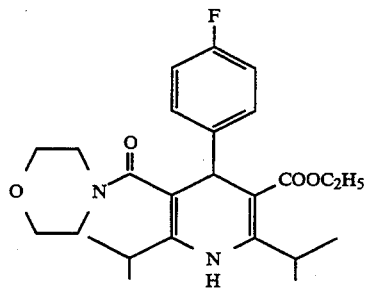

1.05 g (6.5 mmol) of N,N'-carbonylimidazole are added under a nitrogen atmosphere to 1.875 g (5 mmol) of the compound from Example 95 dissolved in 20 ml of dry tetrahydrofuran and the mixture is stirred for 30 minutes at room temperature. It is subsequently heated to reflux for 30 minutes, a solution of 0.87 ml (10 mmol) of morpholine in 5 ml of dry tetrahydrofuran is added and it is heated to boiling for a further 2 hours. After cooling to room temperature, the mixture is concentrated in vacuo and the residue is taken up in dichloromethane and washed successively with 1N hydrochloric acid, 1N sodium hydroxide solution and water. The organic phase is dried over magnesium sulphate and concentrated in vacuo, and the crystalline residue is dried in a desiccator.

Yield: 1.96 g (88% of theory) $^1$H-NMR (CDCl$_3$): δ=1.0–1.28 (m, 15H); 3.20–4.40 (complex region, 12H); 4.70 (s, 1H); 5.50 (s, 1H); 6.90 (m, 2H); 7.20 (m, 2H) ppm.

EXAMPLE 102

3-Ethyl 2,6-diisopropyl-4-(4-fluorophenyl)-pyridine-3,5-dicarboxylate 5-morpholide

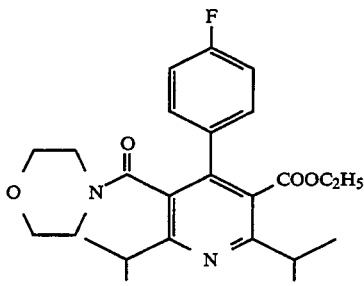

9 g (21.5 mmol) of the compound from Example 101 are reacted analogously to Example 3.

Yield: 7.6 g (80% of theory) $^1$H-NMR (CDCl$_3$): δ=0.95 (t, 3H); 1.25 (m, 6H); 1.35 (m, 6H); 2.70–3.80 (complex region, 10H); 4.0 (m, 2H); 7.0–7.50 (m, 4H) ppm.

EXAMPLE 103

Methyl erythro-(E)-7-[2,6-diisopropyl-4-(4-fluorophenyl)-5-morpholinocarbonyl-pyrid-3-yl]-3,5-dihydroxy-hept-6-enoate

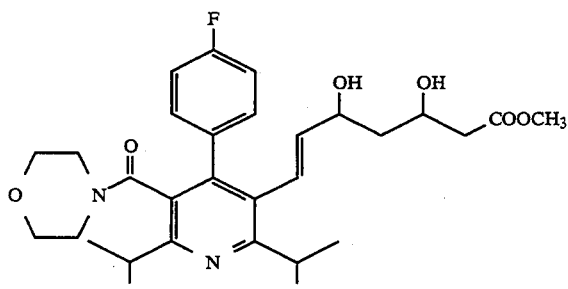

Example 103 was prepared from the compound from Example 102 in analogy to the reactions of Examples 29, 7, 8, 9 and 10.

$^1$H-NMR (CDCl$_3$): δ=1.10–1.50 (complex region, 14H); 2.40 (m, 2H); 2.80–3.65 (complex region, 10H); 3.75 (s, 3H); 4.10 (m, 1H); 4.35 (m, 1H); 5.25 (m, 1H); 6.45 (dd, 1H); 6.95–7.50 (m, 4H) ppm.

EXAMPLE 104

2,6-Diisopropyl-4-(4-fluorophenyl)-3-hydroxymethyl-5-morpholinomethyl-pyridine

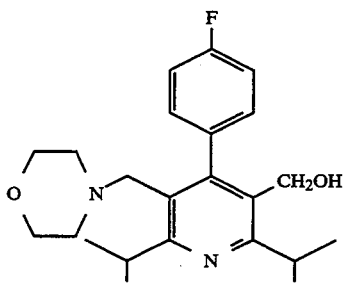

20.6 ml (31 mmol) of diisobutylaluminum hydride (1M in toluene) are added under a nitrogen atmosphere at −78° C. to 1.37 g (3.1 mmol) of the compound from Example 102 dissolved in 30 ml of dry toluene and the mixture is stirred for 1 hour at the same temperature. The mixture is subsequently stirred for 48 hours at room temperature, hydrolyzed using 20% strength potassium hydroxide solution with ice-cooling and extracted several times with toluene. The organic phase is dried over magnesium sulphate, concentrated in vacuo and dried in a desiccator. Yield: 1.04 g (87% of theory)

$^1$H-NMR (CDCl$_3$): δ=1.28 (d, 6H); 1.32 (d, 6H); 2.15 (m, 4H); 3.18 (s, 2H); 3.45 (m, 2H); 3.52 (m, 4H); 4.32 (d, 2H); 7.05–7.20 (m, 4H) ppm.

EXAMPLE 105

Methyl erythro-(E)-7-[2,6-diisopropyl-4-(4-fluorophenyl)-5-morpholinomethyl-pyrid-3-yl]-3,5-dihydroxy-hept-6-enoate

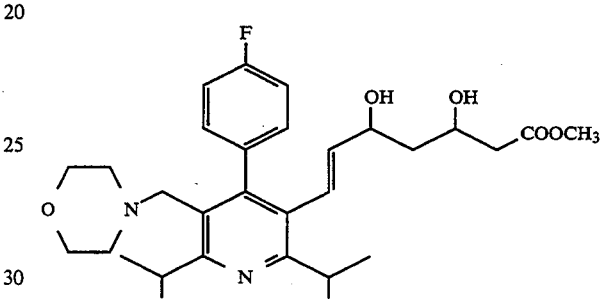

Example 105 was prepared from the compound from Example 104 in analogy to the reactions of Examples 7, 8, 9 and 10.

$^1$H-NMR (CDCl$_3$): δ=1.25 (m, 12H); 1.40 (m, 2H); 2.20 (m, 4H); 2.45 (m, 2H); 3.20 (s, 2H); 3.30 (m, 1H); 3.45 (m, 1H); 3.55 (m, 4H); 3.75 (s, 3H); 4.10 (m, 1H); 4.30 (m, 1H); 5.30 (dd, 1H); 6.25 (d, 1H); 7.0–7.20 (m, 4H) ppm.

EXAMPLE 106

Methyl erythro-(E)-7-(2,6-diisopropyl)-4-(4-fluorophenyl)-5-iodomethyl-pyrid-3-yl]-3,5-dihydroxy-hept-6-enoate

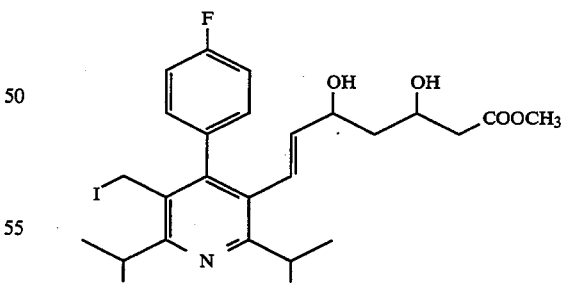

80 mg (0.1514 mmol) of the compound from Example 105 are dissolved in 5 ml of methyl iodide and the mixture is stirred 3 hours at 30° C. and overnight at 60° C. with the exclusion of light. The mixture is concentrated in vacuo and dried in a desiccator over phosphorus pentoxide. 120 mg of crude product are obtained.

$^1$H-NMR (CDCl$_3$): δ=1.20–1.70 (complex region, 14H); 2.45 (m, 2H); 3.30 (m, 2H); 3.75 (s, 3H); 4.05 (m, 1H); 4.20 (s, 2H); 4.30 (m, 1H); 5.30 (dd, 1H); 6.25 (d, 1H); 7.0–7.25 (m, 4H) ppm.

EXAMPLE 107

Methyl erythro-(E)-7-[2,6-diisopropyl-4-(4-fluorophenyl)-5-benzylthio-methyl-pyrid-3-yl]-3,5-dihydroxy-hept-6-enoate

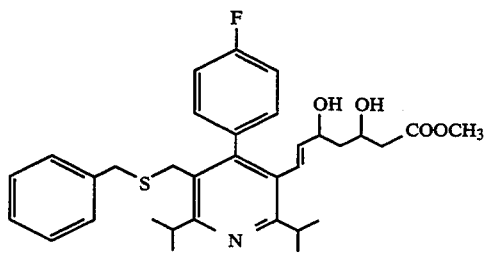

22.3 μl (0.19 mmol) of benzyl mercaptan and 32.7 μ(0.237 mmol) of triethylamine are added successively under a nitrogen atmosphere to 90 mg (0.158 mmol) of the compound from Example 106 dissolved in 2 ml of dry dichloromethane and the mixture is stirred overnight at room temperature. The mixture is diluted using dichloromethane and extracted several times using water. After drying the organic phase over magnesium sulphate and concentrating in vacuo, the residue is chromatographed on a column (silica gel 70–230 mesh, using ethyl acetate/petroleum ether 1:1).

Yield: 20 mg (22.4% of theory) $^1$H-NMR (CDCl$_3$): δ=1.23 (m, 12H); 1.4 (m, 2H); 2.40 (m, 2H); 3.20 (m, 2H); 3.28 (s, 2H) 3.55 (s, 2H); 3.73 (s, 3H); 4.05 (m, 1H); 4.25 (m, 1H); 5.25 (dd, 1H); 6.25 (d, 1H); 6.90–7.28 (m, 9H) ppm.

EXAMPLE 108

4-{[5-(3,5-Dihydroxy-6-methoxycarbonylhex-1-enyl)-2,6-diisopropyl-4-(4-fluorophenyl)]-pyrid-3-yl}methyl-morpholine oxide

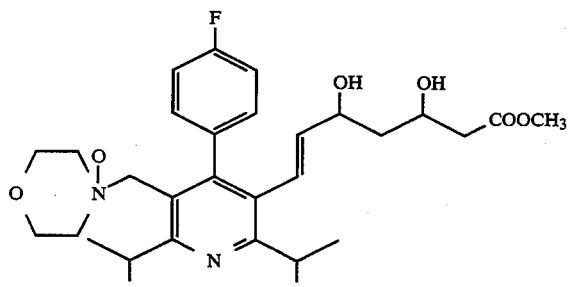

52 mg (0.303 mmol) of m-chloroperbenzoic acid are added to 80 mg (0.1515 mmol) of the compound from Example 105 dissolved in 3 ml of dry dichloromethane and the mixture is stirred for 1 hour at room temperature. The mixture is then washed successively with potassium iodide solution, sodium thiosulphate solution and sodium hydrogen carbonate solution, and the organic phase is dried over magnesium sulphate and concentrated in vacuo.

Yield: 60 mg (73% of theory) $^1$H-NMR (CDCl$_3$): δ=1.10–1.55 (complex region, 14H); 2.45 (m, 2H); 2.70–3.70 (complex region, 10H); 3.75 (s, 3H); 4.0 (m, 1H); 4.10 (m, 1H); 4.30 (m, 2H); 5.25 (dd, 1H); 6.25 (d, 1H); 7.0–7.30 (m, 4H) ppm.

EXAMPLE 109

Ethyl 2-(4-fluorobenzoyl)-4-methyl-pent-2-enoate

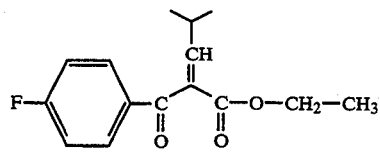

A solution of 210 g (1 mol) of ethyl 4-fluorobenzoylacetate and 144 g (2 mol) of 2-methylpropanal are stirred overnight at 50° C. with 7 ml of piperidine and 5 ml of acetic acid in 100 ml of isopropanol. After reaction is complete, the batch is concentrated at about 15 Torr and the crude product (270 g, about 85%) is reacted without further purification.

EXAMPLE 110

3-Ethoxycarbonyl-2-(4-fluorophenyl)-1,4-dihydro-4-isopropyl-6-methyl-5-methoxycarbonyl-pyridine

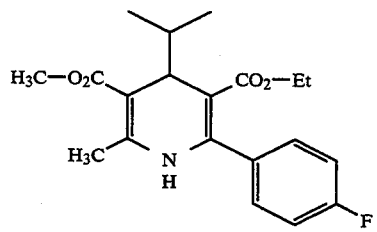

62.9 g (0.2 mol) of the compound from Example 109 and 21.9 g (0.19 mol) of methyl 3-amino-crotonate are heated to reflux overnight in 200 ml of ethylene glycol. The mixture is extracted three times using ether, the combined organic phases are extracted, using 2N hydrochloric acid and saturated sodium chloride solution, dried over magnesium sulphate and concentrated to dryness. The residue (65 g) is chromatographed in two portions on 750 g of silica gel each time (230–400 mesh) in a column (7.5 cmφ) using petroleum ether/ethyl acetate 10:1>5:1.

Yield: 21.5 g (31%) of yellow crystals M.p.: 109° C.

EXAMPLE 111

3-Ethoxycarbonyl-2-(4-fluorophenyl)-4-isopropyl-5-methoxycarbonyl-6-methyl-pyridine

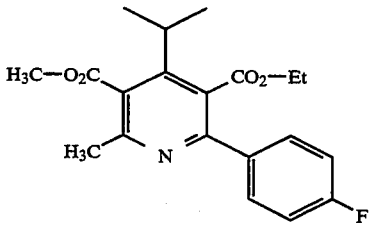

Analogously to Example 3, Example 111 was prepared from 14.9 g (14.5 mmol) of the compound from Example 110.

Yield: 15.2 g (102%) of crude product, a colourless oil which is reacted without further purification. $^1$H-NMR (CDCl$_3$): δ=1.02 (t, 3H, CH$_2$CH$_3$); 1.33 (d, 6H, CH(CH$_3$)$_2$); 2.55 (S, 3H, 6-CH$_3$); 3.15 (sept, 1H, CH(CH$_3$)$_2$); 3.95 (s, 3H, O—CH$_3$); 4.08 (q, 2H, CH$_2$—CH$_3$); 7.1 (m, 2H, 3'-H); 7.55 (m, 2H, 2'-H); ppm.

EXAMPLE 112

3-Ethoxycarbonyl-2-(4-fluorophenyl)-5-hydroxymethyl-4-isopropyl-6-methyl-pyridine

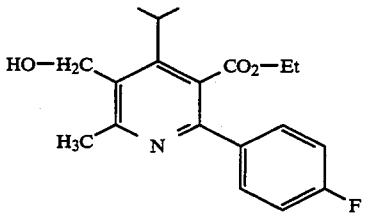

Analogously to Example 4, Example 112 was prepared from 10 g (27.8 mmol) of the compound from Example 111.

Yield: 4.53 g (49% of theory) of yellowish crystals M.p.: 113° C.

EXAMPLE 113

Methyl erythro-(E)-7-[5-tert.butyldimethyl-silyloxymethyl-2-(4-fluorophenyl)-4-isopropyl-6-methyl-pyrid-3-yl]-3,5-dihydroxy-hept-6-enoate

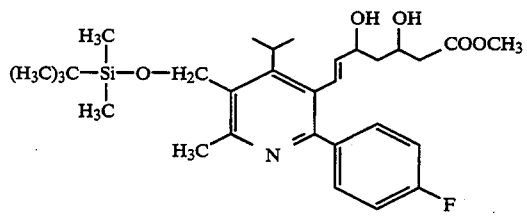

Example 113 was prepared from the compound from Example 112 in analogy to the reactions from Examples 5, 6, 7, 8, 9 and 10.

A colourless foam was obtained. $^1$H-NMR (CDCl$_3$): δ=0.2 (s, 6H, Si(CH$_3$)$_2$); 9.13 (s, 9H, Si—C(CH$_3$)$_3$); 1.3 (m, 8H, CH(CH$_3$)$_2$+CH(OH)—CH$_2$—CH(OH)); 2.4 (m, 2H, CH$_2$—COOCH$_3$); 2.65 (s, 3H, 6'-CH$_3$); 3.1 (b, 1H, OH); 3.65 (b, 1H, OH); 3.7 (s, 3H, O—CH$_3$); 4.1 (m, 1H, CH—OH); 4.35 (m, 1H, CH—OH); 4.8 (s, 2H, 5'-CH$_2$); 5.15 (dd, 1H, 6'-H); 6.7 (d, 1H, 7-H); 7.0 (m, 2H, 3''-H); 7.35 (m, 2H, 2''-H) ppm.

EXAMPLE 114

Methyl erythro-(E)-7-[2-(4-fluorophenyl)-5-hydroxymethyl-4-isopropyl-6-methyl-pyrid-3-yl]-3,5-dihydroxy-hept-6-enoate

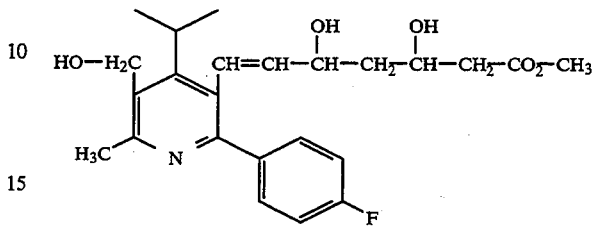

223 g (0.4 mmol) of the compound from Example 113 are stirred at room temperature for 2 days with 0.5 ml of 1N hydrochloric acid in 5 ml of methanol. Concentrating and column chromatography on 18 g of silica gel 230–400 mesh, 2 cm, chloroform/methanol 10:1, give 100 mg (57% of theory) of colorless foam.

$^1$H-NMR (CDCl$_3$): δ=1.2–1.45 (m, 8H, CH(CH$_3$)$_2$+CH(OH)—CH$_2$—CH(OH)); 2.4 (m, 2H, CH$_2$—COOCH$_3$); 2.7 (s, 3H, 6'-Ch$_3$); 3.1 (b, 1H, OH); 3.6 (m, 2H, CH(CH$_3$)$_2$+OH); 3.7 (s, 3H, O—CH$_3$); 4.1 (m, 1H, CHOH); 4.35 (m, 1H, CH—OH); 4.88 (s, 2H, 5'-CH$_2$); 5.18 (dd, 1H, 6'-H); 6.7 (d, 1H, 7-H); 7.03 (m, 2H, 3''-H); 7.38 (m, 2H, 2''-H) ppm.

EXAMPLE 115

Methyl erythro-(E)-7-[5-benzyloxymethyl-2-(4-fluorophennyl)-4-isopropyl-6-methyl-pyrid-3-yl]-3,5-dihydroxy-hept-6-enoate

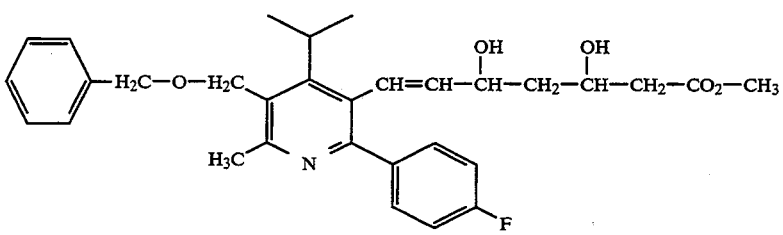

Example 115 was prepared from the compound from Example 112 in analogy to the reactions of Examples 12, 6, 7, 8, 9 and 10. A colorless foam was obtained.

$^1$H-NMR (CDCl$_3$): δ=1.2–1.45 (m, 8H, CH(CH$_3$)$_2$+CH(OH)—CH$_2$—CH(OH); 2.4 (m, 2H, CH$_2$—COOCH$_3$); 2.6 (S, 3H, 6'-CH$_3$); 3.05 (b, 1H, OH); 3.5 (m, 2H, CH(CH$_3$)$_2$+OH); 3.72 (s, 3H; O—CH$_3$); 4.1 (m, 1H, CH—OH); 4.35 (m, 1H, CHOH); 4.62 (s, 2H, O—CH$_2$); 4.66 (s,2H,OCH$_2$); 5.15 (dd, 7H, 6-H); 6.2 (d, 1H, 7-H); 7.12 (m, 2H, 3''-H); 7.3–7.45 (m, 7H, aromatic-H) ppm.

EXAMPLE 116

Methyl erythro-(E)-7-[2-(4-fluorophenyl)-4-isopropyl-5-methoxymethyl-6-methyl-pyrid-3-yl]-3,5-dihydroxy-hept-6-enoate

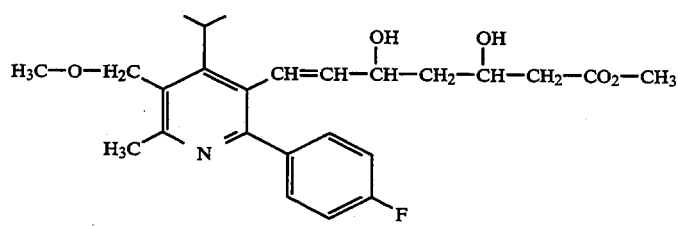

Example 116 was prepared from the compound from Example 112 in analogy to the reactions of Examples 59, 6, 7, 8, 9 and 10. A colorless foam was obtained.
¹H-NMR (CDCl₃): δ=1.2–1.45 (m, 8H, CH(CH₃)₂+CH(OH)—CH₂—CH(OH); 2.4 (m, 2H, CH₂—COOCH₃); 2.63 (s, 3H, 66′-CH₃); 3.15 (b, 1H, OH); 3.5 (m, 4H, O—CH₃+CH(CH₃)₂); 3.62 (b, 1H, OH); 3.71 (s, 3H, COOCH₃); 4.1 (m, 1H, CH—OH); 4.35 (m, 1H, CH—OH); 4.55 (s, 2H, O—CH₂); 5.15 (dd, 1H, 6-H); 6.65 (d, 1H, 7-H); 7.0 (m, 2H, 3″-H); 7.35 (m, 2H, 2″-H) ppm.

EXAMPLE 117

3-Benzyloxymethyl-4-(4-fluorophenyl)-6-isopropyl-5-(methyl-erythro-(E)-3,5-dihydroxy-hept-6-enoat-7-yl)pyridine N-oxide

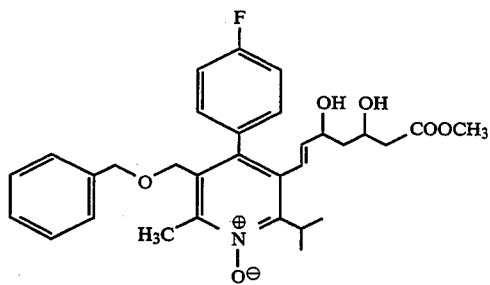

863 mg (4 mmol) of 80% strength meta-chloroperoxybenzoic acid are added to 208.4 mg (0.4 mmol) of the compound from Example 64 dissolved in 10 ml of dichloromethane and the mixture is stirred overnight at room temperature. After concentrating in vacuo, the residue is chromatographed on a column (silica gel 70–230 mesh, using dichloromethane/methanol 96:4).
Yield: 107 mg (50% of theory) ¹H-NMR (CDCl₃): δ=1.20–1.60 (m, 2H); 1.45 (d, 6H); 2.40 (m, 2H); 2.58 (s, 3H); 3.62 (m, 1H); 3.72 (s, 3H); 4.08 (m, 1H); 4 .12 (s, 2H); 4.30 (m, 1H); 4.38 (s, 2H); 5.23 (dd, 1H); 6.28 (d, 1H); 7.00–7.40 (m, 9H) ppm.

EXAMPLE 118

3-Amino-4′-fluoro-cinnamonitrile

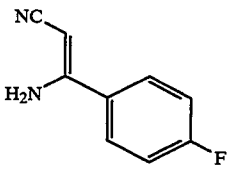

A solution of 41 g (1 mol) of acetonitrile, 135 g (1.1 mol) of 4-fluorobenzonitrile and 7.4 g (0.1 mol) of tert.-butanol in 300 ml of tetrahydrofuran are added dropwise at room temperature with stirring to a suspension of 30 g (1 mol) of sodium hydride in 300 ml of p.a. tetrahydrofuran and the mixture is heated to about 30° C. until the reaction starts. The remainder is added dropwise at 35°–40° C. with external cooling and the mixture is subsequently heated under reflux for 30 minutes. Then 500 ml of water are cautiously added dropwise, the aqueous phase is extracted twice using ethyl acetate and the combined organic phases are dried over sodium sulphate. After stripping off the solvent, a crop of crystals remains which is stirred with ether and filtered off with suction (65.1 g). The filtrate is concentrated to dryness on a rotary evaporator, filtered over 300 g of silica gel using toluene and crystallized from ether as above (46.3 g).
Yield: 111.4 g (69% of theory) of colorless crystals M.p.: 108° C.

EXAMPLE 119

E/Z-4-Ethoxycarbonyl-2,6-dimethyl-hept-4-en-3-one

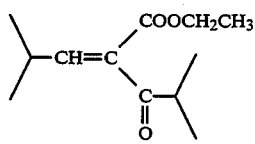

158 g (1 mol) of ethyl isobutyrylacetate, 108 g (1.5 mol) of isobutyraldehyde, 8.75 ml of piperidine and 6.25 ml of acetic acid are stirred at 500° C. for 20 h in 400 ml of isopropanol. Volatile components are stripped off in a water pump vacuum and the residue is subsequently distilled in a high vacuum.
Yield: 145 g (68% of theory) of col. oil, m.p.=60° C., 0.2 mbar

EXAMPLE 120

3-Cyano-5-ethoxycarbonyl-2-(4-fluorophenyl)-1,4-dihydro-4,6-diisopropyl-pyridine

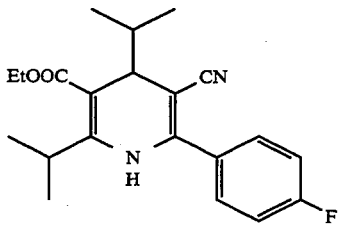

26.7 g (165 mmol) of the compound from Example 118 and 35 g (165 mmol) of E/Z-4-ethoxycarbonyl-2,6dimethyl-hept-4-en-3-one from Example 119 are heated at a bath temperature of 200° C. for 4 h. A further 17 g (80 mmol) of the latter components is then added and the mixture is heated overnight. The residue is prepurified over 450 g of silica gel (230–400 mesh) using 3 l of toluene/petroleum ether (1:1), 3 l of toluene and 2 l of toluene/ethyl acetate (10:1). 5.7 g (9.7%) of yellowish crystals (m.p: 140° C.) crystallize from ether from the concentrated filtrate. The filtrate is chromatographed once again on 750 g of silica gel using petroleum ether/ethyl acetate (10:1). Two zones are obtained:

1. 7.4 g (12.5%) of colorless crystals of m.p.: 141° C. (from ether/petroleum ether) and as a by-product
2. 3,5-bis-cyano-2,6-bis-4-fluorophenyl-1,4-dihydro-4-isopropyl-pyridine [2.2 g (3.7%) of yellowish crystals of m.p.: 227°–228° C., from ether/petroleum ether].

Total yield: 13.1 g (22% of theory) $^1$H-NMR (CDCl$_3$): δ=0.93 (d, 3H); 1.02 (d, 3H); 1.2 (m, 6H); 1.3 (t, 3H); 1.8 (m, 1H); 3.6 (d, 1H); 4.2 (m, 2H); 6.15 (b, 1H); 7.2 (t, 2H); 7.53 (m, 2H) ppm.

EXAMPLE 121

3-Cyano-5-ethoxycarbonyl-2-(4-fluorophenyl)-4,6-diisopropyl-pyridine

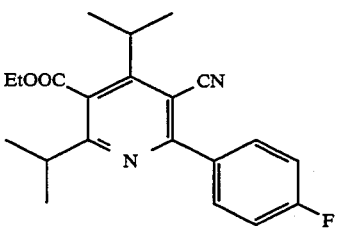

The preparation takes place from 16.0 g (45 mmol) of the compound from Example 120 analogously to the instruction s of Example 3.

Yield: 14.5 g (91% of theory) M.p.: 82° C.

EXAMPLE 122

2-(4-Fluorophenyl)-3-formyl-5-hydroxymethyl-4,6-diisopropyl-pyridine

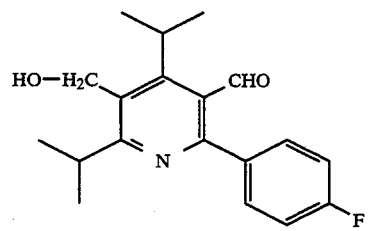

110 ml (165 mmol) of a 1.5M solution of diisobutylaluminum hydride in toluene are added dropwise under argon at −78° C. to −75° C. to a solution of 14.5 g (41 mmol) of the compound from Example 121 in 320 ml of toluene p.a. and the mixture is stirred for 2 h at this temperature and subsequently for 1 h at −20° C. 350 ml of water and 250 ml of ethyl acetate are then added dropwise, the mixture is filtered with suction using kieselguhr and washed with ethyl acetate, and the aqueous phase is extracted using 300 ml of ethyl acetate. The combined organic phases are washed with sodium chloride solution, dried over sodium sulphate and concentrated. Column chromatography on 500 g of silica gel (230-400 mesh) using petroleum ether/ethyl acetate (5:1) and recrystallization from ether/petroleum ether yields 5.4 g (42% of theory) of yellowish crystals of m.p.: 147° C.

EXAMPLE 123

(E)-3-[2-(4-Fluorophenyl)-5-hydroxymethyl-4,6-diisopropyl-pyridin-3-yl]-prop-2-enal

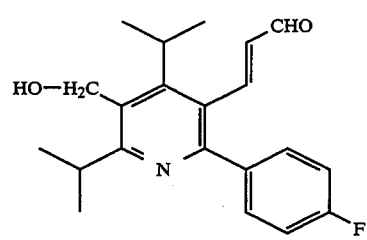

The preparation takes place analogously to Example 8 from 200 mg (6.6 mmol) of 80% pure sodium hydride, 0.86 g (3.3 mmol) of diethyl 2-(cyclohexylamino)vinylphosphonate and 0.94 g (3 mmol) of the compound from Example 122.

Yield: 0.46 g (45% of theory) M.p.: 210° C.

EXAMPLE 124

Methyl (E)-7-[2-(4-fluorophenyl)-5-hydroxymethyl-4,6-diisopropyl-pyridin-3-yl]-5-hydroxy-3-oxo-hept-6-enoate

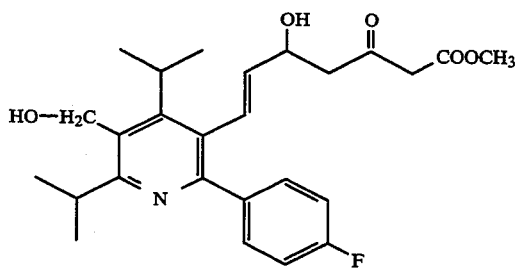

0.5 ml (4.5 mmol) of methyl acetoacetate are added dropwise at 0° C.–5° C. under argon to a suspension of 0.15 g(5 mmol) of 80% pure sodium hydride in 6.5 ml of tetrahydrofuran p.a. After 15 minutes in each case, 3.65 ml (6 mmol) of 15% strength butyllithium in hexane are first added dropwise at 0° C. during the course of 10 minutes then a solution of 1.01 g (4.5 mmol) of dry zinc bromide in 4.5 ml of tetrahydrofuran and finally 0.51 g (1.5 mmol) of the compound from Example 123. The mixture is stirred overnight at room temperature, saturated ammonium chloride solution is added slowly, the aqueous phase is extracted using ethyl acetate, and the combined organic phases are washed using saturated sodium chloride solution, dried over sodium sulphate and concentrated. After column chromatography ($\phi$3 cm) on 20 g of silica gel (230–400 mesh) using petroleum ether-ethyl acetate (1:1), 0.17 g (25% of theory) of yellowish oil is obtained. $R_f=0.35$ (petroleum ether-ethyl acetate (1:1)).

EXAMPLE 125

Methyl erythro-(E)-7-[2-(4-fluorophenyl)-5-hydroxymethyl-4,6-diisopropyl-pyridin-3-yl]-3,5-dihydroxy-hept-6-enoate

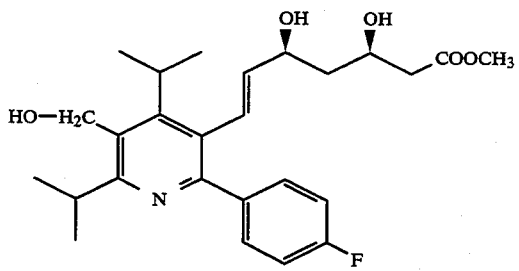

The preparation takes place analogously to the instructions for Example 10 from 0.15 g (0.33 mmol) of the compound from Example 124.

Yield: 85 mg (56% of theory) $^1$H-NMR (CDCl$_3$): $\delta=1.25$–1.6 (m, 14H, CH(OH)—CH$_2$—CH(OH)+CH(CH$_3$)$_2$); 2.45 (m, 2H, CH$_2$—COOCH$_3$); 3.1 (b, 1H, OH); 3.45–3.7 (m, 3H, CH(CH$_3$)$_2$+OH); 3.7 (s, 3H), OCH$_3$); 4.1 (m, 1H, CH(OH); 4.35 (m, 1H, CH(OH); 4.85 (s, 2H, CH$_2$—OH) 5.7 (dd, 1H, 6-H); 6.25 (d, 1 H, 7-H); 7.05 (t, 2H, 3''-H); 7.45 (m, 2H, 2''-H) ppm.

EXAMPLE 126

5-Ethoxycarbonyl-2-(4-fluorophenyl)-3-formyl-4,6-diisopropyl-pyridine

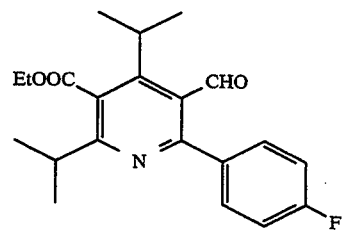

The preparation takes place analogously to the process for Example 122 from 3.5 g (10 mmol) of the compound from Example 121 and 35 ml of a 1M solution of diisobutylaluminum hydride in toluene, the temperature being kept at $-75°$ C. for 1.5 h, the mixture then being warmed to $-30°$ C. before water is added.

Yield: 0.8 g (22% of theory) of colorless crystals M.p.: 88° C. (from petroleum ether)

EXAMPLE 127

(E)-3-[5-Ethoxycarbonyl-2-(4-fluorophenyl)-4,6-diisopropyl-pyridin-3-yl]-prop-2-enal

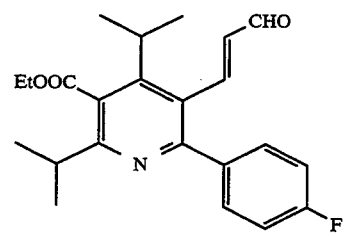

The preparation takes place analogously to the instructions for Example 8 from 1.25 g (3.5 mmol) of the compound from Example 126.

Yield: 0.17 g (72% of theory) of colorless oil $R_f=0.35$ (petroleum ether-ethyl acetate (5:1)).

EXAMPLE 128

Methyl (E)-7-[5-ethoxycarbonyl-2-(4-fluorophenyl)-4,6-diisopropyl-pyridin-3-yl]-5-hydroxy-3-oxo-hept-6-enoate

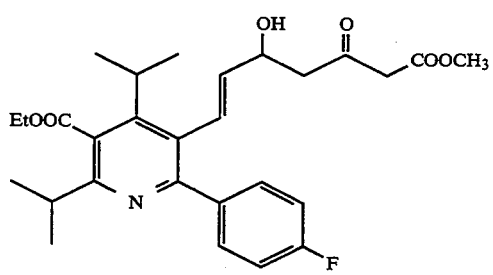

The preparation takes place analogously to the instructions for Example 123 from 0.95 g (2.48 mmol) of the compound from Example 127.

Yield: 0.83 g (67% of theory) of colorless oil $R_f=0.27$ (petroleum ether-ethyl acetate (2:1))

EXAMPLE 129

Methyl erythro-(E)-7-[5-ethoxycarbonyl-2-(4-fluorophenyl)-4,6-diisopropyl-pyridin-3-yl]-3,5-dihydroxy-hept-6-enoate

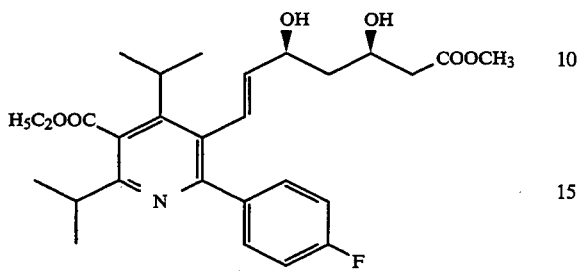

The preparation takes place analogously to the instructions for Example 10 from 0.89 g (1.66 mmol) of the compound from Example 128.

Yield: 0.65 g (78% of theory) of colorless oil $^1$H-NMR.(CDCl$_3$): δ=1.25-1.5 (m, 17H, CH(CH$_3$)$_2$+CH$_2$—CH$_3$+CH(OH)—CH$_2$); 2.42 (m, 2H, CH$_2$—COOCH$_3$); 2.95 (m, 1H, CH(CH$_3$)$_2$); 3.15 (b, 1H, OH); 3.2 (m 1H, CH(CH$_3$)$_2$); 3.6 (b, 1H, OH); 3.7 (s, 3H, O—CH$_3$); 4.1 (m, 1H, CH—OH); 4.4 (m, 3H, CH—OH+O—CH$_2$—CH$_3$); 5.2 (dd, 1H, 6-H); 6.75 (d, 1H, 7-H); 7.05 (t, 2H, 3''-H); 7.45 (m, 2H, 2''-H) ppm.

EXAMPLE 130

Methyl erythro-(E)-7-[2-(4-fluorophenyl)-4-isopropyl-5-methoxy-methyl-6-methyl-1-oxo-pyridin-3-yl]-3,5-dihydroxy-hept-6-enoate

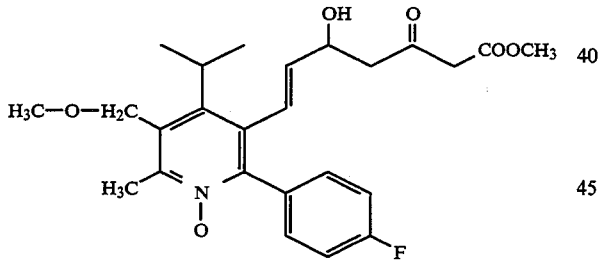

67 mg (0.15 mmol) of the compound from Example 116 and 54 mg (0.17 mmol) of 55% strength meta-chloroperbenzoic acid are stirred for 2 h at room temperature in 6 ml of dichloromethane. The solvent is stripped off, and the residue is taken up in 20 ml of ethyl acetate and washed with 20 ml of saturated sodium hydrogen carbonate solution. The aqueous phase is washed with 20 ml of ethyl acetate and the combined organic phases are dried over magnesium sulphate. The crude product is chromatographed on 10 g of silica gel (230–400 mesh) in a column (φ2 cm) using ethyl acetate and ethyl acetate/methanol (10:1).

Yield: 57 mg (82% of theory) of amorphous solid $^1$H-NMR (CDCl$_3$): δ=1.1-1.3 (m, 2H, CH(OH)—CH$_2$—CH(OH)); 1.35 (d, 6H, CH(CH$_3$)$_2$); 2.38 (m, 2H, CH$_2$—COOCH$_3$); 2.6 (s, 3H, 6'-CH$_3$); 3.4 (b, 1H, OH); 3.5 (m, 4H, CH(CH$_3$)$_2$+CH$_2$—O—CH$_3$); 3.28 (b, 1H, OH); 3.72 (s, 3H, COOCH$_3$); 4.05 (m, 1H, HO—C—H); 4.28 (m, 1H, HO—C—H); 4.55 (s, 2H, O—CH$_2$); 5.12 (dd, 1H, 6-H); 6.38 (d, 1H, 7-H); 7.05-7.25 (m, 4H, aromatic-H) ppm. MS: m/e=461 (9%), M$^+$.

EXAMPLE 131

2-(4-Fluorophenyl)-3-formyl-4,6-diisopropyl-5-methoxymethyl-pyridine

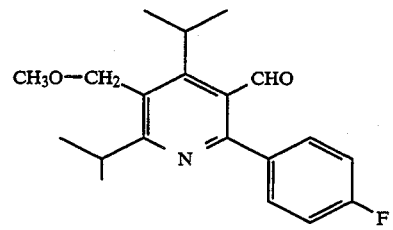

3.15 g (96% of theory) of colorless crystals of m.p. 77° C. (from MeOH) are obtained from 3.15 g (10 mmol) of the compound from Example 122 in analogy to the instructions from Example 59

EXAMPLE 132

Methyl erythro-(E)-7-[2-(4-fluorophenyl)-4,6-diisopropyl-5-methoxymethyl-pyridin-3-yl]-3,5-dihydroxy-hept-6-enoate

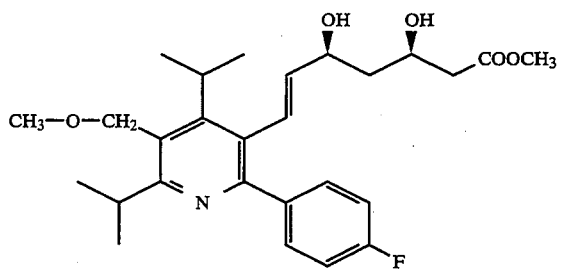

Colorless crystals of m.p. 92° C. (from ether/petroleum ether) are obtained from the compound from Example 131 according to the instructions from Example 8, 9 and 10

$^1$H-NMR (CDCl$_3$): δ=1.3 (m, 14H, CH(CH$_3$)$_2$+4-H); 2.4 (m, 2H, 2-H); 3.05 (b, 1H, OH); 3.3-3.57 (m, 5H, O—CH$_3$+CH(CH$_3$)$_2$); 3.62 (b, 1H, OH); 3.72 (s, 3H, COOCH$_3$); 4.1 (m, 1H CH—OH) 4.35 (m, 1H, CH—OH); 4.55 (s, 2H, O—CH$_2$); 5.15 (dd, 1H, 6-H); 6.75 (d, 1H, 7-H); 7.0 (t, 2H, 3''H); 7.45 (m, 2H, 2''-H).

EXAMPLE 133

5-Cyano-3-ethoxycarbonyl-2-(4-fluorophenyl)-1,4-dihydro-4-isopropyl-6-methyl-pyridine

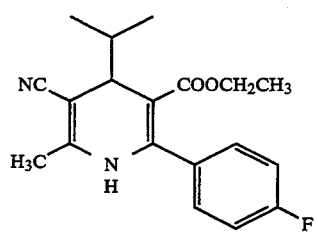

17.4 g (0.2 mol) of 3-amino-crotonacidnitrile and 56 g (0.2 mol) of the compound from Example 109 are heated to reflux overnight in 800 ml of ethanol. The solvent is stripped off and the residue is chromatographed on silica gel using petroleum ether/ethyl acetate 20:1.

Yield: 14.9 g (21% of theory) $^1$H-NMR (CDCl$_3$): δ=1.0 (m, 9H); 1.9 (m, 1H); 2.2 (m, 3H); 3.6 (d, 1H); 3.9 (m, 2H); 5.75 (b, 1H); 7.1 (t, 2H); 7.25 (m, 2H).

EXAMPLE 134

5-Cyano-3-ethoxycarbonyl-2-(4-fluorophenyl)-4-isopropyl-6-methyl-pyridine

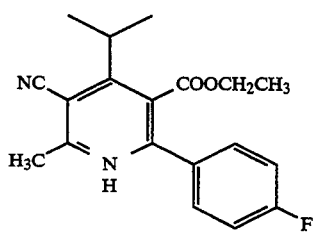

From 9.8 (30 mmol) of the compound from Example 133 analogously to Example 3

Yield: 9.4 g (96% of theory), m.p. 76° C.

EXAMPLE 135

5-Cyano-2-(4-fluorophenyl)-3-hydroxymethyl-4-isopropyl-6-methyl-pyridine

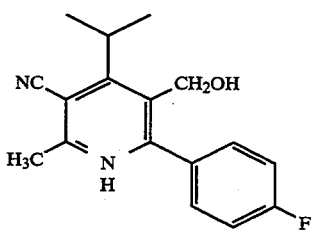

50 ml (60 mmol) of a 1.2M diisobutylaluminum hydride solution in toluene are added under argon during the course of 1.5 h to a solution of 9.8 g (30 mmol) of the compound from Example 134 in 150 ml of toluene p.a. at −75° C. and the mixture is stirred for a further 30 minutes.

280 ml of water are cautiously added dropwise at −30° C., and the mixture is filtered with suction using kieselguhr and washed with ethyl acetate. The aqueous phase is extracted three times using ethyl acetate and the contaminated organic phases are washed with saturated sodium chloride solution, dried over sodium sulphate and concentrated. Column chromatography (400 g of silica gel, 230–400 mesh, φ6 cm, petroleum ether/ethyl acetate 10/1 5/1) yields 3 zones:

1. 3-Ethoxycarbonyl-2-(4-fluorophenyl)-5-formyl-4-isopropyl-6-methyl-pyridine

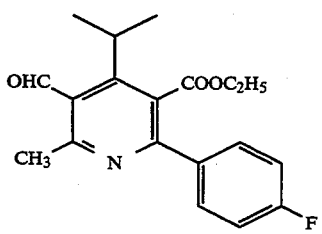

2.6 g (26% of theory) of m.p. 53° C.

2. 2.1 g (25% of theory) of the title compound (Example 135) m.p. 157° C. from ether/petroleum ether.

3. 2-(4-Fluorophenyl)-5-formyl-3-hydroxymethyl-4-isopropyl-6-methyl-pyridine

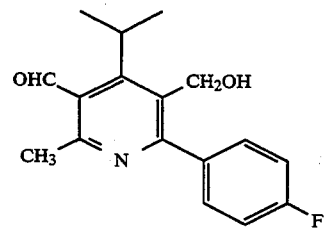

1.6 g (19% of theory), m.p. 150° C. from ether/petroleum ether.

EXAMPLE 136

5-Cyano-2-(4-fluorophenyl)-3-formyl-4-isopropyl-6-methylpyridine.

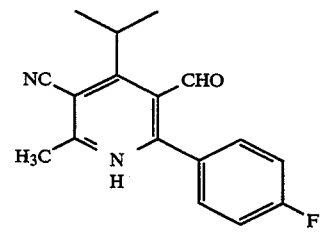

2.2 g (10.5 mmol) of trifluoroacetic anhydride in 10 ml of methylene chloride are added dropwise at −75° C. to 1.1 g (14 mmol) of DMSO in 8 ml of methylene chloride, the mixture is stirred for 10 minutes at −70° C., a solution of 2.0 g (7 mmol) of the compound from Example 135 in 50 ml of methylene chloride is then added dropwise and the mixture is stirred for 1 h at −70° C.

2.1 ml (21 mmol) of triethylamine are added dropwise to the suspension now present and the mixture is stirred for 10 minutes at −65° C. After warming to room temperature, it is washed with saturated sodium chloride solution, dried over sodium sulphate and concentrated.

Crude yield: 2.0 g (100% Of theory), m. p. 109° C. $^1$H-NMR (CDCl$_3$): δ=1.52 (d, 6H, CH(CH$_3$)$_2$); 2.9 (s,, 3H, 6-CH$_3$); 4.0 (sept. 1H, CH(CH$_3$)$_2$); 7.2 (m, 2H, 3'-H); 7.5 (m, 2H, 2'H); 9.95 (s, 1H, CHO).

EXAMPLE 137

(E)-3-[5-Cyano-2-(4-fluorophenyl)-4-isopropyl-6-methylpyrid-3-yl]-prop-2-enal

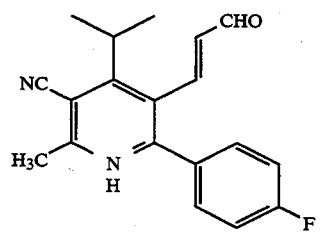

From 1.9 g of the compound from Example 136 analogously to Example 8

Yield: 0.6 g (28% of theory), m.p. 112° C. (ether-petroleum ether).

EXAMPLE 138

Methyl (E)-7-[5-cyano-2-(4-fluorophenyl)-4-isopropyl-6-methyl-pyrid-3-yl]-5-hydroxy-3-oxo-hept-6-enoate

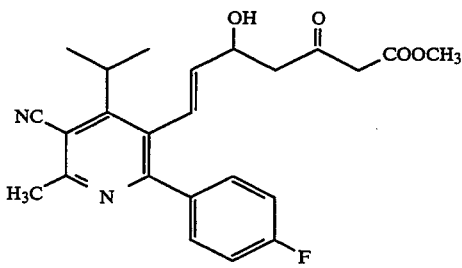

From 0.52 g (1.7 mmol) of the compound from Example 137 analogously to Example 9
Yield: 0.32 g (44% of theory) of yellowish oil.

EXAMPLE 139

Methyl erythro-(E)-7-[5-cyano-2-(4-fluorophenyl)-4-isopropyl-6-methyl-pyrid-3-yl]-3,5-dihydroxy-hept-6-enoate

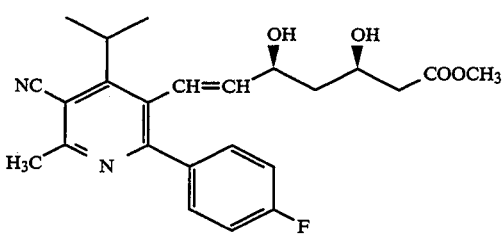

From 0.32 g of the compound from Example 138 analogously to Example 10
Yield: 0.15 g (47% of theory) of yellowish oil. $^1$H-NMR (CDCl$_3$): δ=1.35 (m, 2H, CH(OH)CH$_2$—CH(OH); 1.45 (d, 6H, CH(CH$_3$)$_2$); 2.42 (m, 2H, CH$_2$—COOCH$_3$); 2.7 (s, 3H, 6-CH$_3$); 3.55 (m, 2H, CH(CH$_3$)$_2$+OH); 3.68 (b, 1H, OH); 3.72 (s, 3H, O—CH$_3$); 4.13 (m, 1H, CH(OH)), 4.4 (m, 1H, CH(OH)); 5.32, (dd, 1H,, olefin-H); 6.6 (d, 1H, olefin-H); 7.08 (m, 2H, 3″-H); 7.45 (m, 2H, 2″-H).

EXAMPLE 140

Ethyl 4-fluorobenzoylacetate

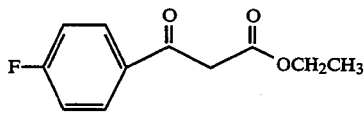

21.7 g (0.72 mol) of sodium hydride (80% strength, 20% mineral oil) are weighed into a liter of diethyl ether p.a. and 85.5 g (127 ml, 0.72 mol) of diethyl carbonate (VK 22-010) are subsequently added. A solution of 100 g (0.72 mol) of 4-fluoroacetophenone in 300 ml of diethyl ether are added dropwise to this solution at boiling heat over a period of 4 hours (vigorous, mechanical stirrer necessary; a viscous paste is formed). The mixture is then heated to reflux for a further hour, then cooled to about 5° C. and a solution of 50 ml of acetic acid and 100 ml of Et$_2$O is next added dropwise under N$_2$ at this temperature. About 500 ml of H$_2$O are subsequently added dropwise and the organic phase is separated off. The aqueous phase is extracted once again using Et$_2$O (2×400 ml), and the combined ethereal phases are washed with NaHCO$_3$ solution, dried over MgSO$_4$ and concentrated. The residue is distilled over a short Vigreux column.

Yield: 93 g (60%) b.p. 0.4 mm 99°–102° C.

EXAMPLE 141

5-Cyano-3-ethoxycarbonyl-4-(4-fluorophenyl)-1,4-dihydro-2-isopropyl-6-methyl-pyridine

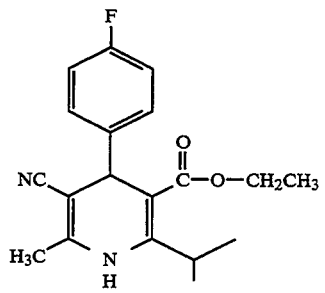

52.8 g (0.2 mol) of the compound from Example 1 and 16.4 g (0. 2 mol) of 3-amino-crotononitrile are heated to reflux for 2 h in 200 ml of ethylene glycol. After cooling, the deposited oil is taken off and extracted another three times using ether. The ether phases are washed with water, dried and concentrated. The residue and the initially isolated oil are crystallized from ether.

Yield: 31.4 g (48%), m.p. 168° C.

EXAMPLE 142

5-Cyano-3-ethoxycarbonyl-4-(4-fluorophenyl)-2-isopropyl-6-methyl-pyridine

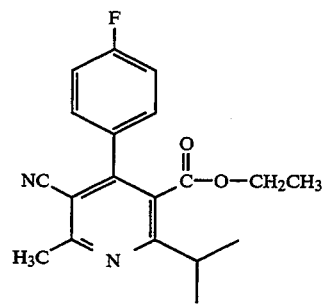

14.8 g (45 mmol) of the compound from Example 141 are reacted analogously to Example 3.

Yield: 13.7 g (93% of theory) of colorless crystals of m.p. 95° C.

EXAMPLE 143

5-Cyano-4-(4-fluorophenyl)-3-hydroxymethyl-2-isopropyl-6-methyl-pyridine

Compound 1

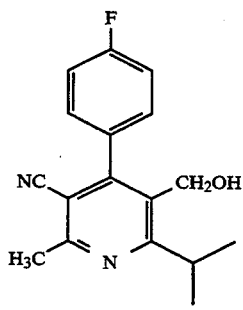

4-(4-Fluorophenyl)-5-hydroxyiminometnyl-3-hydroxymethyl-2-isopropyl-6-methyl-pyridine Compound 2

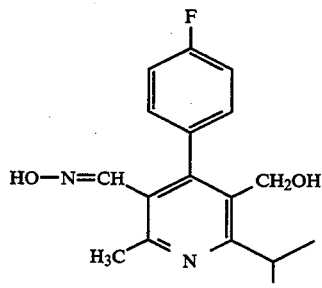

83.3 ml (0.1 mol) of 1.2M diisobutylaluminum hydride solution in toluene are added dropwise at −78° C. under argon during the course of 3 h to 16.3 g (50 mmol) of the compound from Example 142 in 240 ml of toluene p.A. so that the temperature remains under −75° C.

The mixture is stirred for a further 30minutes at −75° C. and allowed to warm to −30° C., and 300 ml of water and 160 ml of ethyl acetate are then added cautiously.

The mixture is filtered with suction over kieselguhr and washed with ethyl acetate. The aqueous phase is extracted three times using ethyl acetate, and the combined organic phases are washed with saturated sodium chloride solution, dried over sodium sulphate and concentrated. Column chromatography twice over silica gel using toluene/ethyl acetate 5:1 or petroleum ether/ethyl acetate 5:1 yields 3.4 g of a fraction of $R_f$ 0.2 (petroleum ether/ethyl acetate 5:1) which is a mixture of 5-cyano-4-(4-fluorophenyl)-3-hydroxymethyl-2-isopropyl-6-methylpyridine and 4-(4-fluorophenyl)-5-formyl-3-hydroxy-2-isopropyl-6-methyl-pyridine.

3.16 g of this mixture are dissolved in 10 ml of methanol and added to a solution of 1.22 g (17.6 mol) of hydroxylamine hydrochloride and 1.22 g (14.9 mmol) of sodium acetate in 10 ml of water. After stirring for 3 h at room temperature, the methanol is removed by rotary evaporation, some water is added and the mixture is extracted three times using ethyl acetate. The organic phases are washed with saturated sodium chloride solution, dried over sodium sulphate and concentrated. The residue is chromatographed in a column (100 g of silica gel 230–400 mesh, φ4 cm, petroleum ether/ethyl acetate 5:1). Two fractions are obtained:

Compound 1: 0.65 g (4.9%) of colorless crystals of m.p. 132° C. 5-Cyano-4-(4-fluorophenyl)-3-hydroxymethyl-2-isopropyl-6-methyl-pyridine $^1$H-NMR (CDCl$_3$): δ=1.32 (d, 6H,, CH(CH$_3$)$_2$); 1.6 (b, 1H, OH); 2.7 (s, 3H, 6-CH$_3$); 3.5 (sept, 1H, CH(CH$_3$)$_2$); 4.5 (d, 2H, CH$_2$—OH); 7.15–7.35 (m, 4H, aromatic-H).

Compound 2: 2.15 g (15.3%) of amorphous solid 4-(4-Fluorophenyl)-5-hydroxyiminomethyl-3-hydroxymethyl-2-isopropyl-6-methylpyridine $^1$H-NMR (CFCl$_3$): δ=1.33 (d, 6H, CH(CH$_3$)$_2$); 1.4 (b, 1H, —OH); 2.7 (s, 3H ,, 6-CH$_3$); 3.48 (m, 1H, CH(CH$_3$)$_2$); 4.4 (d, 2H, CH$_2$—OH); 7.15 (m, 4H, aromatic H); 7.77 (s, 1H, CH=N—); 8.08 (s, 1H, =N—OH).

EXAMPLE 144

5-Cyano-4-(4-fluorophenyl)-3-formyl-2-isopropyl-6-methylpyridine

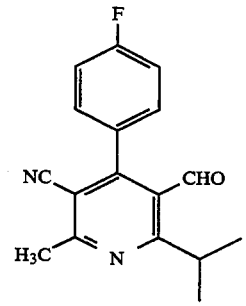

A) 0.63 g (2.2 mmol) of compound 1 from Example 144 is reacted analogously to the process from Example 136.

Yield: 0.6 g (97%).

B) 4.4 g (21 mmol) of trifluoroacetic anhydride in 15 ml of methylene chloride are added dropwise at −78° C. to 1.1 g (14 mmol) of DMSO in 8 ml of methylene chloride p.A. and the mixture is stirred for 10 minutes at −70° C. 2.1 g (7 mmol) of compound 2 from Example 143 are then added in 50 ml of methylene chloride, the mixture is stirred for 1 h at −70° C., 5.8 ml (42 mmol) of triethylamine are now added and the mixture is stirred for 4 h at room temperature. It is washed with saturated sodium chloride solution, concentrated, chromatographed over 100 g of silica gel (230–400 mesh, φ4 cm, petroleum ether/ethyl acetate 10:1) and recrystallized from ethyl acetate/petroleum ether.

Yield: 0.31 g (16%), m.p. 82° C. $^1$H-NMR (CDCl$_3$): δ=1.32 (d, 6H, CH(CH$_3$)$_2$); 2.78 (s, 3H, 6-CH$_3$); 3.77 (m, 1H, CH(CH$_3$)$_2$); 7.23 (m, 2H, 3'-H); 7.36 (m, 2H, 2'-H); 9.86 (s, 1H, CHO).

EXAMPLE 145

Methyl erythro-(E)-7-[5-cyano-4-(4-fluorophenyl)-2-isopropyl-6-methyl-pyrid-3-yl]-3,5-dihydroxy-hept-6-enoate

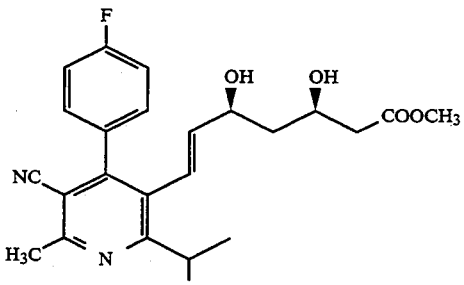

The reaction takes place from the compound from Example 144 in analogy to the reactions of Example 8, 9 and 10. colorless solid, m.p. 124° C.

$^1$H-NMR (CDCl$_3$): δ=1.3 (m, 8H, CH(CH$_3$)$_2$+CH(OH)—CH$_2$—CH(OH)); 2.4 (m, 2H, CH$_2$—COOCH$_3$); 2.75 (s, 3H, 6-CH$_3$); 3.35 (m, 2H, CH(CH$_3$)+OH); 3.6 (b, 1H, OH); 3.7 (s, 3H O—CH$_3$); 4.1 (m, 1H, CH—OH); 4.35 (m, 1H, CH—OH); 5.3 (dd, 1H, 6-H); 6.4 (d, 1H, 7-H); 7.05–7.3 (m, 4H, Ar-H).

EXAMPLE 146

Ethyl 5-(tert.-butyldimethylsilyloxymethyl)-6-cyclopropyl-4-(4-fluorophenyl)-2-isopropyl-pyridine-3-carboxylate

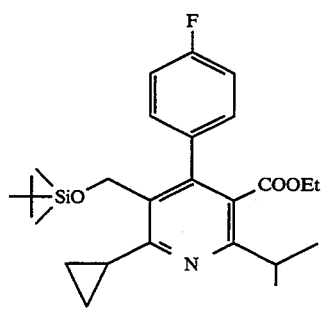

15 g (42 mmol) of the compound from Example 82 are reacted analogously to Example 5.
Yield: 16.9 g (85.4% of theory)

EXAMPLE 147

3-(tert.-Butyldimethylsilyloxymethyl)-2-cyclopropyl-4-(4-fluorophenyl)-5-hydroxymethyl-6-isopropyl-pyridine

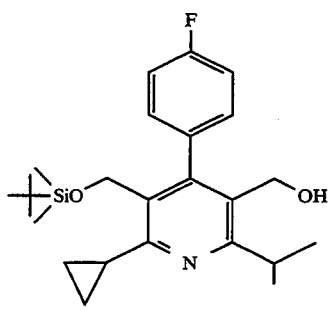

16.9 g (35.8 mmol) of the compound from Example 146 are reacted analogously to Example 6.
Yield: 12.3 g (80.1% of theory).

EXAMPLE 148

3-(tert.-Butyldimethylsilyloxymethyl)-2-cyclopropyl-4-(4-fluorophenyl)-6-isopropyl-5-methoxymethyl-pyridine

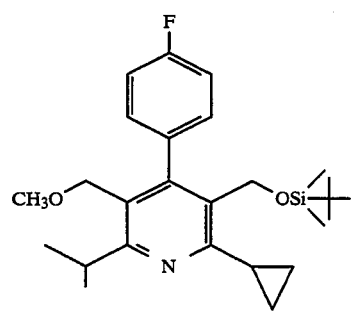

5.5 g (12.8 mmol) of the compound from Example 147 are reacted analogously to Example 59.
Yield: 5.7 g of crude product.

EXAMPLE 149

2-Cyclopropyl-4-(4-fluorophenyl)-3-hydroxymethyl-6-isopropyl-5-methoxymethyl-pyridine

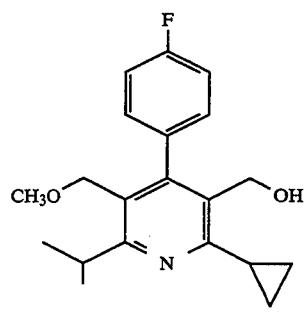

5.7 g (12.8 mmol) of the crude product from Example 148 are dissolved in absolute tetrahydrofuran. After addition of 12.8 ml of tetrabutylammonium fluoride solution (1M in THF) the mixture is stirred overnight at room temperature. 50 ml of saturated sodium hydrogen carbonate solution are then added and the mixture is extracted several times with methylene chloride. The combined organic phases are dried with sodium sulphate, concentrated and chromatographed over silica gel (eluent: petroleum ether/ethyl acetate 713).

Yield: 3.9 g (94% of theory). $^1$H-NMR (CDCl$_3$): δ=0.0 (s, 6H); 0.87 (s, 9H); 0.8–1.0 (m, 2H); 1.22 (d, 6H); 1.10–1.30 (m, 2H); 2.31 (m, 1H); 3.12 (s, 3H); 3.30 (m, 1H); 3.98 (s, 2H); 4.47 (m, 2H); 7.0–7.3 (m, 4H) ppm.

EXAMPLE 150

Methyl erythro-(E)-7-[2-cyclopropyl-4-(4-fluorophenyl)-6-isopropyl-5-methoxymethyl-pyrid-3-yl]-3,5-dihydroxy-hept-6-enoate

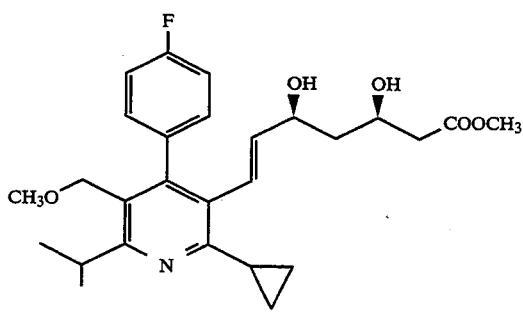

Example 150 was prepared from the compound from Example 149, in analogy to the reactions of Examples 7, 8, 9 and 10.

$^1$H-NMR (CDCl$_3$): δ=0.89 (m, 2H); 1.18 (m, 2H); 1.26 (d, 6H); 1.40 (m, 2H); 2.24 (m, 1H); 2.44 (m, 2H); 3.17 (s, 3H); 3.30 (m, 1H); 3.72 (s, 3H); 4.03 (s, 2H); 4.12 (m, 1H); 4.32 (m, 1H); 5.51 (d,d, 1H); 6.32 (d, 1H); 7.10 (m, 4H) ppm.

EXAMPLE 151

Ethyl 3-amino-3-cyclopropyl-acrylate

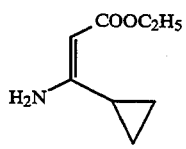

1.1 g of p-toluenesulphonic acid are added to 49.9 9 (0.32 mol) of ethyl cyclopropylcarbonylacetate in 200 ml of dry toluene and the mixture is saturated with ammonia gas at room temperature with stirring. After allowing to stand overnight, the mixture is heated under reflux for 8 h in a water separator, ammonia gas being continuously introduced. The mixture is allowed to cool overnight and is filtered, and the toluene solution is concentrated in vacuo and distilled from unreacted starting material in a high vacuum up to 65° C. The substance is subsequently found in the residue.

Yield: 11.9 g (24% of theory).

EXAMPLE 152

Diethyl 1,4-dihydro-2,6-dicyclopropyl-4-(4-fluorophenyl)pyridine-3,5-dicarboxylate

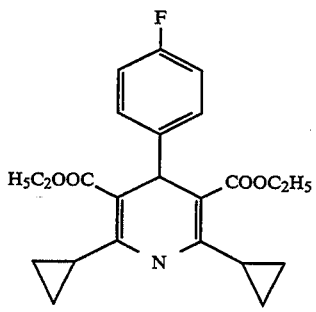

6.2 g (40 mmol) of the compound from Example 151 and 10.5 g (40 mmol) of the compound from Example 79 are dissolved in 100 ml of ethylene glycol and heated to reflux overnight. After cooling to room temperature, the mixture is extracted several times using ether, and the organic phase is washed once each with 10% strength hydrochloric acid, saturated sodium bicarbonate solution and water, dried over magnesium sulphate and concentrated in vacuo.

Yield: 10.4 g (65.1% of theory). $^1$H-NMR (CDCl$_3$): δ=0.60 (m, 4H); 0.95 (m, 4H); 1.23 (t, 6H); 2.72 (m, 2H); 4.12 (m, 4H); 5.02 (s, 1H); 5.40 (s, 1H); 6.88 (m, 2H); 7.20 (m, 2H) ppm.

EXAMPLE 153

Methyl erythro-(E)-7-[2,6-dicyclopropyl-4-(4-fluorophenyl)-5-methoxymethyl-pyrid-3-yl]-3,5-dihydroxy-hept-6-enoate

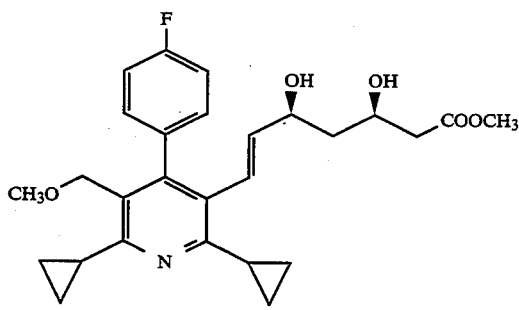

Example 153 was prepared from the compound from Example 152, in analogy to the reactions of Examples 3, 4, 59, 60, 7, 8, 9 and 10.

$^1$H-NMR (CDCl$_3$): δ=0.89 (m, 4H); 1.08 (m, 4H); 1.40 (m, 2H); 2.21 (m, 2H); 2.43 (m, 2H); 3.21 (s, 3H); 3.72 (s, 3H); 4.11 (m, 1H); 4.15 (s, 2H); 4.30 (m, 1H); 5.47 (dd, 1H); 6.30 (d, 1H); 7.10 (m, 4H) ppm.

EXAMPLE 154

Ethyl 2,6-diisopropyl-5-ethoxymethyl-4-(4-fluorophenyl)pyridine-3-carboxylate

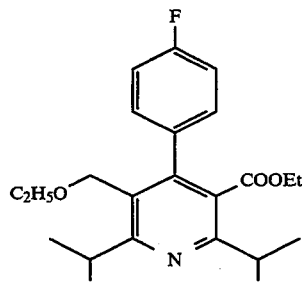

4.4 ml (76 mmol) of absolution ethanol are added dropwise at room temperature to a suspension of 2.29 g (76 mmol) of sodium hydride (80% strength) in 30 ml of absolute tetrahydrofuran and the mixture is stirred for 30 minutes. A solution of 2.7 g (7.6 mmol) of the compound from Example 86 are then added dropwise in 20 ml of absolute tetrahydrofuran and the mixture is heated overnight under reflux. The reaction batch is subsequently poured onto ice water and, after the pH has been adjusted to 8, extracted several times using ether. The organic phase is washed with sodium chloride solution, dried over sodium sulphate, concentrated and chromatographed over silica gel (eluent ethyl acetate/petroleum ether 5195).

Yield: 1.07g (36.4% of theory). $^1$H-NMR (CDCl$_3$): $\delta=0.95$ (t, 3H); 1.13 (t, 3H); 1.31 (m, 6H); 3.05 (m, 1H); 3.32 (q, 2H); 3.41 (m, 1H); 3.97 (q, 2H); 4.18 (d, 2H); 7.08 (m, 2H); 7.27 m, 2H) ppm.

EXAMPLE 155

Methyl erythro-(E)-7-[2,6-diisopropyl-5-ethoxymethyl-4-(4-fluorophenyl)-pyrid-3-yl]-3,5-dihydroxy-hept-6-enoate

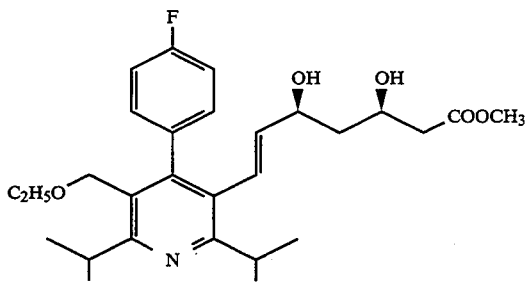

Example 155 was obtained from the compound from Example 154, in analogy to the reactions from Examples 60, 7, 8, 9 and 10.

$^1$H-NMR (CDCl$_3$): $\delta=1.13$ (t, 3H); 1.20–1.50 (m, 8H); 2.43 (m, 2H); 3.30 (m, 3H); 3.72 (s, 3H); 4.08 (m, 1H); 4.12 (s, 2H); 4.29 (m, 1H); 5.25 (dd, 1H); 6.30 (d, 1H); 7.0–7.2 (m, 4H) ppm.

The following compounds were obtained from Example 86 analogously to Example 155:

EXAMPLE 156

Methyl erythro-(E)-(7-[2,6-diisopropyl-4-(4-fluorophenyl)-5-propyloxymethyl-pyrid-3-yl]-3,5-dihydroxy-hept-6-enoate.

EXAMPLE 157

Methyl erythro-(E)-(7-[2,6-diisopropyl-4-(4-fluorophenyl)-5-isopropoxymethyl-pyrid-3-yl]-3,5-dihydroxy-hept-6-enoate.

EXAMPLE 158

Methyl erythro-(E)-(7-[2,6-diisopropyl-4-(4-fluorophenyl)-5-butyloxymethyl-pyrid-3-yl]-3,5-dihydroxy-hept-6-enoate.

EXAMPLE 159

Methyl erythro-(E)-(7-[2,6-diisopropyl-4-(4-fluorophenyl)-5-pentyloxymethyl-pyrid-3-yl]-3,5-dihydroxy-hept-6-enoate.

EXAMPLE 160

Methyl erythro-(E)-(7-[2,6-diisopropyl-4-(4-fluorophenyl)-5-hexyloxymethyl-pyrid-3-yl]-3,5-dihydroxy-hept-6-enoate.

EXAMPLE 161

Sodium erythro-(E)-7-[2,6-diisopropyl-5-ethoxymethyl-4-(4-fluorophenyl)-pyrid-3-yl]-3,5-dihydroxy-hept-6-enoate

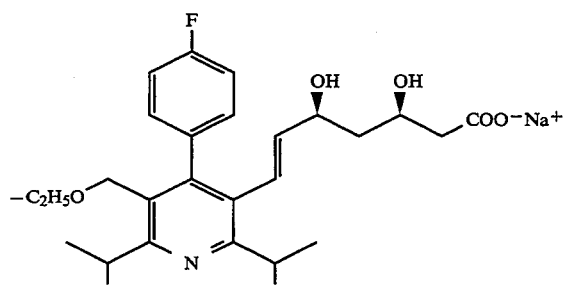

487 mg (1 mmol) of the compound from Example 155 are dissolved in 10 ml of tetrahydrofuran and 10 ml of 0.1N sodium hydroxide solution are added. After 1 h, the tetrahydrofuran is stripped off in vacuo and the aqueous residue is freeze-dried.

Yield: 490 mg (99% of theory).

EXAMPLE 162

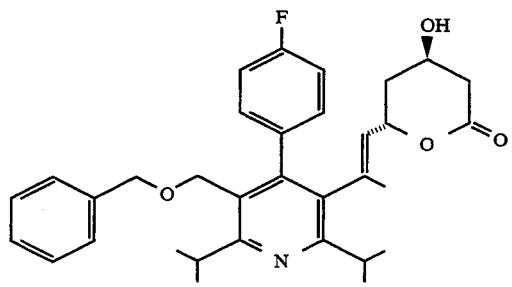

trans-(E)-6-[2-(3-benzyloxymethyl-2,6-diisopropyl-4-(4-fluorophenyl)-pyrid-5-yl)-ethenyl]-3,4,5,6-tetrahydro-4-hydroxy-2H-pyran-2-one 5.5 g (10 mmol) of the product from example 17 was dissolved in 100 ml tetrahydrofuran and after adding 100 ml 0.1N sodiumhydroxide solution was stirred for 1 hr at room temperature. Subsequently, the solution was diluted with 100 ml water, adjusted to pH 4.4 using 1N HCl and extracted with methylene chloride. The methylene chloride phase was dried with sodium sulphate and concentrated under vacuum. The residue was dissolved in 100 ml absolute toluene, 40 g molecular sieve 4 Å was added and heated under reflux over night. Subsequently it was separated from the molecular filter, concentrated under vacuum, and the residue crystallised with petroleum ether.

Yield: 4.3 (83.2% of the theoretical yield) $^1$H-NMR (CDCl$_3$): δ=1.22 (d,6H); 1.32 (d,6H); 1.40–1.80 (m,2H); 2.45–2.70 (m,2H); 3.30 (m,2H); 4.12 (m,1H); 4.14 (s,2H); 4.45 (s,2H); 5.04 (m,1H); 5.28 (dd,1H); 6.39 (d,1H); 6.95–7.40 (m,9H) ppm.

EXAMPLE 163

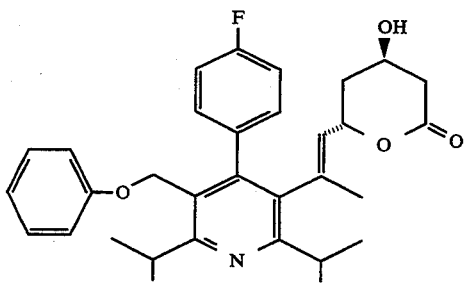

trans-(E)-6-[2-(2,6-diisopropyl-4-(4-fluorophenyl)-5-phenoxymethyl-pyrid-3-yl)-ethenyl]-3,4,5,6-tetrahydro-4-hydroxy-2H-pyran-2-one From 540 mg (1 mmol) of product 89 one receives 450 mg (89.4% of the theoretical yield) using a method analogous to example 162.

$^1$H-NMR (CDCl$_3$):=1.25 (d,6H); 1.30 (d,6H); 1.40–1.70 (m,2H); 2.60 (m,2H); 3.30 (m,2H); 4.18 (m,1H); 4.65 (s,2H); 5.08 (m,1H); 5.30 (dd,1H); 6.42 (d,1H); 6.70–7.30 (m,9H) ppm.

EXAMPLE 164

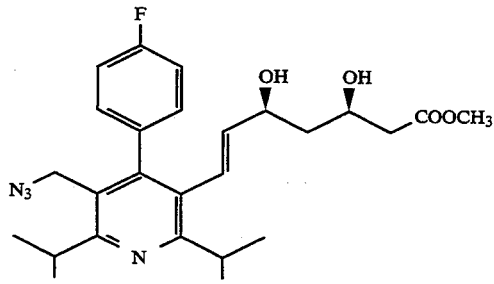

Methyl-erythro-(E)-7-[3-azidomethyl-2,6-diisopropyl-4-(4-fluorophenyl)-pyrid-5-yl)-3,5-dihydroxy-hept-6-enoate 459 mg (1 mmol) of the product from example 11 and 320 mg (1.1 mmol) triphenylphosphine were dissolved in 10 ml absol. tetrahydrofuran. After adding 3.2 ml of an 0.48 molar solution of HN$_3$ in toluene, it was cooled in an ice-bath and then 173 ml (1.1 mmol) diethyl azodicarboxylate was added. Subsequently the solution was stirred at room temperature overnight and then concentrated under vacuum. The residue was chromatographed over silica gel (mobile phase: ethyl acetate-petroleum ether 1:1)

Yield: 260 mg (53.7% of the theoretical yield) $^1$H-NMR (CDCl$_3$):=1.30 (d,6H); 1.39 (d,6H); 1.25–1.60 (m,2H); 2.50 (m,2H); 3.37 (m,2H); 3.80 (s,3H); 4.15 (s,1H); 4.18 (s,2H); 4.36 (m,1H); 5.36 (dd,1H); 6.36 (d,1H); 7.15 (m,4H) ppm.

EXAMPLE 165

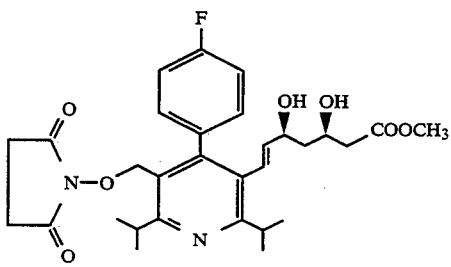

Methyl-erythro-(E)-7-[2,6-diisopropyl-4-(4-fluorophenyl)-5-succinimidooxymethyl-pyrid-3-yl)-3,5-dihydroxy-hept-6-enoate The preparation was carried out by a method analogous to example 164 using the product from example 11 and N-hydroxysuccinimide.

$^1$H-NMR (CDCl$_3$):?=1.28 (d,6H); 1.37 (d,6H); 1.2–1.5 (m,2H); 2.43 (m,2H); 2.66 (s,4H); 3.32 (sept.,1H); 3.72 (s,3H); 3.78 (sept.,1H); 4.08 (m,1H); 4.31 (m,1H); 4.86 (s,2H); 5.28 (dd,1H); 6.33 (d,1H); 7.0–7.4 (m,4H) ppm.

EXAMPLE 166

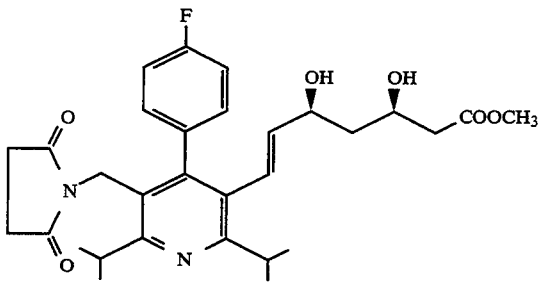

Methyl-erythro-(E)-7-[2,6-diisopropyl-4-(4-fluorophenyl)-5-succinimidomethyl-pyrid-3-yl)-3,5-dihydroxy-hept-6-enoate The preparation was carried by a method analogous to example 164 using the product from example 11 and succinimide.

$^1$H-NMR (CDCl$_3$):?=1.23 (m,12H); 1.25–1.50 (m,2H); 2.43 (m,2H); 2.51 (s,4H); 3.16 (m,1H); 3.28 (m,1H);3.73 (s,3H); 4.07 (m,1H); 4.26 (m,1H); 4.52 (s,2H); 5.25 (dd,1H); 6.20 (d,1H); 7.0–7.2 (m,4H) ppm.

EXAMPLE 167

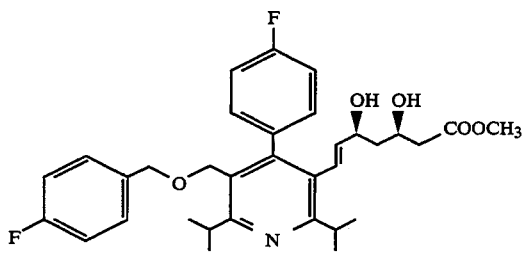

Methyl-erythro-(E)-7-[2,6-diisopropyl-3-(4-fluorobenzyloxymethyl)-4-(4-fluorophenyl)-pyrid-5-yl)-3,5-dihydroxy-hept-6-enoate.

Example 166 was prepared from the product of example 4 and 4-fluorobenzylbromide according to methods analogous to examples 12–17.

$^1$H-NMR (CDCl$_3$):=1.25 (m,6H); 1.32 (d,6H); 1.21–1.5 (m,2H); 2.42 (m,2H); 3.30 (m,2H); 3.72 (s,3H); 4.07 (m,1H); 4.13 (s,2H); 4.28 (m,1H); 4.30 (s,2H); 5.22 (dd,1H); 6.30 (d,1H); 6.90–7.30 (m,8H) ppm.

EXAMPLE 168

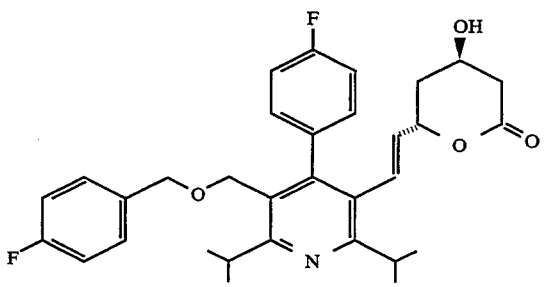

trans-(E)-6-[2-(2,6-diisopropyl-3-(4-fluorobenzyloxymethyl)-4-(4-fluorophenyl)-pyrid-5-yl)ethenyl]-3,4,5,-6-tetrahydro-4-hydroxy-2H-pyran-2--one.

The preparation was carried out by a method analogous to example using the product from example 167.

$^1$H-NMR (CDCl$_3$):=1.23 (d,6H); 1.32 (d,6H); 1.40–1.80 (m,2H); 2.40 (m,2H); 3.30 (m,2H); 4.13 (s,2H); 4.16 (m,1H); 4.30 (s,2H); 5.05 (m,1H); 5.28 (dd,1H); 6.37 (d,1H); 6.9–7.3 (m,8H) ppm.

EXAMPLE 169

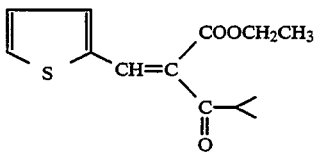

(E/Z)-2-Ethoxycarbonyl-4-methyl-1-(thiophen-2-yl)penten-3-one.

The above mentioned product was produced from ethyl isobutyryl acetate and thiophene-2-carbaldehyde by a method analogous to that for example 1.

Yuild: 86% yellow oil, b p 145° C. (1.5 mbar).

EXAMPLE 170

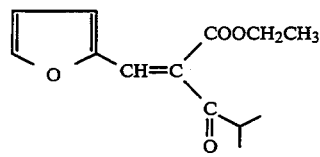

(E/Z)-2-Ethoxycarbonyl-1-(furan-2-yl)-4-methyl-pentene-3-one.

Analogue procedure for example 1 the above mentioned compound is produced from furan-2-carbaldehyde and ethyl isobutyryl acetate.

Yield: 93% yellow oil, bp: 130° C. (0.5 mbar).

EXAMPLE 171

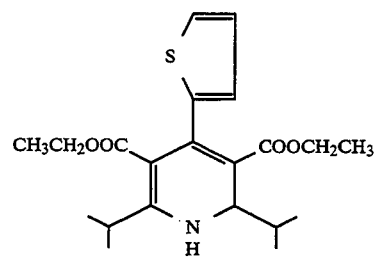

Ethyl-2,6-diisopropyl-4-(thiopen-2-yl)-1,4-dihydropyridine-3,5-bis-dicarboxylate.

10 g (0.28 mol) of the product from example 169 and 44 g (0.28 mol) ethyl-3-amino-4-methyl-pent-2-enoate were heated at 160° C. for 24 hrs. There after it was taken up in ethyl acetate, washed three times with 6N hydrochloric acid, twice with water and saturated sodium hydrogen carbonate solution, and the organic phase was dried over sodium sulphate, concentrated under vacuum, and the residue chromatographed on 400 g silica gel using petroleum ether-dichloromethane (2:1).

Yield: 50 g (46%) colourless crystals having a melting point of 72° C. (from N hexane).

EXAMPLE 172

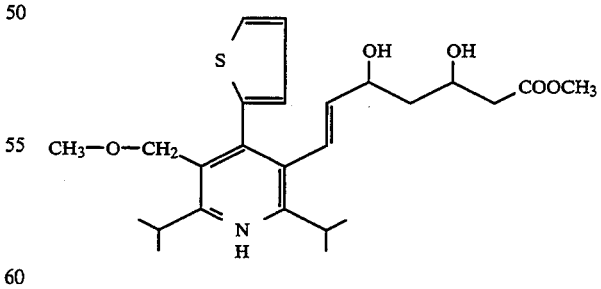

Methyl-erythro-(E)-7-[2,6-diisopropyl-5-methoxymethyl-4(thiophen-2-yl)-pyridin-3-yl]-3,5-dihydroxy-hept-6-enoate.

The above mentioned product was prepared by methods analogous to examples 3, 4, 59, 6, 7, 8, 9 and 10, based on the products from example 171.

Colourless crystals, melting point: 94° C.

EXAMPLE 173

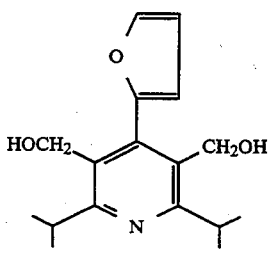

4-(Furan-2-yl)-3,5-bis(hydroxyethyl)-2,6-diisopropyl-pyridine

Based on the compound from example 170 and ethyl-3-amino-4-methyl-pent-2-enoate. The above mentioned product was prepared by methods analogous to the procedures for examples 171, 3 and 122.

Colourless crystals, melting point: 212° C.

EXAMPLE 174

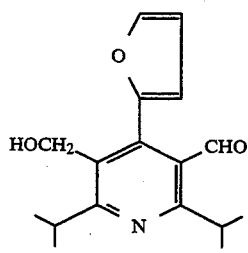

3-formyl-4-(furan-2-yl)-5-hydroxymethyl-2,6-diisopropyl-pyridine

The synthesis was carried out by the method analogous to example 7 using 32 g (0.11 mol) of the product from 173 and 28.6 g (0.13 mol) pyridium chlorochromate.

Yield: 14.6 g (46% colourless crystals, melting point: 113° C.).

EXAMPLE 175

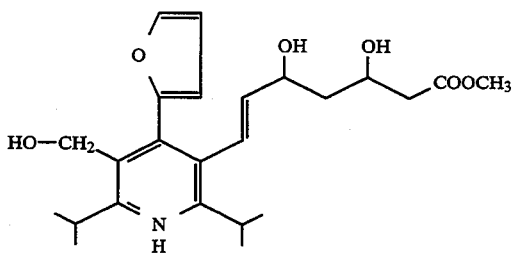

Methyl-erythro-(E)-7-[4-(furan-2-yl)-5-hydroxymethyl-2,6-diisopropyl-pyridin-3-yl]-3,5-dihydroxy-hept-6-enoate.

The a/m product was prepared by a method analogous to the procedures for examples 123, 124 and 125 on the basis of example 174.

Colourless crystals, melting point: 86%

EXAMPLE 176

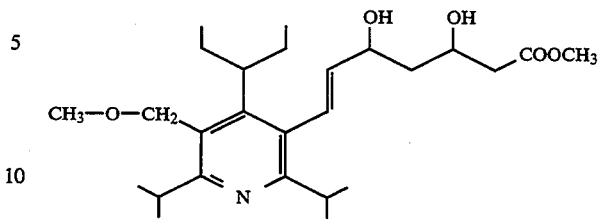

Methyl-erythro-(E)-7-[2,4,6,triisopropyl-5-methoxymethyl-pyridin-3-yl ]-3,5-dihydroxy-hept-6-enoate.

The a/m product was synthesised by a method analogous to the procedures from examples 171, 3, 4, 59, 6, 7, 8, 9 and 10. Using the product from 119 and ethyl-3-amino-4-methyl-pent-2-enoate.

Colourless oil $^1$H-NMR (CDCl$_3$):?=1.1–1.35.(m,18H, isopropyl-H) 1.65–1.85 (m,2H, 4-H) 2.55 (d,2H,2-H), 3.2–3.45 (m,7H, isopropyl-H, OH, CH$_3$—O—CH$_2$) 3,7 (m,4H, OH, COOCH$_3$) 4.35 (m,1H, HO—CH) 4.45 (s,2H,CH$_3$—O—CH$_2$) 4.62 (m, 1H, HO—CH) 5.55 (dd, 1H,6-H) 6.73 (d, 1H, 7-H).

EXAMPLE 177

Methyl-erythro-(E)-7-[2,6-diisopropyl-5-methoxymethyl-4-phenyl-pyrid-3-yl]-3,5-dihydroxy-hept-6-enoate

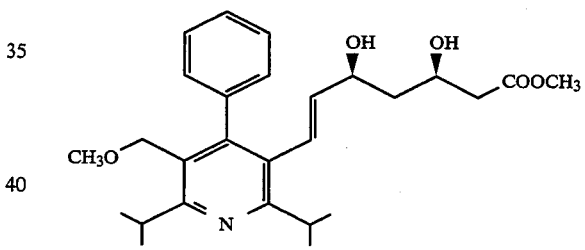

$^1$H-NMR (CDCH$_3$): δ=1.15–1.40 (m, 14H); 2.47 (m, 2H); 3.15 (s, 3H); 3.35 (m, 2H); 3.72 (s, 3H); 4.03 (m, 1H); 4.08 (s, 2H); 4.24 (m, 1H); 5.22 (dd, 1H); 6.31 (d, 1H); 7.12 (m, 2H); 7.33 (m, 3H).

EXAMPLE 178

Methyl-erythro-(E)-7-[2,6-diisopropyl-4-(4-fluoro-3-phenoxyphenyl)-5-methyoxymethyl-pyrid-3-yl]-3,5-dihydroxy-hept-6-enoate

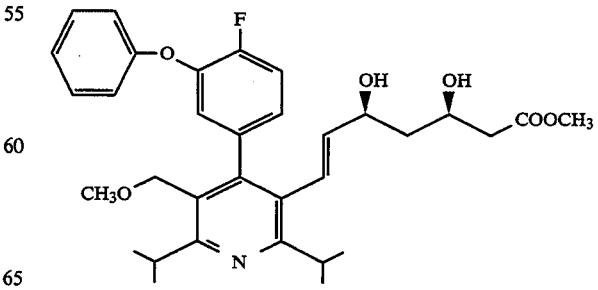

$^1$H-NMR (CDCH$_3$): δ=1.1–1.6 (m, 14H); 2.44 (m, 2H); 3.18 (s, 3H); 3.30 (m, 2H); 3.72 (s, 3H); 4.08 (s, 2H);

4.15 (m, 1H); 4.35 (m, 1H); 5.28 (dd, 1H).; 6.32 (d, 1H); 6.9–7.4 (m, 8H).

EXAMPLE 179

Methyl-erythro-(E)-7-[2,6-diisopropyl-4-(4-fluoro-3-methylphenyl)-5-methoxymethyl-pyrid-3-yl]-3,5-dihydroxy-hept-6-enoate

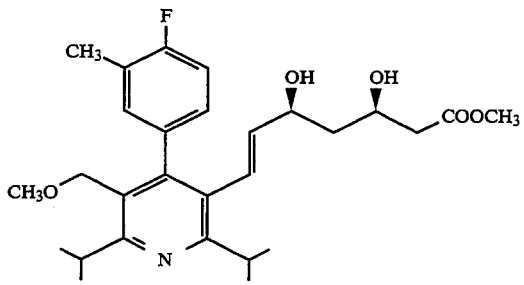

¹H-NMR (CDCH₃): δ=1.1–1.5 (m, 14H); 2.38 (bs, 3H); 2.43 (m, 2H); 3.20 (s, 3H); 3.32 (m, 2H); 3.73 (s, 3H); 4.07 (s, 2H); 4.09 (m, 1H); 4.30 (m, 1H); 5.28 (ddd, 1H); 6.30 (dd, 1H); 6.9–7.1 (m, 3H).

EXAMPLE 180

Methyl-erythro-(E)-7-[2,6-diisopropyl-5-methoxymethyl-4-(4-methylphenyl)-pyrid-3-yl]-3,5-dihydroxy-hept-6-enoate

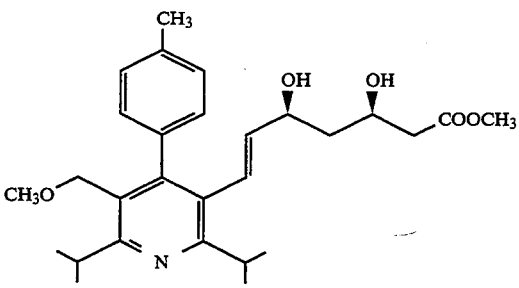

¹H-NMR (CDCH₃): δ=1.1–1.5 (m, 14H); 2.38 (s, 3H); 2.42 (m, 2H); 3.19 (s, 3H); 3.30 (m, 2H); 3.72 (s, 3H); 4.07 (m, 1H); 4.11 (s, 2H); 4.27 (m, 1H); 5.28 (ddd, 1H); 6.31 (d, 1H); 7.03 (m, 2H); 7.16 (m, 2H).

EXAMPLE 181

Methyl-erythro-(E)-7-[2,6-diisopropyl-5-methoxymethyl-4-(4-methoxyphenyl)-pyrid-3-yl]-3,5-dihydroxy-hept-6-enoate

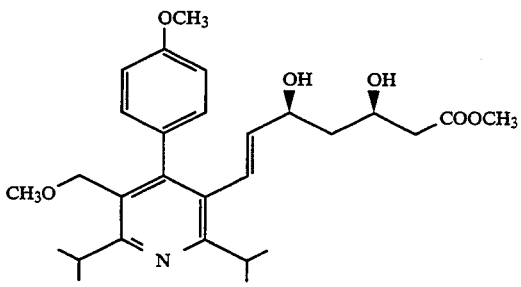

¹H-NMR (CDCH₃): δ=1.1–1.5 (m, 14H); 2.42 (m, 2H); 3.21 (s, 3H); 3.33 (m, 2H); 3.72 (s, 3H); 3.87 (s, 3H); 4.07 (m, 1H); 4.10 (s, 2H); 4.29 (m, 1H); 5.28 (dd, 1H); 6.31 (d, 1H); 6.9 (m, 2H); 7.07 (m, 2H).

EXAMPLE 182

Methyl-erythro-(E)-7-[6-cyclopentyl-4-(4-fluorophenyl)-2-isopropyl-5-methoxymethyl-pyrid-3-yl]-3,5-dihydroxy-hept-6-enoate

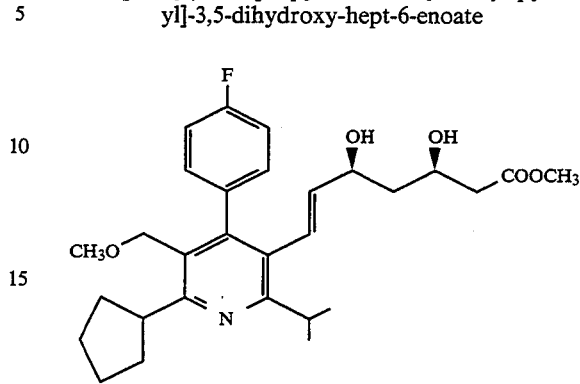

¹H-NMR (CDCH₃): δ=1.1–1.5 (m, 10H); 1.70 (m, 2H); 1.97 (m, 4H); 2.42 (m, 2H); 3.19 (s, 3H); 3.28 (sept., 1H); 3.47 (m, 1H); 3.72 (s, 3H); 4.06 (m, 1H); 4.08 (s, 1H); 4.28 (m, 1H); 5.23 (dd, 1H); 6.30 (d, 1H); 7.0–7.2 (m, 4H).

EXAMPLE 183

Methyl-erythro-(E)-7-[4-(4-fluorophenyl)-2-isopropyl-5-methoxymethyl-6-(2-thienyl)-pyrid-3-yl]-3,5-dihydroxy-hept-6-enoate

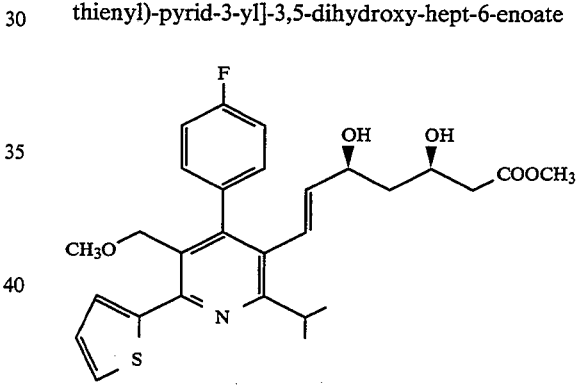

¹H-NMR (CDCH₃): δ=1.1–1.5 (m, 8H); 2.43 (m, 2H); 3.21 (s, 3H); 3.34 (sept., 1H); 3.73 (s, 3H); 4.05 (s, 2H); 4.08 (m, 1H); 4.31 (m, 1H); 6.39 (d, 1H); 7.0–7.3 (m, 5H); 7.42 (dd, 1H); 7.61 (dd, 1H).

EXAMPLE 184

Methyl-erythro-(E)-7-[4-(4-fluorophenyl)-2-isopropyl-5-methoxymethyl-6-(2-thienyl)-pyrid-3-yl]-3,5-dihydroxy-hept-6-enoate

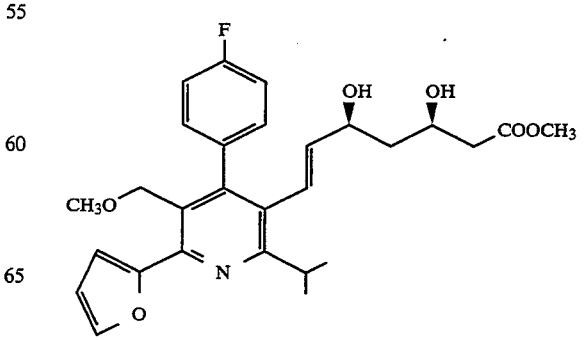

H-NMR (CDCH₃): δ=1.1–1.5 (m, 8H); 2.43 (m, 2H); 3.22 (s, 3H); 3.37 (sept., 1H); 3.73 (s, 3H); 4.09 (m, 1H); 4.20 (s, 2H); 4.32 (m, 1H); 5.28 (dd, 1H); 6.39 (d, 1H); 6.53 (dd, 1H); 7.0–7.2 (m, 5H); 7.62 (dd, 1H).

EXAMPLE 185

Methyl-erythro-(E)-7-[4-(4-fluorophenyl)-2-isopropyl-5-methoxymethyl-6-(2-thienyl)-pyrid-3-yl]-3,5-dihydroxy-hept-6-enoate

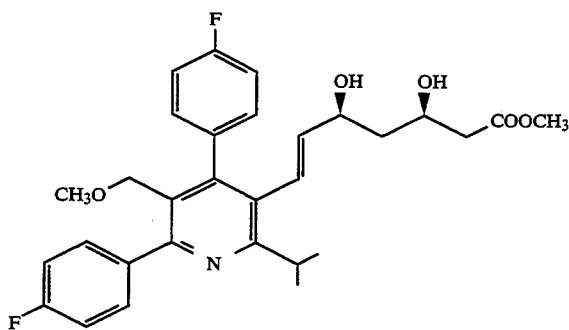

¹H-NMR (CDCH₃): δ=1.1–1.5 (m, 8H); 2.43 (m, 2H); 3.10 (s, 3H); 3.38 (sept., 1H); 3.72 (s, 3H); (s, 3H); 3.86 (s, 2H); 4.08 (m, 1H); 4.32 (m, 1H); 5.32 (dd, 1H); 6.43 (d, 1H); 7.0–7.3 (m, 6H); 7.82 (m, 2H).

EXAMPLE 186

Methyl-erythro-(E)-7-[4-(4-fluorophenyl)-2-isopropyl-5-methoxymethyl-6-(4-methoxyphenyl)-pyrid-3-yl]-3,5-dihydroxy-hept-6-enoate

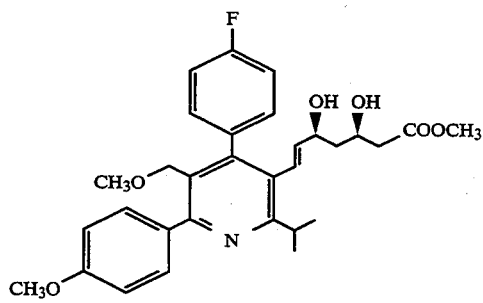

¹H-NMR (CDCH₃): δ=1.1–1.5 (m, 8H); 2.43 (m, 2H); 3.12 (s, 3H); 3.37 (sept., 1H); 3.73 (s, 3H); 3.87 (s, 5H); 4.10 (m, 1H); 4.31 (m, 1H); 5.29 (dd, 1H); 6.45 (d, 1H); 6.9–7.3 (m, 6H); 7.81 (m, 2H).

EXAMPLE 187

Methyl-erythro-(E)-7-[4-(4-fluorophenyl)-2-isopropyl-5-methoxymethyl-6-(1-methyl-2-phenylethyl)-pyrid-3-yl]-3,5-dihydroxy-hept-6-enoate

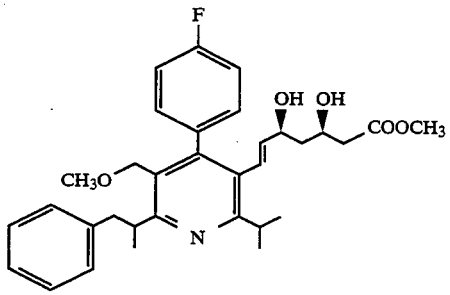

¹H-NMR (CDCH₃): δ=1.1–1.5 (m, 11H); 2.43 (m, 2H); 2.89 (m, 2H); 3.11 (s, 3H); 3.1–3.4 (m, 2H); 3.72 (s, 3H); 3.87 (s, 2H); 4.07 (m, 1H); 4.28 (m, 1H); 5.13 (dd, 1H); 6.31 (d, 1H); 6.9–7.3 (m, 9H).

EXAMPLE 188

Methyl-erythro-(E)-7-[4-(4-fluorophenyl)-2-isopropyl-6-(1-methoxyethyl-5-methoxymethyl-pyrid-3-yl]-3,5-dihydroxy-hept-6-enoate

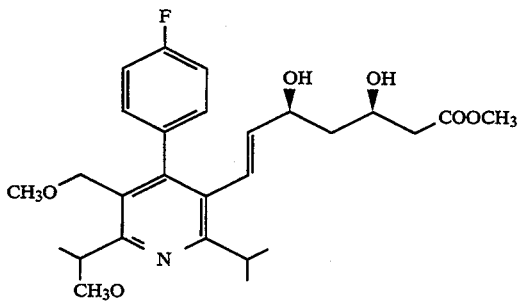

¹H-NMR (CDCH₃): δ==1.1–1.5 (m, 8H); 1.58 (d, 3H); 2.43 (m, 2H); 3.18 (s, 3H); 3.32 (s, 3H); 3.33 (sept., 1H); 3.72 (s, 3H); 4.08 (m, 1H); 4.09 (d, 1H); 4.20 (d, 1H); 4.30 (m, 1H); 4.82 (q, 1H); 5.28 (dd, 1H); 6.32 (d, 1H); 7.0–7.2 (m, 4H).

EXAMPLE 189

Methyl-erythro-(E)-7-[2,6-diisopropyl-4-(4-fluorophenyl)-5-(3methoxypropyl)-pyrid-3-yl]-3,5-dihydroxy-hept-6-enoate

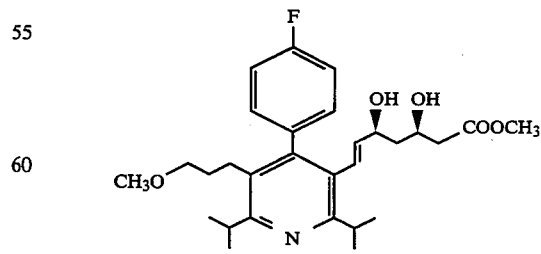

¹H-NMR (CDCH₃): δ=1.1–1.5 (m, 14H); 1.55 (m, 2H); 2.3–2.5 (m, 4H); 3.1–3.3 (m, 7H); 3.72 (s, 3H); 4.05 (m, 1H); 4.27 (m, 1H); 5.25 (dd, 1H); 6.22 (d, 1H); 6.9–7.2 (m, 1H).

EXAMPLE 190

Methyl-erythro-(E)-7-[2,6-diisopropyl-4-(4-fluorophenyl)-5-(1methoxyethyl)-pyrid-3-yl]-3,5-dihydroxy-hept-6-enoate

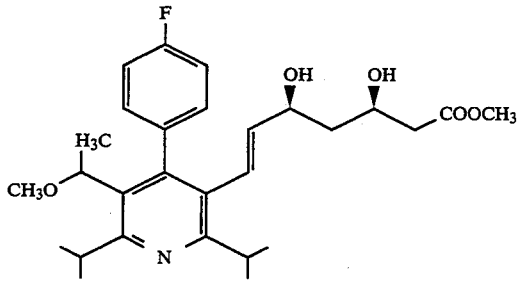

$^1$H-NMR (CDCH$_3$): δ=1.1-1.5 (m, 17H); 2.43 (mr 2H); 3.10 (d, 3H); 3.28 (sept., 1H); 3.72 (s, 3H; 3.77 (m, 1H); 4.07 (m, 1H); 4.18 (q, 1H); 4.28 (m, 1H); 5.29 (dd, 1H); 6.19 (d, 1H); 6.9–7.2 (m, 4H).

EXAMPLE 191

Methyl-erythro-(E)-7-[2,6-diisopropyl-4-(4-fluorophenyl)-5-(2,3-dimethoxypropoxymethyl)-pyrid-3-yl]-3,5-dihydroxy-hept-6-enoate

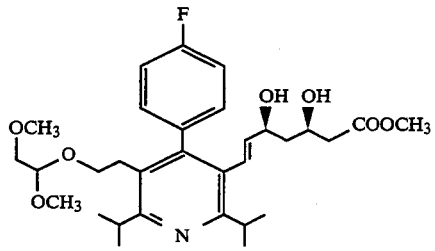

$^1$H-NMR (CDCH$_3$): δ=1.1-1.5 (m, 14H); 2.35 (m, 2H); 3.1-3.4 (m, 7H); 3.29 (s, 3H); 3.34 (s, 3H; 3.65 (s, 3H); 4.01 (m, 1H); 4.07 (bs, 2H); 4.21 (m, 1H); 5.17 (dd, 1H); 6.23 (d, 1H); 6.9–7.2 (m, 4H).

EXAMPLE 192

Methyl-erythro-(E)-7-[2,6-diisopropyl-5-ethyl-4-(4-fluorophenyl)pyrid-3-yl]-3,5-dihydroxy-hept-6-enoate

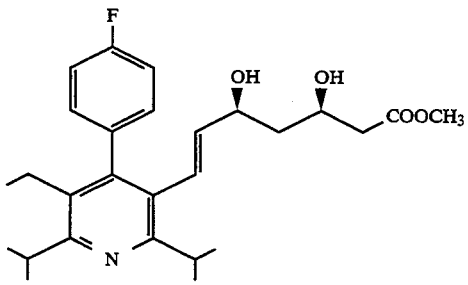

$^1$H-NMR (CDCH$_3$): δ=0.92 (t, 3H); 1.1-1.5 (m, 14H); 2.38 (q, 2H); 2.43 (m, 2H); 3.26 (m, 2H); 3.73 (s, 3H); 4.08 (m, 1H); 4.27 (m, 1H); 5.27 (dd, 1H); 6.22 (d, 1H); 6.0–7.2 (m, 4H).

EXAMPLE 193

Methyl-erythro-(E)-7-[2,6-diisopropyl-5-fluoromethyl-4-(4-fluorophenyl)-pyrid-3-yl]-3,5-dihydroxy-hept-6-enoate

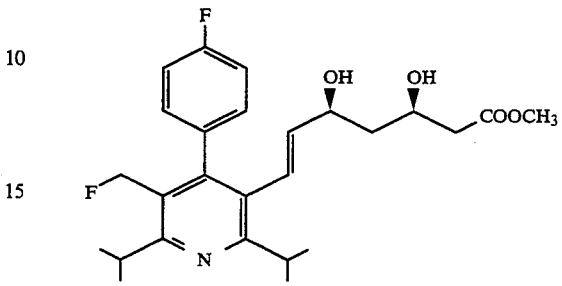

$^1$H-NMR (CDCH$_3$): δ=1.1-1.5 (m, 14H); 2.43 (m, 2H); 3.32 (sept., 1H); 3.42 (m, 1H); 3.72 (s, 3H); 4.08 (m, 1H); 4.32 (m, 1H); 5.14 (d, 2H); 5.28 (dd, 1H); 6.32 (d, 1H); 7.0–7.2 (m, 4H).

USE EXAMPLE

EXAMPLE 194

The determination of enzyme activity was carried out as modified by G. C. Ness et al., Archives of Biochemistry and Biophysics 197, 493–499 (1979). Male Rico rats (body weight 300–400 g) were treated for 11 days with Altromin powdered feed, to which 40 g of colestyramine/kg of feed was added. After decapitation, the liver was removed from the animals and placed on ice. The livers were comminuted and homogenized 3 times in a Potter-Elvejem homogenizer in 3 volumes of 0.1M saccharose, 0.05M KCl, 0.04M K$_x$H$_y$ phosphate, 03M ethylenediaminetetraacetic acid, 0.002M dithiothreitol (SPE) buffer pH 7.2. The mixture was subsequently centrifuged for 15 minutes at 15,000* g and the sediment rejected. The supernatant was sedimented for 75 minutes at 100,000 g. The pellet is taken up in ¼ volume of SPE buffer, homogenized once again and subsequently centrifuged again for 60 minutes at 100,000 g. The pellet is taken up using the 5-fold amount of its volume of SPE buffer, homogenized and frozen and stored at −78° C. (=enzyme solution).

For testing, the test compounds (or mevinolin as a reference substance) were dissolved in dimethylformamide with the addition of 5% by volume of 1N NaOH and employed in the enzyme test in various concentrations using 10 μl. The test was started after preincubation Of the compound with the enzyme at 37° C. for 20 minutes. The test batch was 0.380 ml and contained 4 μmol of glucose-6-phosphate, 1.1 mg of bovine serum albumin, 2.1 μmol of dithiothreitol, 0.35 μmol of NADP, 1 unit of glucose-6-phosphate dehydrogenase 35 μmol of KxHy phosphate PH 7.2, 20 μl of enzyme preparation and 56 nmol of 3× hydroxy-3-methyl-glutaryl conenzyme A (glutaryl-3-$^{14}$C) 100,000 dpm.

After incubation for 60 minutes at 37° C., the batch was centrifuged and 600 μl of the supernatant was applied to a 0.7×4 cm column filled with a 5-chloride 100–200 mesh (anion exchanger). It was washed with 2 ml of distilled water and 3 ml of aquasol were added to the runnings plus washing water and counted in the LKB scintillation counter. IC$_{50}$ values were determined by intrapolation by plotting the percentage inhibition against the concentration of the compound in the test. To determine the relative inhibitory potency, the IC$_{50}$ value of the reference substance mevinolin was set at 1 and compared with the simultaneously determined IC$_{50}$ value of the test compound.

According to use example 194; IC$_{50}$ value of the mevinolin was set at 1.

The results obtained were as follows:

| Example No. | Rel. Activity Mevinolin = 1) |
|---|---|
| 17 | 20 |
| 70 | 30 |
| 72 | 17 |
| 85 | 20 |
| 89 | 10 |
| 99 | 20 |
| 100 | 30 |
| 105 | 4 |
| 107 | 3 |
| 139 | 20 |

2ND USE EXAMPLE

EXAMPLE 195

The subchronic action of the compounds according to the invention on the blood cholesterol values of dogs was tested in feeding experiments of several weeks duration. For this, the substance to be investigated was given p.o. once daily in a capsule to healthy beagle dogs together with the feed over a period of time lasting several weeks. Colestyramine (4 g/100 g of feed) as the galic acid sequestrant was additionally admixed in the feed during the entire experimental period, i.e. before, during and after the administration period of the substances to be investigated. Venous blood was taken from the dogs twice weekly and the serum cholesterol was determined enzymatically using a commercial test kit. The serum cholesterol values during the administration period were compared with the serum cholesterol values before the administration period (controls).

Thus, for example, a lowering of the serum cholesterol by about 66% resulted for the compound according to the invention Example No. 17 after administration of 8 mg/kg p.o. daily for 2 weeks.

It will be appreciated that the instant specification and claims are set forth by way of illustration and not limitation, and that various modifications and changes may be made without departing from the spirit and scope of the present invention.

What is claimed is:

1. A substituted pyridine of the formula:

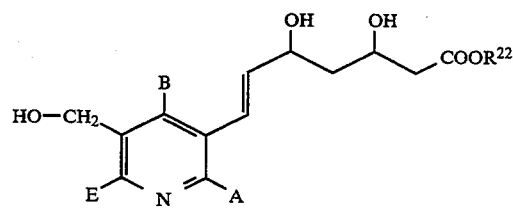

wherein

A represents phenyl or phenyl which is monosubstituted or disubstituted by a substituent selected from the group consisting of methyl, hydroxymethyl, ethyl, propyl, isopropyl, butyl, isobutyl, tert.-butyl, methoxy, ethoxy, propoxy, isopropoxy, phenoxy, benzyloxy, fluorine, chlorine or trifluoromethyl;

B represents cyclopropyl, methyl, ethyl, propyl, isopropyl, butyl, isobutyl, or tert.-butyl;

E represents methyl, ethyl, propyl, isopropyl, butyl, isobutyl, tert.-butyl, pentyl, isopentyl, hexyl or isohexyl; and R$^{22}$ represents hydrogen, lower alkyl, phenyl, benzyl or a physiologically tolerable metal or ammonium cation.

2. A compound according to claim 1, wherein such compound is erythro-(E)-7-[2-(4-fluorophenyl)-5-hydroxymethyl-4-isopropyl-6-methyl-pyrid-3-yl]-3,5-dihydroxy-hept-6-enoate of the formula:

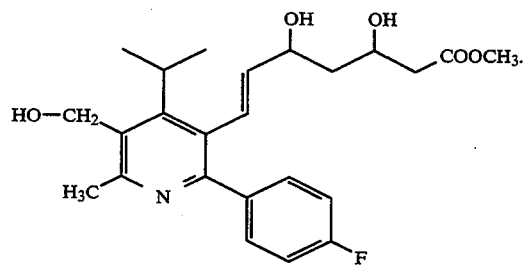

3. A compound according to claim 1, wherein such compound is erythro-(E)-7-[2-(4-fluorophenyl)-5-hydroxymethyl-4,6-diisopropyl-pyridin-3-yl]-3,5-dihydroxy-hept-6-enoate of the formula:

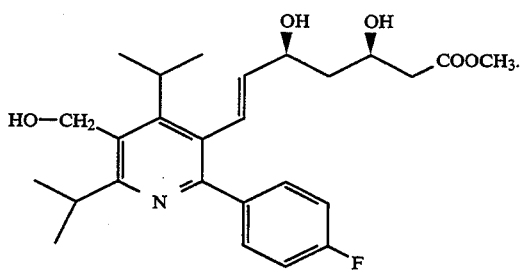

4. A composition for inhibiting cholesterol biosynthesis and HMG-CoA reductase comprising an amount effective therefor of a compound according to claim 1 and a pharmaceutically acceptable diluent.

5. A method of treating a patient afflicted with hyperlipoproteinaemia, lipoproteinaemia or arteriosclerosis which comprises administering to such patient an amount effective therefor of a compound according to claim 1.

* * * * *

UNITED STATES PATENT AND TRADEMARK OFFICE
CERTIFICATE OF CORRECTION

PATENT NO. : 5,401,746

DATED : March 28, 1995

INVENTOR(S) : Angerbauer, et al.

It is certified that error appears in the above-identified patent and that said Letters Patent is hereby corrected as shown below:

Title Page & Col. 1 line 4     [54] Title: Delete " LIPOPOTAEMIA " and substitute -- LIPOPROTAEMIA --

Title Page     [30] Foreign Application Priority Data: after " Jul. 11 " delete " 1980 " and substitute -- 1988 -- and after " 21317 " insert -- A --

Title Page     [30 ] Foreign Application Priority Data: After " Jan. 20, 1988 [DE] Germany... " delete " 33 01 406.8 " and substitute -- 38 01 406.8 --

Signed and Sealed this

Thirteenth Day of June, 1995

*Attest:*

*Attesting Officer*

BRUCE LEHMAN

*Commissioner of Patents and Trademarks*